(12) United States Patent  (10) Patent No.: US 8,518,931 B2
Jiang et al.  (45) Date of Patent: Aug. 27, 2013

(54) COMPOUNDS AND COMPOSITIONS AS KINASE INHIBITORS

(75) Inventors: Tao Jiang, San Diego, CA (US);
Pierre-Yves Michellys, San Marcos, CA (US); Truc Ngoc Nguyen, San Diego, CA (US); Wei Pei, San Diego, CA (US); Baogen Wu, San Diego, CA (US); Xuefeng Zhu, San Diego, CA (US)

(73) Assignee: IRM LLC, Hamilton (BM)

( * ) Notice: Subject to any disclaimer, the term of this patent is extended or adjusted under 35 U.S.C. 154(b) by 208 days.

(21) Appl. No.: 12/936,193

(22) PCT Filed: Apr. 3, 2009

(86) PCT No.: PCT/US2009/039380
§ 371 (c)(1),
(2), (4) Date: Dec. 23, 2010

(87) PCT Pub. No.: WO2009/126514
PCT Pub. Date: Oct. 15, 2009

(65) Prior Publication Data
US 2011/0190264 A1  Aug. 4, 2011

Related U.S. Application Data

(60) Provisional application No. 61/043,111, filed on Apr. 7, 2008, provisional application No. 61/095,883, filed on Sep. 10, 2008.

(51) Int. Cl.
*C07D 401/12* (2006.01)
*C07D 487/04* (2006.01)
*A61K 31/53* (2006.01)
*A61P 35/00* (2006.01)

(52) U.S. Cl.
USPC .......................... 514/208; 544/209; 514/246

(58) Field of Classification Search
USPC .................. 544/208, 209; 514/246
See application file for complete search history.

(56) References Cited

U.S. PATENT DOCUMENTS

| 7,517,882 B2 * | 4/2009 | Chu et al. ............ 514/243 |
| 2005/0187219 A1 | 8/2005 | Guzi et al. |
| 2006/0106019 A1 | 5/2006 | Bernard |
| 2008/0045536 A1 | 2/2008 | Vaccaro et al. |
| 2008/0070893 A1 | 3/2008 | Chu et al. |

FOREIGN PATENT DOCUMENTS

| DE | 2424334 | 12/1974 |
| JP | 2006160628 | 6/2006 |
| WO | WO 02/50079 | 6/2002 |
| WO | WO 2008/057402 | 5/2008 |

OTHER PUBLICATIONS

Mass, R. D., Int. J. Radiation Oncology Bio. Phys.vol. 58(3): 932-940, 2004.*
Fabbro et al. Pharmacology & therapeutics 93, 79-98, 2002.*
Cohen et al., Current Opinion in Chemical Biology, 3,459-465, 1999.*
Freshney et al.,Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531-537, 1999.*
Cecil Textbook of Medicine, edited by Bennet, J.C., and Plum F., 20th edition,vol. 1, 1004-1010, 1996.*
Griffiths, P.A. Journal of Virology, 46, 3-8, 2009.*
Nie et al. Bioorganic & Medicinal Chemistry Letters (2007), 17(15), 4191-4195.*
Turner et al., Current Pharmaceutical Design. 2, 209-224, 1996.*
Sugar et al., Diagno Microbiol. Infect. Dis. 21: 129-133, 1995.*
Snyder et al., J. Med. Liban 48(4): 208-214, 2000. PubMed Abstract.*
Nie, et al., "Structure-based design, synthesis, and study of pyrazolo[1,5-a][1,3,5]triazine derivatives as potent inhibitors of protein kinase CK2", Bioorganic & Medicinal Chemistry letters, 2007, pp. 4191-4195, vol. 17, Elsevier Ltd.
Nie, et al., "Structure-based design and synthesis of noval macrocyclic pyrazolo[1,5-a][1,3,5]triazine compounds as potent inhibitors of protein kinase CK2 and their anticancer activities", Bioorganic & Medicinal Chemistry Letters, pp. 619-623, 2008, vol. 8, Elsevier Ltd.

* cited by examiner

*Primary Examiner* — Venkataraman Balasubramanian
(74) *Attorney, Agent, or Firm* — Emily Tongco Wu; Genomics Institute of the Movartis Research Foundation

(57) ABSTRACT

The invention relates to triazine and pyrimidine derivatives having Formula (1) or (2), and methods for using such compounds. For example, the compounds of the invention may be used to treat, ameliorate or prevent a condition which responds to inhibition of anaplastic lymphoma kinase (ALK) activity, c-ros oncogene (ROS), insulin-like growth factor (IGF-IR), and/or insulin receptor (InsR) or a combination thereof.

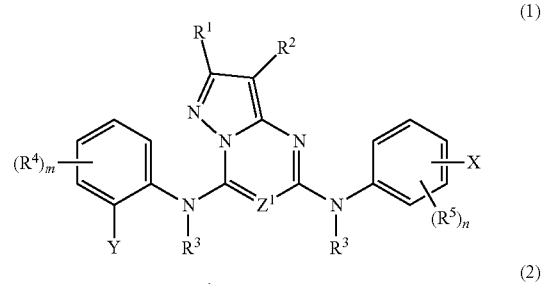

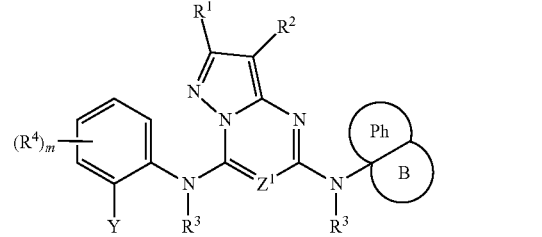

19 Claims, No Drawings

COMPOUNDS AND COMPOSITIONS AS KINASE INHIBITORS

CROSS-REFERENCE TO RELATED APPLICATIONS

This application is a 371 U.S. national phase application of international application number PCT/US2009/039380 filed 3 Apr. 2009, which application claims priority to U.S. provisional patent application No. 61/095,883 filed 10 Sep. 2008 and U.S. provisional patent application No. 61/043,111 filed 7 Apr. 2008, each of which is incorporated herein by reference in its entirety and for all purposes.

TECHNICAL FIELD

The invention relates to protein kinase inhibitors, and methods of using such compounds. More particularly, the invention relates to inhibitors of Ros, IGF-1R, Ins and anaplastic lymphoma kinase (ALK) and their uses as therapeutic agents.

BACKGROUND ART

Cancer is a disease resulting from an abnormal growth of tissue. Certain cancers have the potential to invade into local tissues and also metastasize to distant organs. This disease can develop in a wide variety of different organs, tissues and cell types. Therefore, the term "cancer" refers to a collection of over a thousand different diseases.

Anaplastic lymphoma kinase (ALK), a member of the insulin receptor superfamily of receptor tyrosine kinases, has been implicated in oncogenesis in hematopoietic and non-hematopoietic tumors. The aberrant expression of full-length ALK receptor proteins has been reported in neuroblastomas and glioblastomas; and ALK fusion proteins have occurred in anaplastic large cell lymphoma. The study of ALK fusion proteins has also raised the possibility of new therapeutic treatments for patients with ALK-positive malignancies. (Pulford et al., Cell. Mol. Life Sci. 61:2939-2953 (2004)).

Insulin-like growth factor (IGF-1) signaling is highly implicated in cancer, with the IGF-1 receptor (IGF-1R) as the predominating factor. IGR-1R is important for tumor transformation and survival of malignant cells, but is only partially involved in normal cell growth. Targeting of IGF-1R has been suggested to be a promising option for cancer therapy. (Larsson et al., Br. J. Cancer 92:2097-2101 (2005)).

The c-ros oncogene 1 (ROS1, also known as ROS), a member of the tyrosine kinase insulin receptor gene family, is highly expressed in a variety of tumor cell lines.

Despite advancements in the art, there remains a need for cancer treatments and anti-cancer compounds.

DISCLOSURE OF THE INVENTION

The invention relates to triazine and pyrimidine derivatives and pharmaceutical compositions thereof, and their use as therapeutic agents.

In one aspect, the invention provides a compound of Formula (1) or (2):

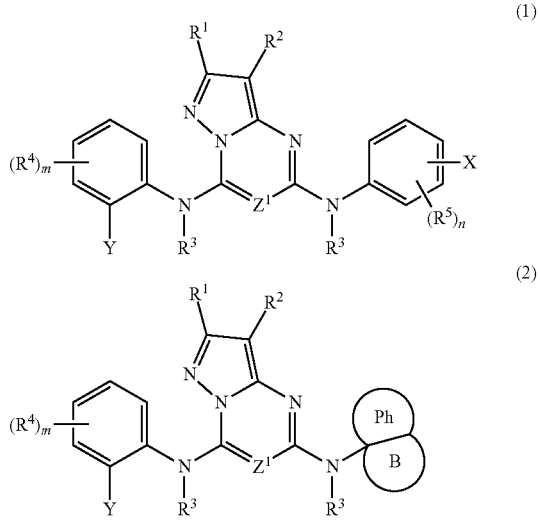

or a physiologically acceptable salt thereof;

X is a $C_{3-12}$ carbocyclic ring, $C_{6-10}$ aryl, or a 5-10 membered heteroaryl or 4-10 membered heterocyclic ring containing $NR^6$, O or S, each of which is optionally substituted with 1-3 $R^{5'}$ groups;

alternatively, X is a $C_{1-6}$ alkyl, $C_{2-6}$ alkenyl or $C_{2-6}$ alkynyl, each of which may be optionally substituted with halo, amino, hydroxyl or alkoxy; or X is $(CR_2)_{0-4}CO_2R^7$ or $(CR_2)_{0-4}CR(NRR^7)(CO_2R^7)$;

Y is $S(O)_{0-2}R^8$, $SO_2NRR^7$ or $CONRR^7$;

$Z^1$ is N or CH;

Ph is phenyl and B is a 5-6 membered ring optionally containing $NR^6$, O, =O or S; and Ph and B are optionally substituted with 1-3 $R^{5'}$ groups;

$R^1$ and $R^2$ are independently H, halo, $C_{1-6}$ alkyl, $C_{2-6}$ alkenyl or $C_{2-6}$ alkynyl; or $R^1$ and $R^2$ together with the ring atoms to which they are attached form a fused 5-, 6- or 7-membered cycloalkyl, aryl, heteroaryl or heterocyclic ring;

each $R^3$ is the same or different and is independently H or $C_{1-6}$ alkyl;

$R^4$, $R^5$ and $R^{5'}$ are independently $C_{1-6}$ alkyl, $C_{1-6}$ alkoxy, $C_{2-6}$ alkenyl or $C_{2-6}$ alkynyl, each of which may be optionally substituted with halo, amino or hydroxyl; halo, nitro, cyano, $C(R)(OR^7)(R^7)$, $OR^7$, $NR(R^7)$, $C(R)(NRR^7)(R^7)$, $(CR_2)_q$—W, $C(O)O_{0-1}R^7$, $C(O)NR(R^7)$, $C(O)CRR^7$—$NR(R^7)$, $C(O)NR(CR_2)_pNR(R^7)$, $C(O)NR(CR_2)_pOR^7$, $C(O)NR(CR_2)_pSR^7$, $C(O)NR(CR_2)_qS(O)_{1-2}R^8$, $S(O)_{0-2}R^8$, $(CR_2)_{1-6}NR(CR_2)_pOR^7$, $(CR_2)_{1-6}NR(CR_2)_qC(O)R^8$, $S(O)_2NRR^7$, $S(O)_2NR(CR_2)_pNR(R^7)$, or $S(O)_2NR(CR_2)_pOR^7$;

$R^6$ is H, $C_{1-6}$ alkyl, $C_{2-6}$ alkenyl or $C_{2-6}$ alkynyl, each of which may be optionally substituted with halo, amino, hydroxyl or alkoxy; —$(CR_2)_{1-4}$—CN, $(CR_2)_p$—$OR^7$, $(CR_2)_p$—$NR(R^7)$, -L-W, -L-C(O)—$R^7$, —$(CR_2)_{1-4}$—C(O)—$(CR_2)_q$—$OR^7$, —C(O)$OR^8$, -L-C(O)—$NRR^7$, -L-CR$(OR^7)$—$C_tF_{(2t+1)}$ wherein t is 1-3; -L-C(O)—CR($R^7$)—$NRR^7$, -L-C(O)—NR—$(CR_2)_p$—$NRR^7$, -L-C(O)NR$(CR_2)_p$$OR^7$, -L-C(O)—$(CR_2)_q$—NR—C(O)—$R^8$, -L-C(O)NR$(CR_2)_p$$SR^7$, -L-C(O)NR$(CR_2)_q$$S(O)_{1-2}R^8$, $(CR_2)_p$NR$(CR_2)_p$$OR^7$, $(CR_2)_p$NR-L-C(O)$R^8$, -L-$S(O)_2R^8$, -L-$S(O)_2NRR^7$, -L-$S(O)_2NR(CR_2)_pNR(R^7)$, -L-$S(O)_2NR(CR_2)_pOR^7$ or a radical selected from formula (a), (b) or (c):

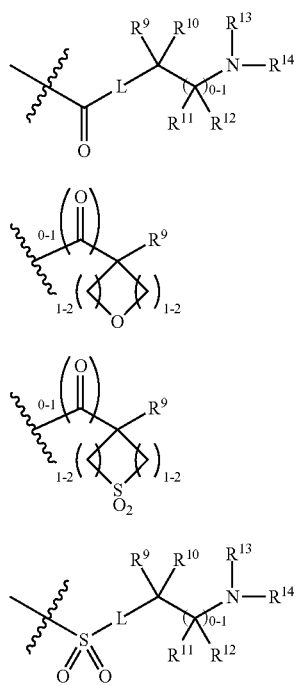

(a)

(b)

(c)

(d)

wherein $R^9$, $R^{10}$, $R^{11}$, $R^{12}$, $R^{13}$ and $R^{14}$ are independently selected from H, or $C_{1-6}$ alkyl, $C_{1-6}$ alkoxy, $C_{2-6}$ alkenyl or $C_{2-6}$ alkynyl, each of which may be optionally substituted with halo, amino, hydroxyl or alkoxy; or $R^9$ and $R^{10}$, $R^{10}$ and $R^{13}$, $R^{13}$ and $R^{14}$, $R^{11}$ and $R^{12}$, or $R^{11}$ and $R^{13}$ together with the carbon and/or nitrogen atoms to which they are attached may form a 3-7 membered saturated, unsaturated or partially unsaturated ring optionally containing up to 3 atoms or groups selected from C(O), N, O and $S(O)_{0-2}$ and optionally substituted with 1-3 $R^5$ groups;

L is $(CR_2)_{1-4}$ or a bond;

$R^7$ and $R^8$ are independently $(CR_2)_q$—W, or $C_{1-6}$ alkyl, $C_{2-6}$ alkenyl or $C_{2-6}$ alkynyl, each of which may be optionally substituted with halo, amino, hydroxyl, or alkoxy; or $R^7$ is H;

W is a $C_{3-12}$ carbocyclic ring, $C_{6-10}$ aryl, or a 5-10 membered heteroaryl or 4-10 membered heterocyclic ring, each of which is optionally substituted with 1-3 $R^{5'}$ groups;

each R is H or $C_{1-6}$ alkyl;

m and n are independently 0-2;

p is 2-4; and q is 0-4.

In some examples, X in the above Formula (1) is a 5-6 membered heteroaryl; or X is a $C_{1-6}$ alkyl, $C_{2-6}$ alkenyl or $C_{2-6}$ alkynyl, each of which may be optionally substituted with halo, amino or hydroxyl; $(CR_2)_{1-4}CO_2R^7$ or $(CR_2)_{1-4}CR(NRR^7)(CO_2R^7)$;

n is 0-1; and $R^{5'}$ if present on X, is hydroxyl, $C_{1-6}$ alkyl, $C_{1-6}$ alkoxy, halo-substituted $C_{1-6}$ alkyl or halo-substituted $C_{1-6}$ alkoxy.

In other examples, X in the above Formula (1) is a 6 membered heterocyclic ring containing $NR^6$, O or S.

In one embodiment, the invention provides a compound of Formula (2A), (2B) or (2C):

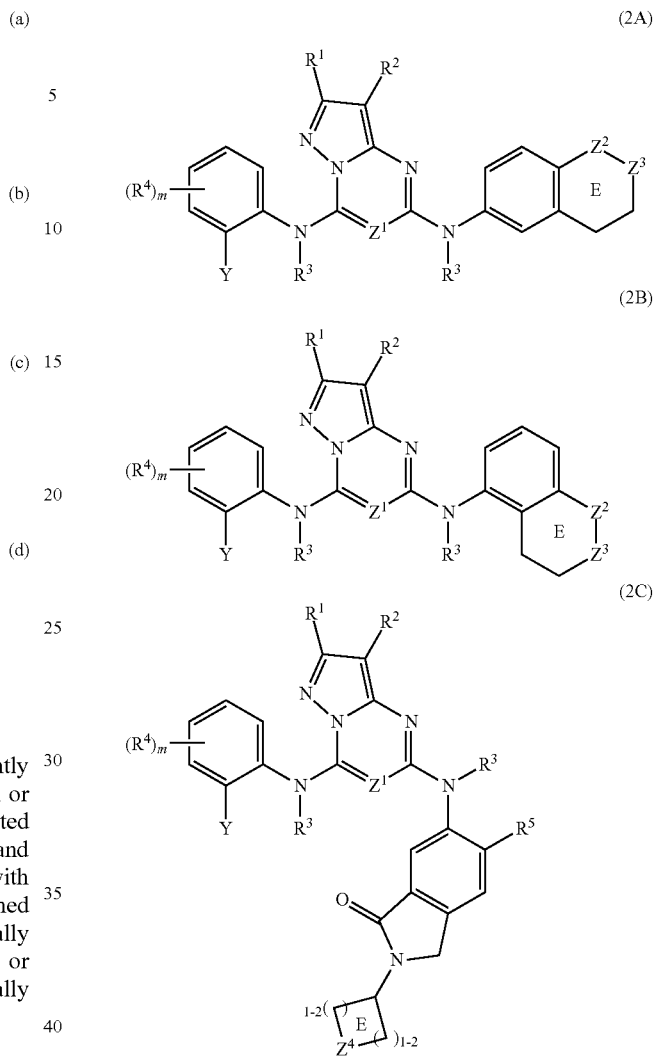

wherein one of $Z^2$ and $Z^3$ is $NR^6$, O or S, and the other is $CH_2$;

$Z^4$ is $NR^6$, O or S;

ring E may optionally contain a double bond;

$R^6$ is H, $-(CR_2)_{1-4}-C(O)-(CR_2)_q-OR^7$, $-C(O)OR^8$ or $-L-S(O)_2R^8$; and R, $R^1$, $R^2$, $R^3$, $R^4$, $R^5$ and m are as defined in Formula (1) or (2).

In another embodiment, the invention provides a compound of Formula (3A) or (3B):

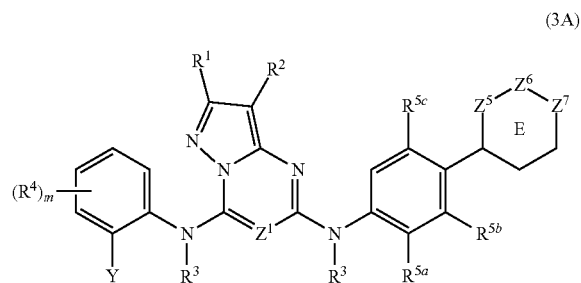

(3A)

-continued (3B)

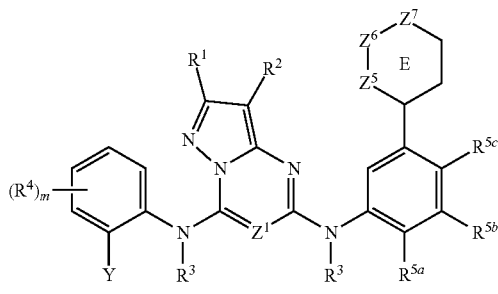

wherein $R^{5a}$, $R^{5b}$ and $R^{5c}$ are independently H, halo, hydroxyl, $C_{1-6}$ alkyl, $C_{1-6}$ alkoxy, halo-substituted $C_{1-6}$ alkyl or halo-substituted $C_{1-6}$ alkoxy;

one of $Z^5$, $Z^6$ and $Z^7$ is $NR^6$, O or S, and the others are $CH_2$; and $R^1$, $R^2$, $R^3$, $R^4$, $R^5$, $R^6$ and m are as defined in Formula (1) or (2).

In some examples, $Z^7$ in the above Formula (3A) or (3B) is $NR^6$ or O; and $Z^5$ and $Z^6$ are $CH_2$. In particular examples, $R^6$ is H, $C_{1-6}$ alkyl, $C_{2-6}$ alkenyl or $C_{2-6}$ alkynyl, each of which may be optionally substituted with halo, amino or hydroxyl groups; halo, nitro or cyano; L-W, -L-C(O)—$R^7$, —$(CR_2)_{1-4}$— $C(O)$—$(CR_2)_q$—$OR^7$, —$C(O)OR^8$, -L-C(O)—$NRR^7$, L-C(O)—$CR(R^7)$—$NRR^7$, -L-S(O)$_2R^8$, or a radical of formula (a) or (b):

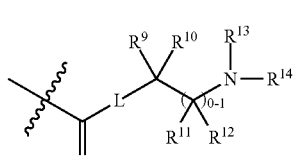

(a)

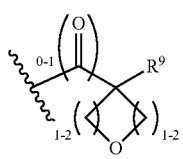

(b)

wherein R, $R^7$, $R^8$, $R^9$, $R^{10}$, $R^{11}$, $R^{12}$, $R^{13}$, $R^{14}$ are as defined in Formula (1) or (2).

In yet another embodiment, the invention provides a compound of Formula (3C) or (3D):

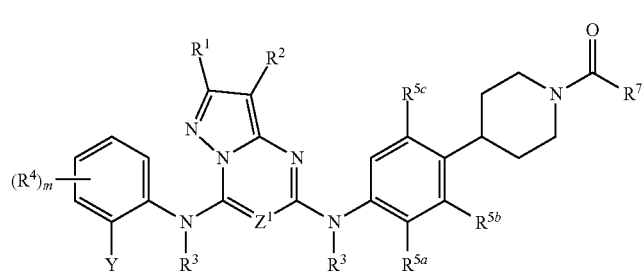

(3C)

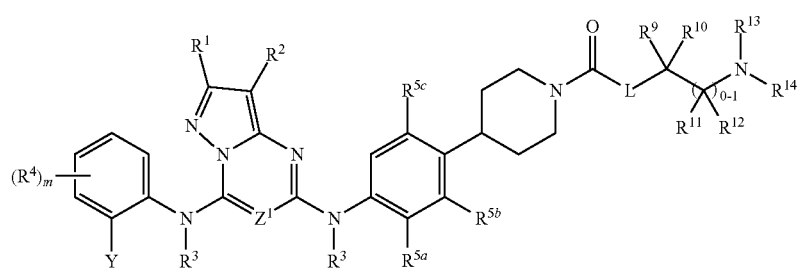

(3D)

wherein $R^{5a}$, $R^{5b}$ and $R^{5c}$ are independently H, halo, hydroxyl, $C_{1-6}$ alkyl, $C_{1-6}$ alkoxy, halo-substituted $C_{1-6}$ alkyl or halo-substituted $C_{1-6}$ alkoxy;

$R^7$ is $(CR_2)_q$—W, or $C_{1-6}$ alkyl, $C_{2-6}$ alkenyl or $C_{2-6}$ alkynyl, each of which may be optionally substituted with halo, amino, hydroxyl, or alkoxy;

W is a 5-6 membered heterocyclic ring; and

R, $R^1$, $R^2$, $R^3$, $R^4$, $R^9$, $R^{10}$, $R^{11}$, $R^{12}$, $R^{13}$, $R^{14}$, L, q and m are as defined in Formula (1) or (2).

In some examples in the above Formula (3A), (3B), (3C) or (3D), $R^{5b}$ is H; and $R^{5a}$ and $R^{5c}$ are independently halo, hydroxyl, $C_{1-6}$ alkyl, $C_{1-6}$ alkoxy, halo-substituted $C_{1-6}$ alkyl or halo-substituted $C_{1-6}$ alkoxy. In other embodiments, $R^{5b}$ is H; and $R^{5a}$ and $R^{5c}$ are independently $C_{1-6}$ alkyl or $C_{1-6}$ alkoxy. In other examples, the invention provides compounds of Formula (3D), wherein L is a bond, and $R^9$ and $R^{10}$, $R^{10}$ and $R^{13}$, $R^{13}$ and $R^{14}$, $R^{11}$ and $R^{12}$, or $R^{11}$ and $R^{13}$ together with the carbon and/or nitrogen atoms to which they are attached forms a 5-6 membered ring optionally containing N, O or $S(O)_{0-2}$.

In any of the above compounds, $R^1$, $R^2$ and $R^3$ may be H. In other examples, $Z^1$ is N. In yet other examples, m is 0 and Y is $SO_2R^8$ and $R^7$ and $R^8$ are $C_{1-6}$ alkyl.

In yet another aspect, the present invention provides pharmaceutical compositions comprising a compound having Formula (1), (2), (2A), (2B), (2C), (3A), (3B), (3C) or (3D) and a physiologically acceptable excipient.

In yet another aspect, the invention provides methods for inhibiting a kinase in a cell, comprising contacting the cell with an effective amount of a compound having Formula (1), (2), (2A), (2B), (2C), (3A), (3B), (3C) or (3D) or a physiologically acceptable salt thereof, and optionally in combination with a second therapeutic agent, wherein said kinase is selected from Ros, IGF-1R, InsR and anaplastic lymphoma kinase; thereby inhibiting said kinase.

The invention also provides methods to treat, ameliorate or prevent a condition which responds to inhibition of Ros, IGF-1R, InsR or ALK, comprising administering to a subject in need of such treatment an effective amount of a compound having Formula (1), (2), (2A), (2B), (2C), (3A), (3B), (3C) or (3D), or a pharmaceutically acceptable salt or pharmaceutical composition thereof, thereby treating said condition. Alternatively, the present invention provides the use of a compound having Formula (1), (2), (2A), (2B), (2C), (3A), (3B), (3C) or (3D) in the manufacture of a medicament for treating a condition mediated by Ros, IGF-1R, InsR or ALK. The compounds of the invention may be used alone or in combination with a second therapeutic agent, such as a chemotherapeutic agent, to treat a condition mediated by Ros, IGF-1R, InsR or ALK.

In particular embodiments, the invention provides a method for treating an ALK-mediated condition in a subject suffering therefrom, comprising administering to the mammal a therapeutically effective amount of a compound having Formula (1), (2), (2A), (2B), (2C), (3A), (3B), (3C) or (3D) or a physiologically acceptable salt thereof, and optionally in combination with a chemotherapeutic agent, wherein the ALK-mediated condition is an autoimmune disease, a transplantation disease, an infectious disease or a cell proliferative disorder. In other embodiments, the invention provides methods for treating a cell proliferative disorder, comprising administering to a subject in need of such treatment an effective amount of a compound having Formula (1), (2), (2A), (2B), (2C), (3A), (3B), (3C) or (3D), or a pharmaceutically acceptable salt or pharmaceutical composition thereof, and optionally in combination with a second therapeutic agent, thereby treating said condition. Alternatively, the present invention provides the use of a compound having Formula (1), (2), (2A), (2B), (2C), (3A), (3B), (3C) or (3D) in the manufacture of a medicament for treating a cell-proliferative disorder. In particular examples, the compounds of the invention may be used alone or in combination with a chemotherapeutic agent to treat a cell proliferative disorder, including but not limited to, multiple myeloma, neuroblastoma, lymphoma, leukemia, melanoma, sarcoma, osteosarcoma, synovial sarcoma, Ewing's sarcoma, hepatoma, gastrointestinal stromal tumor or a solid tumor of breast, renal, prostate, colorectal, thyroid, ovarian, pancreas, lung, uterus, respiratory tract, brain, digestive tract, urinary tract, eye, liver, skin, head and neck, thyroid or parathyroid.

DEFINITIONS

"Alkyl" refers to a moiety and as a structural element of other groups, for example halo-substituted-alkyl and alkoxy, and may be straight-chained or branched. An optionally substituted alkyl, alkenyl or alkynyl as used herein may be optionally halogenated (e.g., $CF_3$), or may have one or more carbons that is substituted or replaced with a heteroatom, such as NR, O or S (e.g., —$OCH_2CH_2O$—, alkylthiols, thioalkoxy, alkylamines, etc).

"Aryl" refers to a monocyclic or fused bicyclic aromatic ring containing carbon atoms. "Arylene" means a divalent radical derived from an aryl group. For example, an aryl group may be phenyl, indenyl, indanyl, naphthyl, or 1,2,3,4-tetrahydronaphthalenyl, which may be optionally substituted in the ortho, meta or para position.

"Heteroaryl" as used herein is as defined for aryl above, where one or more of the ring members is a heteroatom. Examples of heteroaryls include but are not limited to pyridyl, pyrazinyl, indolyl, indazolyl, quinoxalinyl, quinolinyl, benzofuranyl, benzopyranyl, benzothiopyranyl, benzo[1,3]dioxole, imidazolyl, benzo-imidazolyl, pyrimidinyl, furanyl, oxazolyl, isoxazolyl, triazolyl, benzotriazolyl, tetrazolyl, pyrazolyl, thienyl, pyrrolyl, isoquinolinyl, purinyl, thiazolyl, tetrazinyl, benzothiazolyl, oxadiazolyl, benzoxadiazolyl, etc.

A "carbocyclic ring" as used herein refers to a saturated or partially unsaturated, monocyclic, fused bicyclic or bridged polycyclic ring containing carbon atoms, which may optionally be substituted, for example, with =O. Examples of carbocyclic rings include but are not limited to cyclopropyl, cyclobutyl, cyclopentyl, cyclohexyl, cyclopropylene, cyclohexanone, etc.

A "heterocyclic ring" as used herein is as defined for a carbocyclic ring above, wherein one or more ring carbons is a heteroatom. For example, a heterocyclic ring may contain N, O, S, —N=, —S—, —S(O), —$S(O)_2$—, or —NR— wherein R may be hydrogen, $C_{1-4}$alkyl or a protecting group. Examples of heterocyclic rings include but are not limited to morpholino, pyrrolidinyl, pyrrolidinyl-2-one, piperazinyl, piperidinyl, piperidinylone, 1,4-dioxa-8-aza-spiro[4.5]dec-8-yl, 1,2,3,4-tetrahydroquinolinyl, etc. Heterocyclic rings as used herein may encompass bicyclic amines and bicyclic diamines.

As used herein, an H atom in any substituent groups (e.g., $CH_2$) encompasses all suitable isotopic variations, e.g., H, $^2H$ and $^3H$.

Unless otherwise indicated, when a substituent is deemed to be "optionally substituted," it is meant that the substituent is a group that may be substituted with one or more group(s) individually and independently selected from, for example, an optionally halogenated alkyl, alkenyl, alkynyl, alkoxy, alkylamine, alkylthio, alkynyl, amide, amino, including mono- and di-substituted amino groups, aryl, aryloxy, arylthio, carbonyl, carbocyclic, cyano, cycloalkyl, halogen, heteroalkyl, heteroalkenyl, heteroalkynyl, heteroaryl, heterocyclic, hydroxy, isocyanato, isothiocyanato, mercapto, nitro, O-carbamyl, N-carbamyl, O-thiocarbamyl, N-thiocarbamyl, C-amido, N-amido, S-sulfonamido, N-sulfonamido, C-carboxy, O-carboxy, perhaloalkyl, perfluoroalkyl, silyl, sulfonyl, thiocarbonyl, thiocyanato, trihalomethanesulfonyl, and the protected compounds thereof. The protecting groups that may form the protected compounds of the above substituents are known to those of skill in the art and may be found in references such as Greene and Wuts, Protective Groups in Organic Synthesis, 3$^{rd}$ Ed., John Wiley & Sons, New York, N.Y., 1999, and Kocienski, Protective Groups, Thieme Verlag, New York, N.Y., 1994, which are incorporated herein by reference in their entirety.

The term "pharmaceutical combination" as used herein refers to a product obtained from mixing or combining active ingredients, and includes both fixed and non-fixed combinations of the active ingredients. The term "fixed combination" means that the active ingredients, e.g. a compound of Formula (1) and a co-agent, are both administered to a patient simultaneously in the form of a single entity or dosage. The term "non-fixed combination" means that the active ingredients, e.g. a compound of Formula (1) and a co-agent, are both administered to a patient as separate entities either simultaneously, concurrently or sequentially with no specific time limits, wherein such administration provides therapeutically effective levels of the active ingredients in the body of the patient. The latter also applies to cocktail therapy, e.g. the administration of three or more active ingredients.

The term "therapeutically effective amount" means the amount of the subject compound that will elicit a biological or medical response in a cell, tissue, organ, system, animal or human that is being sought by the researcher, veterinarian, medical doctor or other clinician.

"Subject" refers to humans and mammals, including domestic and farm animals, and zoo, sports, or pet animals, such as dogs, cats, cattle, horses, sheep, pigs, goats, rabbits, etc. In certain embodiments, the subject is human.

Administration "in combination with" one or more further therapeutic agents includes simultaneous (concurrent) and consecutive administration in any order.

MODES OF CARRYING OUT THE INVENTION

The invention provides triazine and pyrimidine derivatives and pharmaceutical compositions thereof, and methods for using such compounds.

In one aspect, the invention provides a compound of Formula (1) or (2):

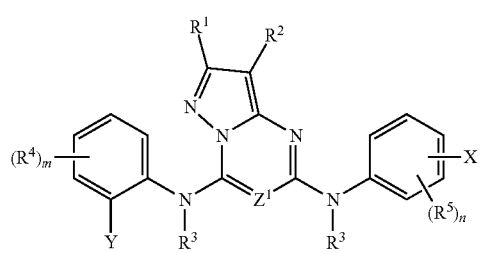

(1)

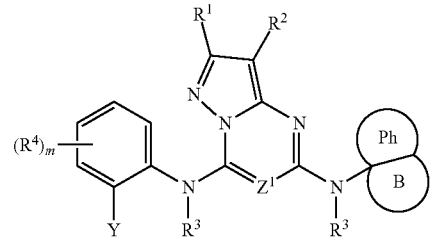

(2)

or a physiologically acceptable salt thereof;

X is a $C_{3-12}$ carbocyclic ring, $C_{6-10}$ aryl, or a 5-10 membered heteroaryl or 4-10 membered heterocyclic ring containing $NR^6$, O or S, each of which is optionally substituted with 1-3 $R^{5'}$ groups;

alternatively, X is a $C_{1-6}$ alkyl, $C_{2-6}$ alkenyl or $C_{2-6}$ alkynyl, each of which may be optionally substituted with halo, amino, hydroxyl or alkoxy; or X is $(CR_2)_{0-4}CO_2R^7$ or $(CR_2)_{0-4}CR(NRR^7)(CO_2R^7)$;

Y is $S(O)_{0-2}R^8$, $SO_2NRR^7$ or $CONRR^7$;

$Z^1$ is N or CH;

Ph is phenyl and B is a 5-6 membered ring optionally containing $NR^6$, O, =O or S; and Ph and B are optionally substituted with 1-3 $R^{5'}$ groups;

$R^1$ and $R^2$ are independently H, halo, $C_{1-6}$ alkyl, $C_{2-6}$ alkenyl or $C_{2-6}$ alkynyl; or $R^1$ and $R^2$ together with the ring atoms to which they are attached form a fused 5-, 6- or 7-membered cycloalkyl, aryl, heteroaryl or heterocyclic ring;

each $R^3$ is the same or different and is independently H or $C_{1-6}$ alkyl;

$R^4$, $R^5$ and $R^{5'}$ are independently $C_{1-6}$ alkyl, $C_{1-6}$ alkoxy, $C_{2-6}$ alkenyl or $C_{2-6}$ alkynyl, each of which may be optionally substituted with halo, amino or hydroxyl; halo, nitro, cyano, $C(R)(OR^7)(R^7)$, $OR^7$, $NR(R^7)$, $C(R)(NRR^7)(R^7)$, $(CR_2)_q$—W, $C(O)O_{0-1}R^7$, $C(O)NR(R^7)$, $C(O)CRR^7$—$NR(R^7)$, $C(O)NR(CR_2)_pNR(R^7)$, $C(O)NR(CR_2)_pOR^7$, $C(O)NR(CR_2)_pSR^7$, $C(O)NR(CR_2)_qS(O)_{1-2}R^8$, $S(O)_{0-2}R^8$, $(CR_2)_{1-6}NR(CR_2)_pOR^7$, $(CR_2)_{1-6}NR(CR_2)_qC(O)R^8$, $S(O)_2NRR^7$, $S(O)_2NR(CR_2)_pNR(R^7)$, or $S(O)_2NR(CR_2)_pOR^7$;

$R^6$ is H, $C_{1-6}$ alkyl, $C_{2-6}$ alkenyl or $C_{2-6}$ alkynyl, each of which may be optionally substituted with halo, amino, hydroxyl or alkoxy; —$(CR_2)_{1-4}$—CN, $(CR_2)_p$—$OR^7$, $(CR_2)_p$—$NR(R^7)$, -L-W, -L-C(O)—$R^7$, —$(CR_2)_{1-4}$—C(O)—$(CR_2)_q$—$OR^7$, —C(O)$OR^8$, -L-C(O)—$NRR^7$, -L-CR$(OR^7)$—$C_tF_{(2t+1)}$ wherein t is 1-3; -L-C(O)—CR$(R^7)$—$NRR^7$, -L-C(O)—NR—$(CR_2)_p$—$NRR^7$, -L-C(O)NR$(CR_2)_pOR^7$, -L-C(O)—$(CR_2)_q$—NR—C(O)—$R^8$, -L-C(O)NR$(CR_2)_pSR^7$, -L-C(O)NR$(CR_2)_qS(O)_{1-2}R^8$, $(CR_2)_pNR(CR_2)_pOR^7$, $(CR_2)_pNR$-L-C(O)$R^8$, -L-S(O)$_2R^8$, -L-S(O)$_2NRR^7$, -L-S(O)$_2NR(CR_2)_pNR(R^7)$, -L-S(O)$_2NR(CR_2)_pOR^7$ or a radical selected from formula (a), (b) or (c):

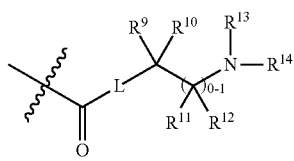

(a)

-continued (b)
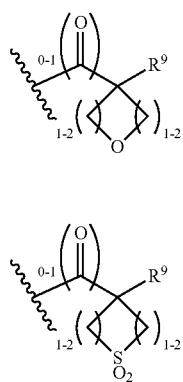

(c)

(d)
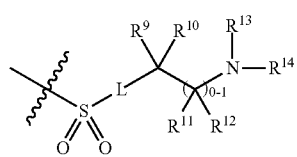

wherein $R^9$, $R^{10}$, $R^{11}$, $R^{12}$, $R^{13}$ and $R^{14}$ are independently selected from H, or $C_{1-6}$ alkyl, $C_{1-6}$ alkoxy, $C_{2-6}$ alkenyl or $C_{2-6}$ alkynyl, each of which may be optionally substituted with halo, amino, hydroxyl or alkoxy; or $R^9$ and $R^{10}$, $R^{10}$ and $R^{13}$ and $R^{14}$, $R^{11}$ and $R^{12}$, or $R^{11}$ and $R^{13}$ together with the carbon and/or nitrogen atoms to which they are attached may form a 3-7 membered saturated, unsaturated or partially unsaturated ring optionally containing up to 3 atoms or groups selected from C(O), N, O and $S(O)_{0-2}$ and optionally substituted with 1-3 $R^5$ groups;

L is $(CR_2)_{1-4}$ or a bond;

$R^7$ and $R^8$ are independently $(CR_2)_q$—W, or $C_{1-6}$ alkyl, $C_{2-6}$ alkenyl or $C_{2-6}$ alkynyl, each of which may be optionally substituted with halo, amino, hydroxyl, or alkoxy; or $R^7$ is H;

W is a $C_{3-12}$ carbocyclic ring, $C_{6-10}$ aryl, or a 5-10 membered heteroaryl or 4-10 membered heterocyclic ring, each of which is optionally substituted with 1-3 $R^{5'}$ groups;

each R is H or $C_{1-6}$ alkyl;

m and n are independently 0-2;

p is 2-4; and q is 0-4.

In one embodiment, the invention provides a compound of Formula (2A), (2B) or (2C):

(2A)
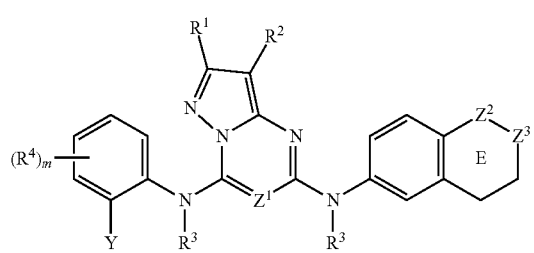

(2B)
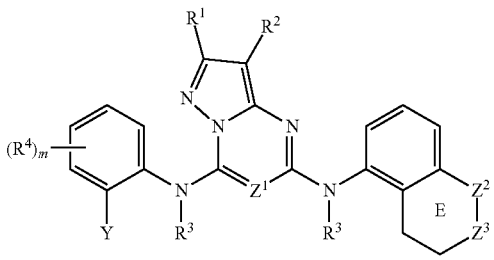

(2C)
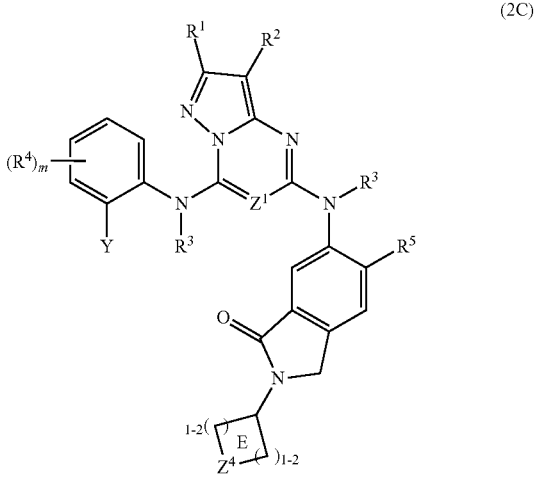

wherein one of $Z^2$ and $Z^3$ is $NR^6$, O or S, and the other is $CH_2$;

$Z^4$ is $NR^6$, O or S;

ring E may optionally contain a double bond;

$R^6$ is H, —$(CR_2)_{1-4}$—C(O)—$(CR_2)_q$—$OR^7$, —C(O)$OR^8$ or -L-$S(O)_2R^8$; and R, $R^1$, $R^2$, $R^3$, $R^4$, $R^5$ and m are as defined in Formula (1) or (2).

In another embodiment, the invention provides a compound of Formula (3A) or (3B):

(3A)
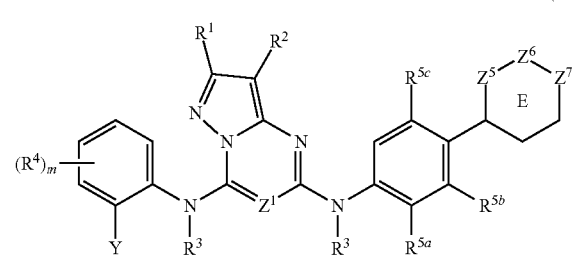

-continued (3B)

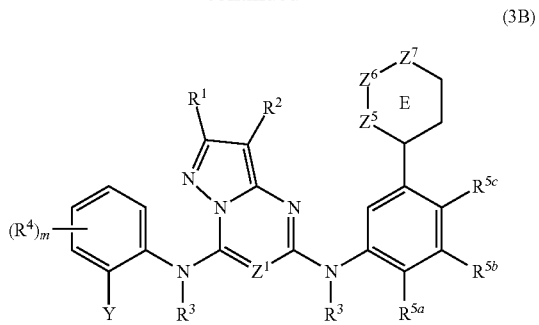

wherein $R^{5a}$, $R^{5b}$ and $R^{5c}$ are independently H, halo, hydroxyl, $C_{1-6}$ alkyl, $C_{1-6}$ alkoxy, halo-substituted $C_{1-6}$ alkyl or halo-substituted $C_{1-6}$ alkoxy;

one of $Z^5$, $Z^6$ and $Z^7$ is $NR^6$, O or S, and the others are $CH_2$; and $R^1$, $R^2$, $R^3$, $R^4$, $R^5$, $R^6$ and m are as defined in Formula (1) or (2).

In yet another embodiment, the invention provides a compound of Formula (3C) or (3D):

(3C)

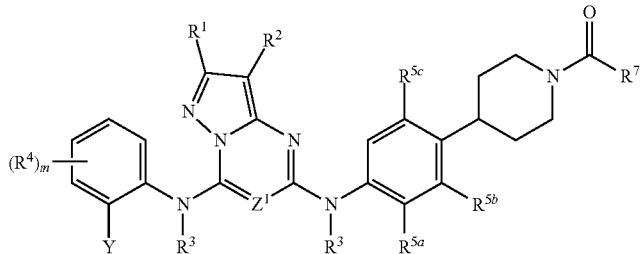

(3D)

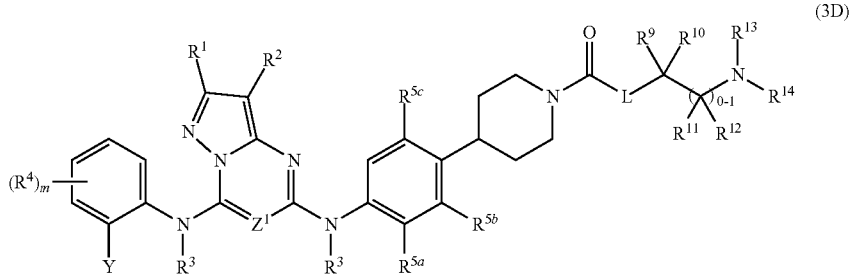

wherein $R^{5a}$, $R^{5b}$ and $R^{5c}$ are independently H, halo, hydroxyl, $C_{1-6}$ alkyl, $C_{1-6}$ alkoxy, halo-substituted $C_{1-6}$ alkyl or halo-substituted $C_{1-6}$ alkoxy;

$R^7$ is $(CR_2)_q$—W, or $C_{1-6}$ alkyl, $C_{2-6}$ alkenyl or $C_{2-6}$ alkynyl, each of which may be optionally substituted with halo, amino, hydroxyl, or alkoxy;

W is a 5-6 membered heterocyclic ring; and

R, $R^1$, $R^2$, $R^3$, $R^4$, $R^9$, $R^{10}$, $R^{11}$, $R^{12}$, $R^{13}$, $R^{14}$, L, q and m are as defined in Formula (1) or (2).

In another aspect, the invention provides a compound of Formula (4) or (5):

(4)

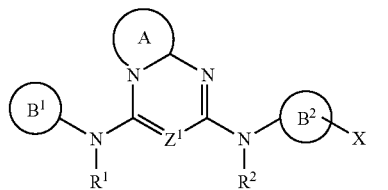

or (5)

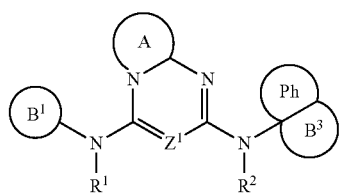

or a pharmaceutically acceptable salt thereof;

wherein A is a 5-6 membered heteroaryl containing 1-3 N heteroatoms, and optionally substituted with 1-2 $R^3$ groups;

$B^1$ and $B^2$ are independently aryl or heteroaryl, each of which is optionally substituted with 1-3 $R^4$ groups;

$B^3$ is a 5-6 membered ring optionally containing $NR^5$, O, =O or S, and is fused to a phenyl ring to form a fused 9-10 membered ring that is optionally substituted with 1-3 $R^3$ groups;

Ph is phenyl;

X is a $C_{3-12}$ carbocyclic ring, $C_{6-10}$ aryl; or a 5-10 membered heteroaryl or 4-10 membered heterocyclic ring optionally containing $NR^5$, O or S; each of which is optionally substituted with 1-3 $R^3$ groups; or X is a $C_{1-6}$ alkyl, $C_{2-6}$ alkenyl, $C_{2-6}$ alkynyl or $(CR_2)_{1-4}CO_2R^7$, each of which may be optionally substituted with halo, amino or hydroxyl;

$Z^1$ is N or CH;

$R^1$ and $R^2$ are independently H, $C(O)R^6$, $C_{1-6}$ alkyl or halo-substituted $C_{1-6}$ alkyl;

$R^3$ and $R^4$ are independently $C_{1-6}$ alkyl, $C_{1-6}$ alkoxy, $C_{2-6}$ alkenyl or $C_{2-6}$ alkynyl, each of which may be optionally substituted with halo, amino or hydroxyl groups; halo, nitro, cyano, $C(R)(OR^7)(R^7)$, $OR^7$, $NR(R^7)$, $C(R)(NRR^7)(R^7)$, $(CR_2)_qY$, $C(O)O_{0-1}R^7$, $C(O)NR(R^7)$, $C(O)CRR^7-NR(R^7)$, $C(O)NR(CR_2)_pNR(R^7)$, $C(O)NR(CR_2)_pOR^7$, $C(O)NR(CR_2)_p SR^7$, $C(O)NR(CR_2)_qS(O)_{1-2}R^8$, $S(O)_{0-2}R^8$, $(CR_2)_{1-6}NR(CR_2)_qOR^7$, $(CR_2)_{1-6}NR(CR_2)_qC(O)R^8$, $S(O)_2NRR^7$, $S(O)_2 NR(CR_2)_pNR(R^7)$, or $S(O)_2NR(CR_2)_pOR^7$;

$R^5$ is H, $C_{1-6}$ alkyl, $C_{2-6}$ alkenyl or $C_{2-6}$ alkynyl, each of which may be optionally substituted with halo, amino or hydroxyl groups; halo, nitro or cyano; $(CR_2)_p-OR^7$, $(CR_2)_p-NR(R^7)$, -L-Y, -L-C(O)-$R^7$, $-(CR_2)_{1-4}-C(O)O-R^7$, $-C(O)-(CR_2)_q-OR^7$, -L-C(O)-NRR$^7$, -L-CR(OR$^7$)-$C_tF_{(2t+1)}$ wherein t is 1-3; -L-C(O)-CR(R$^7$)-NRR$^7$, -L-C(O)-NR-$(CR_2)_p$-NRR$^7$, -L-C(O)NR(CR$_2)_p$OR$^7$, -L-C(O)-(CR$_2)_q$-NR-C(O)-R$^8$, -L-C(O)NR(CR$_2)_p$SR$^7$, -L-C(O)NR(CR$_2)_q$S(O)$_{1-2}$R$^8$, $(CR_2)_p$NR(CR$_2)_p$OR$^7$, $(CR_2)_p$NR-L-C(O)R$^8$, L-S(O)$_2$R$^8$, -L-S(O)$_2$NRR$^7$, -L-S(O)$_2$NR $(CR_2)_p$NR(R$^7$), -L-S(O)$_2$NR(CR$_2)_p$OR$^7$ or a radical selected from formula (a), (b) or (c):

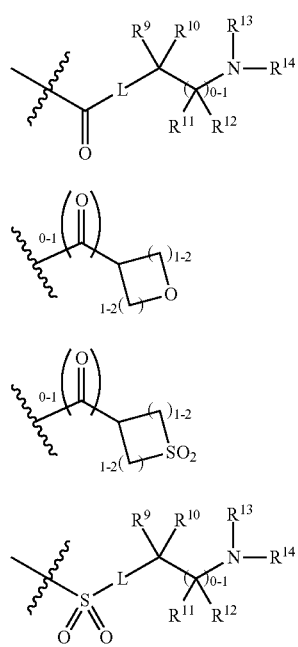

(a)

(b)

(c)

(d)

wherein $R^9$, $R^{10}$, $R^{11}$, $R^{12}$, $R^{13}$ and $R^{14}$ are independently selected from H, or $C_{1-6}$ alkyl, $C_{1-6}$ alkoxy, $C_{2-6}$ alkenyl or $C_{2-6}$ alkynyl, each of which may be optionally substituted with halo, amino, hydroxyl or alkoxy groups; or $R^9$ and $R^{10}$, $R^{10}$ and $R^{13}$, $R^{13}$ and $R^{14}$, $R^{11}$ and $R^{12}$, or $R^{11}$ and $R^{13}$ together with the carbon and/or nitrogen atoms to which they are attached may form a 3-7 membered saturated, unsaturated or partially unsaturated ring optionally containing up to 3 atoms or groups selected from C(O), N, O and S(O)$_{0-2}$ and optionally substituted with 1-3 $R^3$ groups;

L is $(CR_2)_{1-4}$ or a bond;

$R^6$, $R^7$ and $R^8$ are independently $(CR_2)_qY$, or $C_{1-6}$ alkyl, $C_{2-6}$ alkenyl or $C_{2-6}$ alkynyl, each of which may be optionally substituted with halo, amino or hydroxyl; or $R^7$ is H;

Y is a $C_{3-12}$ carbocyclic ring, $C_{6-10}$ aryl; or a 5-10 membered heteroaryl or 4-10 membered heterocyclic ring; each of which is optionally substituted with 1-3 $R^3$ groups;

each R is H or $C_{1-6}$ alkyl;
p is 2-4; and
q is 0-4;
provided $B^1$ is substituted with $S(O)_{0-2}R^8$, $SO_2NRR^7$ or $CONRR^7$ when $B^1$ is phenyl.

In some examples, the invention provides compounds having Formula (4) or (5), wherein $B^1$ and $B^2$ are phenyl; $B^1$ is substituted with $SO_2R^8$, $SO_2NRR^7$ or $CONRR^7$; and $R^{7a}$ and $R^8$ are $C_{1-6}$ alkyl.

In some embodiments, the invention provides compounds having Formula (5A), (5B) or (5C):

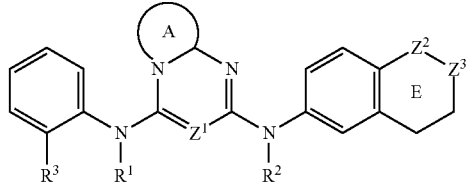

(5A)

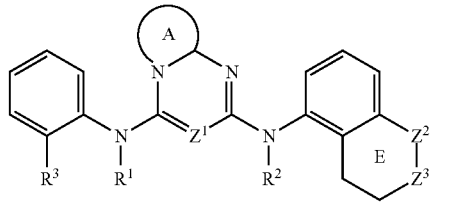

(5B)

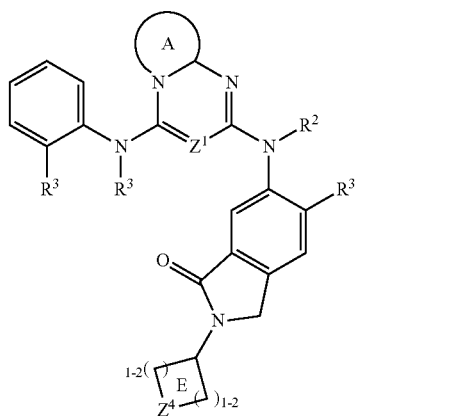

(5C)

wherein one of $Z^2$ and $Z^3$ is NR$^5$, O or S, and the other is CH$_2$;
$Z^4$ is NR$^5$, O or S;
ring E may optionally contain a double bond; and
$R^5$ is as defined in Formula (4) or (5).

In other embodiments, the invention provides compounds having Formula (6A) or (6B):

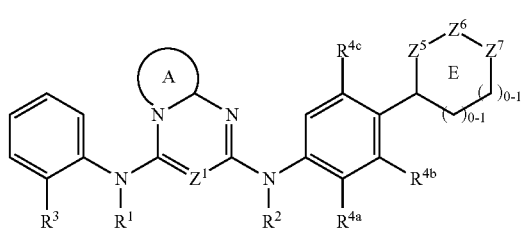

(6A)

-continued (6B)

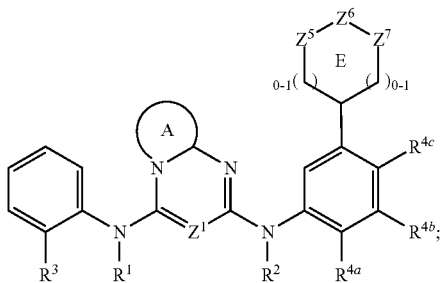

wherein $R^{4a}$, $R^{4b}$ and $R^{4c}$ are independently H, halo, hydroxyl, $C_{1-6}$ alkyl, $C_{1-6}$ alkoxy, halo-substituted $C_{1-6}$ alkyl or halo-substituted $C_{1-6}$ alkoxy;

one of $Z^5$, $Z^6$ and $Z^7$ is $NR^5$, O or S, and the others are $CH_2$; and $R^5$ is as defined in Formula (4) or (5).

In the above Formula (6A) or (6B), $Z^6$ is $NR^5$ or O; and $Z^5$ and $Z^7$ are $CH_2$. In other examples, $R^{4b}$ is H; and $R^{4a}$ and $R^{4c}$ are independently halo, hydroxyl, $C_{1-6}$ alkyl, $C_{1-6}$ alkoxy, halo-substituted $C_{1-6}$ alkyl or halo-substituted $C_{1-6}$ alkoxy.

In yet other embodiments, the invention provides compounds having Formula (7):

(7)

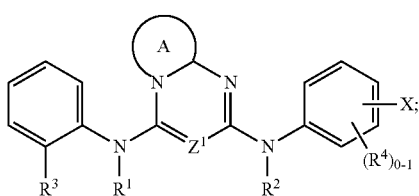

wherein X is a 5-6 membered heteroaryl or heterocyclic ring optionally containing $NR^5$, O or S; or X is a $C_{1-6}$ alkyl, $C_{2-6}$ alkenyl, $C_{2-6}$ alkynyl or $(CR_2)_{1-4}CO_2R^7$, each of which may be optionally substituted with halo, amino or hydroxyl; and $R^4$ if present is hydroxyl, $C_{1-6}$ alkyl, $C_{1-6}$ alkoxy, halo-substituted $C_{1-6}$ alkyl or halo-substituted $C_{1-6}$ alkoxy.

In the above Formula (4), (5), (5A), (5B), (5C), (6A), (6B) or (7), $R^1$ and $R^2$ may be H. In any of the above formula, ring A may be

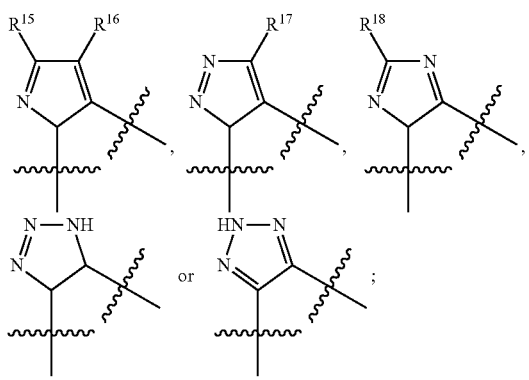

wherein $R^{15}$, $R^{16}$, $R^{17}$ and $R^{18}$ are independently H, $C_{1-6}$ alkyl, $C_{1-6}$ alkoxy, $C_{2-6}$ alkenyl or $C_{2-6}$ alkynyl, each of which may be optionally substituted with halo, amino or hydroxyl groups; halo, nitro, cyano or $(CR_2)_qY$; and Y is a $C_{3-12}$ carbocyclic ring, $C_{6-10}$ aryl; or a 5-10 membered heteroaryl or 4-10 membered heterocyclic ring.

In each of the above formula, any asymmetric carbon atoms may be present in the (R)-, (S)- or (R,S)-configuration. The compounds may thus be present as mixtures of isomers or as pure isomers, for example, as pure enantiomers or diastereomers. The invention further encompasses possible tautomers of the inventive compounds.

The present invention also includes all suitable isotopic variations of the compounds of the invention, or pharmaceutically acceptable salts thereof. An isotopic variation of a compound of the invention or a pharmaceutically acceptable salt thereof is defined as one in which at least one atom is replaced by an atom having the same atomic number but an atomic mass different from the atomic mass usually found in nature. Examples of isotopes that may be incorporated into the compounds of the invention and pharmaceutically acceptable salts thereof include but are not limited to isotopes of hydrogen, carbon, nitrogen and oxygen such as $^2H$, $^3H$, $^{11}C$, $^{13}C$, $^{14}C$, $^{15}N$, $^{17}O$, $^{18}O$, $^{35}S$, $^{18}F$, $^{36}Cl$ and $^{123}I$. Certain isotopic variations of the compounds of the invention and pharmaceutically acceptable salts thereof, for example, those in which a radioactive isotope such as $^3H$ or $^{14}C$ is incorporated, are useful in drug and/or substrate tissue distribution studies.

In particular examples, $^2H$, $^3H$ and $^{14}C$ isotopes may be used for their ease of preparation and detectability. In other examples, substitution with isotopes such as $^2H$ may afford certain therapeutic advantages resulting from greater metabolic stability, such as increased in vivo half-life or reduced dosage requirements. Isotopic variations of the compounds of the invention or pharmaceutically acceptable salts thereof can generally be prepared by conventional procedures using appropriate isotopic variations of suitable reagents. Isotopic variations of the compounds have the potential to change a compound's metabolic fate and/or create small changes in physical properties such as hydrophobicity, and the like. Isotopic variation have the potential to enhance efficacy and safety, enhance bioavailability and half-life, alter protein binding, change biodistribution, increase the proportion of active metabolites and/or decrease the formation of reactive or toxic metabolites.

In each of the above formula, each optionally substituted moiety may be substituted with $C_{1-6}$ alkyl, $C_{2-6}$ alkenyl or $C_{3-6}$ alkynyl, each of which may be optionally halogenated or optionally having a carbon that may be replaced or substituted with N, S, O, or a combination thereof (for example, hydroxyl $C_1$-$C_8$ alkyl, $C_1$-$C_8$ alkoxy $C_1$-$C_8$ alkyl); halo, amino, amidino, $C_{1-6}$ alkoxy; hydroxyl, methylenedioxy, carboxy; $C_{1-8}$ alkylcarbonyl, $C_{1-8}$ alkoxycarbonyl, carbamoyl, $C_{1-8}$ alkylcarbamoyl, sulfamoyl, cyano, oxo, nitro, or an optionally substituted carbocyclic ring, heterocyclic ring, aryl or heteroaryl as previously described.

Pharmacology and Utility

The compounds of the invention and their pharmaceutically acceptable salts exhibit valuable pharmacological properties when tested in vitro in cell-free kinase assays and in cellular assays, and are therefore useful as pharmaceuticals.

In one aspect, compounds of Formula (1), (2), (2A-2C), (3A-3D), (4), (5), (5A-5C), (6A-6B) or (7) may inhibit the tyrosine kinase activity of anaplastic lymphoma kinase (ALK) and the fusion protein of NPM-ALK. This protein tyrosine kinase results from a gene fusion of nucleophosmin (NPM) and ALK, rendering the protein tyrosine kinase activity of ALK ligand independent. NPM-ALK plays a key role in signal transmission in a number of hematopoetic and other human cells leading to hematological and neoplastic diseases, for example in anaplastic large-cell lymphoma (ALCL) and non-Hodgkin's lymphomas (NHL), specifically in ALK+NHL or Alkomas, in inflammatory myofibroblastic tumors (IMT) and neuroblastomas. (Duyster et al. 2001 Oncogene 20, 5623-5637). In addition to NPM-ALK, other gene fusions have been identified in human hematological and neoplastic diseases; for example, TPM3-ALK (a fusion of nonmuscle tropomyosin with ALK).

The inhibition of ALK tyrosine kinase activity may be demonstrated using known methods, for example using the recombinant kinase domain of the ALK in analogy to the VEGF-R kinase assay described in J. Wood et al. Cancer Res. 60, 2178-2189 (2000). In general, in vitro enzyme assays using GST-ALK protein tyrosine kinase are performed in 96-well plates as a filter binding assay in 20 mM Tris HCl, pH=7.5, 3 mM $MgCl_2$, 10 mM $MnCl_2$, 1 mM DTT, 0.1 µCi/assay (=30 µl) [$\gamma$-$^{33}$P]-ATP, 2 µM ATP, 3 µg/mL poly (Glu, Tyr 4:1) Poly-EY (Sigma P-0275), 1% DMSO, 25 ng ALK enzyme. Assays are incubated for 10 min at ambient temperature. Reactions are terminated by adding 50 µl of 125 mM EDTA, and the reaction mixture is transferred onto a MAIP Multiscreen plate (Millipore, Bedford, Mass., USA), previously wet with methanol, and rehydrated for 5 min with $H_2O$. Following washing (0.5% $H_3PO_4$), plates are counted in a liquid scintillation counter. $IC_{50}$ values are calculated by linear regression analysis of the percentage inhibition.

Compounds of Formula (1), (2), (2A-2C), (3A-3D), (4), (5), (5A-5C), (6A-6B) or (7) may potently inhibit the growth of human NPM-ALK overexpressing murine BaF3 cells (DSMZ Deutsche Sammiung von Mikroorganismen and Zelikulturen GmbH, Germany). The expression of NPM-ALK may be achieved by transfecting the BaF3 cell line with an expression vector pClneo™ (Promega Corp., Madison Wis., USA) coding for NPM-ALK and subsequent selection of G418 resistant cells. Non-transfected BaF3 cells depend on IL-3 for cell survival. In contrast, NPM-ALK expressing BaF3 cells (named BaF3-NPM-ALK hereinafter) can proliferate in the absence of IL-3 because they obtain proliferative signal through NPM-ALK kinase. Putative inhibitors of the NPM-ALK kinase therefore abolish the growth signal and may result in antiproliferative activity. The antiproliferative activity of putative inhibitors of the NPM-ALK kinase can however be overcome by addition of IL-3, which provides growth signals through an NPM-ALK independent mechanism. An analogous cell system using FLT3 kinase has also been described (see, E Weisberg et al. Cancer Cell; 1, 433-443 (2002)).

The inhibitory activity of the compounds of the invention may be determined as follows. In general, BaF3-NPM-ALK cells (15,000/microtitre plate well) are transferred to 96-well microtitre plates. Test compounds dissolved in dimethyl sulfoxide (DMSO) are added in a series of concentrations (dilution series) in such a manner that the final concentration of DMSO is not greater than 1% (v/v). After the addition, the plates are incubated for two days during which the control cultures without test compound are able to undergo two cell-division cycles. The growth of the BaF3-NPM-ALK cells is measured by means of YOPRO™ staining [T Idziorek et al. J. Immunol. Methods; 185: 249-258 (1995)]: 25 µl of lysis buffer comprising 20 mM sodium citrate, pH 4.0, 26.8 mM sodium chloride, 0.4% NP40, 20 mM EDTA and 20 mM is added to each well. Cell lysis is completed within 60 min at room temperature and total amount of YOPRO™ bound to DNA is determined by measurement using the Cytofluor II 96-well reader (PerSeptive Biosystems) with the following settings: Excitation (nm) 485/20 and Emission (nm) 530/25.

$IC_{50}$ values may be determined by a computer-aided system using the formula:

$$IC_{50}=[(ABS_{test}-ABS_{start})/(ABS_{control}-ABS_{start})]\times 100 \cdot (ABS=absorption)$$

The $IC_{50}$ value in those experiments is given as that concentration of the test compound in question that results in a cell count that is 50% lower than that obtained using the control without inhibitor. The compounds of the invention in free form or in pharmaceutically acceptable salt form, may exhibit valuable pharmacological properties, for example, as indicated by the in vitro tests described in this application. In general, compounds of the invention have $IC_{50}$ values from 1 nM to 10 µM. In some examples, compounds of the invention have $IC_{50}$ values from 0.01 µM to 5 µM. In other examples, compounds of the invention have $IC_{50}$ values from 0.01 µM to 1 µM, or more particularly from 1 nM to 1 µM. In yet other examples, compounds of the invention have $IC_{50}$ values of less than 1 nM or more than 10 µM. The compounds of the invention may exhibit a percentage inhibition of greater than 50%, or in other embodiments, may exhibit a percentage inhibition greater than about 70%, against ALK at 10 µM.

The antiproliferative action of the inventive compounds may also be determined in the human KARPAS-299 lymphoma cell line (DSMZ Deutsche Sammiung von Mikroorganismen and Zelikulturen GmbH, Braunschweig, Germany, described in W G Dirks et al. Int. J. Cancer 100, 49-56 (2002)) using the same methodology described above for the BaF3-NPM-ALK cell line. In some embodiments, compounds of the invention may exhibit inhibitory activity with an $IC_{50}$ in the range from approximately 0.01 to 1 µM. The action of the inventive compounds on autophosphorylation of the ALK may be determined in the human KARPAS-299 lymphoma cell line by means of an immunoblot as described in W G Dirks et al. Int. J. Cancer 100, 49-56 (2002).

The compounds of the invention may also inhibit insulin like growth-factor receptor 1 (IGF-1R), and may be useful in the treatment of IGF-1 R mediated diseases. Examples of IGF-1R mediated diseases include but are not limited to proliferative diseases, such as tumors, for example breast, renal, prostate, colorectal, thyroid, ovarian, pancreas, neuronal, lung, uterine and gastro intestinal tumors, as well as osteosarcomas and melanomas. The efficacy of the compounds of the invention as inhibitors of IGF-1R tyrosine kinase activity may be demonstrated using a cellular capture ELISA. In this assay, the activity of the compounds of the invention against (IGF-1)-induced autophosphorylation of the IGF-1R is determined The compounds of the invention may also be useful in the treatment and/or prevention of acute or chronic inflammatory diseases or disorders or autoimmune diseases e.g. rheumatoid arthritis, osteoarthritis, systemic lupus erythematosus, Hashimoto's thyroiditis, multiple sclerosis, myasthenia gravis, diabetes (type I and II) and the disorders associated therewith, respiratory diseases such as asthma or inflammatory liver injury, inflammatory glomerular injury, cutaneous manifestations of immunologically-mediated disorders or illnesses, inflammatory and hyperproliferative skin diseases (such as psoriasis, atopic dermatitis, allergic contact dermatitis, irritant contact dermatitis and further eczematous dermatitis, seborrhoeic dermatitis), s inflammatory eye diseases, e.g. Sjoegren's syndrome, keratoconjunctivitis or uveitis, inflammatory bowel disease, Crohn's disease or ulcerative colitis.

In accordance with the foregoing, the present invention provides:

(1) a compound of the invention for use as a pharmaceutical;

(2) a compound of the invention for use as an ALK inhibitor, Ros inhibitor, IGF-1R and/or InsR inhibitor, for example for use in any of the particular indications hereinbefore set forth;

(3) a pharmaceutical composition, e.g. for use in any of the indications herein before set forth, comprising a compound of the invention as active ingredient together with one or more pharmaceutically acceptable diluents or carriers;

(4) a method for the treatment of any particular indication set forth hereinbefore in a subject in need thereof which comprises administering an effective amount of a compound of the invention or a pharmaceutical composition comprising same;

(5) the use of a compound of the invention for the manufacture of a medicament for the treatment or prevention of a disease or condition in which ALK, Ros, IGF-1R and/or InsR activation plays a role or is implicated;

(6) the method as defined above under (4) comprising co-administration, e.g. concomitantly or in sequence, of a therapeutically effective amount of a compound of the invention and one or more further drug substances, said further drug substance being useful in any of the particular indications set forth hereinbefore;

(7) a combination comprising a therapeutically effective amount of a compound of the invention and one or more further drug substances, said further drug substance being useful in any of the particular indications set forth hereinbefore;

(8) use of a compound of the invention for the manufacture of a medicament for the treatment or prevention of a disease which responds to inhibition of the anaplastic lymphoma kinase;

(9) the use according to (8), wherein the disease to be treated is selected from anaplastic large cell lymphoma, non-Hodgkin's lymphomas, inflammatory myofibroblastic tumors, neuroblastomas and neoplastic diseases;

(10) the use according to (8) or (9), wherein the compound is or a pharmaceutically acceptable; salt of any one of the examples;

(11) a method for the treatment of a disease which responds to inhibition of the anaplastic lymphoma kinase, especially a disease selected from anaplastic large-cell lymphoma, non Hodgkin's lymphomas, inflammatory myofibroblastic tumors, neuroblastomas and neoplastic diseases, comprising administering an effective amount of a compound of the invention or a pharmaceutically acceptable salt thereof.

Administration and Pharmaceutical Compositions

A pharmaceutical composition, as used herein, refers to a mixture of a compound of the invention with other chemical components, such as carriers, stabilizers, diluents, dispersing agents, suspending agents, thickening agents, and/or excipients. The pharmaceutical composition facilitates administration of the compound to an organism. Pharmaceutical compositions containing a compound of the invention may be administered in therapeutically effective amounts as pharmaceutical compositions by any conventional form and route known in the art including, but not limited to: intravenous, oral, rectal, aerosol, parenteral, ophthalmic, pulmonary, transdermal, vaginal, otic, nasal, and topical administration.

One may administer the compound in a local rather than systemic manner, for example, via injection of the compound directly into an organ, often in a depot or sustained release formulation. Furthermore, one may administer pharmaceutical composition containing a compound of the invention in a targeted drug delivery system, for example, in a liposome coated with organ-specific antibody. The liposomes will be targeted to and taken up selectively by the organ. In addition, pharmaceutical compositions containing a compound of the invention may be provided in the form of a rapid release formulation, in the form of an extended release formulation, or in the form of an intermediate release formulation.

For oral administration, a compound of the invention may be formulated readily by combining the active compounds with pharmaceutically acceptable carriers or excipients well known in the art. Such carriers enable the compounds described herein to be formulated as tablets, powders, pills, dragees, capsules, liquids, gels, syrups, elixirs, slurries, suspensions and the like, for oral ingestion by a patient to be treated.

Pharmaceutical preparations for oral use may be obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross-linked croscarmellose sodium, polyvinylpyrrolidone, agar, or alginic acid or a salt thereof such as sodium alginate.

Dragee cores may be provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which may be used orally include push-fit capsules made of gelatin, as well as soft, sealed capsules made of gelatin and a plasticizer, such as glycerol or sorbitol. The push-fit capsules may contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

For buccal or sublingual administration, the compositions may take the form of tablets, lozenges, or gels formulated in conventional manner. Parental injections may involve bolus injection or continuous infusion. The pharmaceutical composition of a compound of the invention may be in a form suitable for parenteral injection as a sterile suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

The compounds of the invention may be administered topically and may be formulated into a variety of topically administrable compositions, such as solutions, suspensions, lotions, gels, pastes, medicated sticks, balms, creams or ointments. Such pharmaceutical compounds may contain solubilizers, stabilizers, tonicity enhancing agents, buffers and preservatives.

Formulations suitable for transdermal administration may employ transdermal delivery devices and transdermal delivery patches, and may be lipophilic emulsions or buffered, aqueous solutions, dissolved and/or dispersed in a polymer or an adhesive. Such patches may be constructed for continuous, pulsatile, or on demand delivery of pharmaceutical agents. Still further, transdermal delivery of the compounds of the invention may be accomplished by means of iontophoretic patches and the like. Additionally, transdermal patches may provide controlled delivery of the compounds of the invention. The rate of absorption may be slowed by using rate-controlling membranes or by trapping the compound within a polymer matrix or gel. Conversely, absorption enhancers may be used to increase absorption. An absorption enhancer or carrier may include absorbable pharmaceutically acceptable solvents to assist passage through the skin. For example, transdermal devices are in the form of a bandage comprising a backing member, a reservoir containing the compound optionally with carriers, optionally a rate controlling bather to deliver the compound to the skin of the host at a controlled and predetermined rate over a prolonged period of time, and means to secure the device to the skin.

For administration by inhalation, the compounds of the invention may be in a form as an aerosol, a mist or a powder. Pharmaceutical compositions of the compounds of the invention may be conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges, such as, by way of example only, gelatin for use in an inhaler or insufflator may be formulated containing a powder mix of the compound and a suitable powder base such as lactose or starch.

The compounds of the invention may also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

Pharmaceutical compositions may be formulated in conventional manner using one or more physiologically acceptable carriers comprising excipients and auxiliaries which facilitate processing of the active compounds into preparations which may be used pharmaceutically. Proper formulation is dependent upon the route of administration chosen. Any of the well-known techniques, carriers, and excipients may be used as suitable and as understood in the art. Pharmaceutical compositions comprising a compound of the invention may be manufactured in a conventional manner, such as, by way of example only, by means of conventional mixing, dissolving, granulating, dragee-making, levigating, emulsifying, encapsulating, entrapping or compression processes.

The pharmaceutical compositions will include at least one pharmaceutically acceptable carrier, diluent or excipient and a compound of Formula (1), (2A-2C), (3A-3D), (4), (5), (5A-5C), (6A-6B) or (7) described herein as an active ingredient in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. In some situations, compounds may exist as tautomers. All tautomers are included within the scope of the compounds presented herein. Additionally, the compounds described herein may exist in unsolvated as well as solvated forms with pharmaceutically acceptable solvents such as water, ethanol, and the like. The solvated forms of the compounds presented herein are also considered to be disclosed herein. In addition, the pharmaceutical compositions may include other medicinal or pharmaceutical agents, carriers, adjuvants, such as preserving, stabilizing, wetting or emulsifying agents, solution promoters, salts for regulating the osmotic pressure, and/or buffers. In addition, the pharmaceutical compositions may also contain other therapeutically valuable substances.

Methods for the preparation of compositions comprising the compounds described herein include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. The compositions may be in liquid solutions or suspensions, solid forms suitable for solution or suspension in a liquid prior to use, or as emulsions. These compositions may also contain minor amounts of nontoxic, auxiliary substances, such as wetting or emulsifying agents, pH buffering agents, and so forth.

A summary of pharmaceutical compositions described herein may be found, for example, in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and* Drug Delivery Systems, Seventh Ed. (Lippincott Williams & Wilkins 1999), herein incorporated by reference in their entirety.

Methods of Administration and Treatment Methods

The compositions containing the compound(s) described herein may be administered for prophylactic and/or therapeutic treatments. In therapeutic applications, the compositions are administered to a patient already suffering from a disease or condition, in an amount sufficient to cure or at least partially arrest the symptoms of the disease or condition. It is considered well within the skill of the art for one to determine such therapeutically effective amounts by routine experimentation (including, but not limited to, a dose escalation clinical trial).

The compounds of the invention may be administered as the sole active ingredient, or in combination with a second therapeutic agent. For example, the compounds of the invention may be administered together with other therapeutic agents against neoplastic diseases, with agents useful in immunomodulating regimens or with pharmaceutical compositions effective in various diseases as described above, e.g. cyclophosphamide, 5-fluorouracil, fludarabine, gemcitabine, cisplatinum, carboplatin, vincristine, vinblastine, etoposide, irinotecan, paclitaxel, docetaxel, rituxan, doxorubicine, gefitinib, or imatinib; or also with cyclosporins, rapamycins, ascomycins or their immunosuppressive analogs, e.g. cyclosporin A, cyclosporin G, FK-506, sirolimus or everolimus, corticosteroids, e.g. prednisone, cyclophosphamide, azathioprene, methotrexate, gold salts, sulfasalazine, antimalarials, brequinar, leflunomide, mizoribine, mycophenolic acid, mycophenolate, mofetil, 15-deoxyspergualine, immuno-suppressive monoclonal antibodies, e.g. monoclonal antibodies to leukocyte receptors, e.g. MHC, CD2, CD3, CD4, CD7, CD25, CD28, ICD40, CD45, CD58, CD80, CD86, CD152, CD137, CD154, ICOS, LFA-1, VLA-4 or their ligands, or other immunomodulatory compounds, e.g. CTLA41g.

The compounds of the invention may also be used in combination with a chemotherapeutic agent to treat a cell proliferative disorder, including but not limited to, lymphoma, osteosarcoma, melanoma, or a tumor of breast, renal, prostate, colorectal, thyroid, ovarian, pancreatic, neuronal, lung, uterine or gastrointestinal tumor. Examples of chemotherapeutic agents which may be used in the compositions and methods of the invention include but are not limited to anthracyclines, alkylating agents (e.g., mitomycin C), alkyl sulfonates, aziridines, ethylenimines, methylmelamines, nitrogen mustards, nitrosoureas, antibiotics, antimetabolites, folic acid analogs (e.g., dihydrofolate reductase inhibitors such as methotrexate), purine analogs, pyrimidine analogs, enzymes, podophyllotoxins, platinum-containing agents, interferons, and interleukins. Particular examples of known chemotherapeutic agents which may be used in the compositions and methods of the invention include, but are not limited to, busulfan, improsulfan, piposulfan, benzodepa, carboquone, meturedepa, uredepa, altretamine, triethylenemelamine, triethylenephosphoramide, triethylenethiophosphoramide, trimethylolomelamine, chlorambucil, chlornaphazine, cyclophosphamide, estramustine, ifosfamide, mechlorethamine, mechlorethamine oxide hydrochloride, melphalan, novembichin, phenesterine, prednimustine, trofosfamide, uracil mustard, carmustine, chlorozotocin, fotemustine, lomustine, nimustine, ranimustine, dacarbazine, mannomustine, mitobronitol, mitolactol, pipobroman, aclacinomycins, actinomycin F(1), anthramycin, azaserine, bleomycin, cactinomycin, carubicin, carzinophilin, chromomycin, dactinomycin, daunorubicin, daunomycin, 6-diazo-5-oxo-1-norleucine, doxorubicin, epirubicin, mitomycin C, mycophenolic acid, nogalamycin, olivomycin, peplomycin, plicamycin, porfiromycin, puromycin, streptonigrin, streptozocin, tubercidin, ubenimex, zinostatin, zorubicin, denopterin, methotrexate, pteropterin, trimetrexate, fludarabine, 6-mercaptopurine, thiamiprine, thioguanine, ancitabine, azacitidine, 6-azauridine, carmofur, cytarabine, dideoxyuridine, doxifluridine, enocitabine, floxuridine, fluorouracil, tegafur, L-asparaginase, pulmozyme, aceglatone, aldophosphamide glycoside, aminolevulinic acid, amsacrine, bestrabucil, bisantrene, carboplatin, cisplatin, defofamide, demecolcine, diaziquone, elfornithine, elliptinium acetate, etoglucid, etoposide, flutamide, gallium nitrate, hydroxyurea, interferon-alpha, interferon-beta, interferon-gamma, interleukin-2, lentinan, lonidamine, mitoguazone, mitoxantrone, mopidamol, nitracrine, pentostatin, phenamet, pirarubicin, podophyllinic acid, 2-ethylhydrazide, procarbazine, razoxane, sizofiran, spirogermanium, paclitaxel, tamoxifen, teniposide, tenuazonic acid, triaziquone, 2,2',2"-trichlorotriethylamine, urethane, vinblastine, vincristine, and vindesine.

When the compounds of the invention are administered in conjunction with other therapies, dosages of the co-administered compounds will vary depending on the type of co-drug employed, on the specific drug employed, on the disease or condition being treated and so forth. In addition, when co-administered with one or more biologically active agents, the compounds of the invention may be administered either simultaneously with the biologically active agent(s), or sequentially. The administration of a compound of the invention in combination with a second therapeutic agent may have an additive or synergistic effect.

In general, compounds of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

Toxicity and therapeutic efficacy of such therapeutic regimens may be determined by standard pharmaceutical procedures in cell cultures or experimental animals, including, but not limited to, for determining the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. The data obtained from cell culture assays and animal studies may be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized.

Processes for Making Compounds of the Invention

General procedures for preparing compounds of the invention are described in the Examples, infra. In the reactions described, reactive functional groups, for example hydroxy, amino, imino, thio or carboxy groups, where these are desired in the final product, may be protected to avoid their unwanted participation in the reactions. Conventional protecting groups may be used in accordance with standard practice (see e.g., T. W. Greene and P. G. M. Wuts in "Protective Groups in Organic Chemistry", John Wiley and Sons, 1991).

In some examples, compounds having Formula (1) may be prepared following the synthetic procedures described in Scheme 1:

Scheme 1

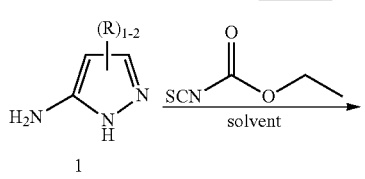

1

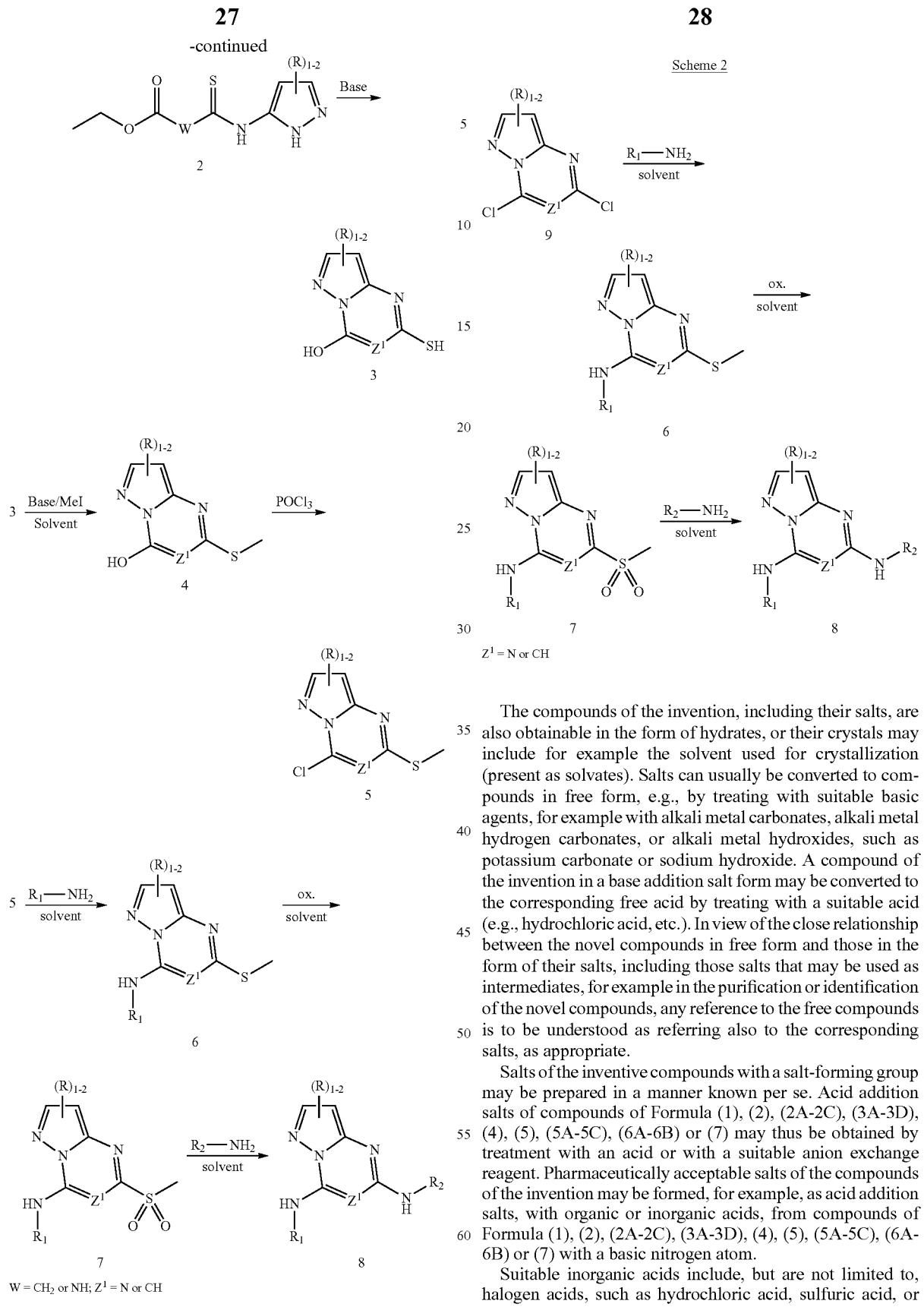

Alternatively, compounds of Formula (1) may be preparing following the synthetic procedures described in Scheme 2.

The compounds of the invention, including their salts, are also obtainable in the form of hydrates, or their crystals may include for example the solvent used for crystallization (present as solvates). Salts can usually be converted to compounds in free form, e.g., by treating with suitable basic agents, for example with alkali metal carbonates, alkali metal hydrogen carbonates, or alkali metal hydroxides, such as potassium carbonate or sodium hydroxide. A compound of the invention in a base addition salt form may be converted to the corresponding free acid by treating with a suitable acid (e.g., hydrochloric acid, etc.). In view of the close relationship between the novel compounds in free form and those in the form of their salts, including those salts that may be used as intermediates, for example in the purification or identification of the novel compounds, any reference to the free compounds is to be understood as referring also to the corresponding salts, as appropriate.

Salts of the inventive compounds with a salt-forming group may be prepared in a manner known per se. Acid addition salts of compounds of Formula (1), (2), (2A-2C), (3A-3D), (4), (5), (5A-5C), (6A-6B) or (7) may thus be obtained by treatment with an acid or with a suitable anion exchange reagent. Pharmaceutically acceptable salts of the compounds of the invention may be formed, for example, as acid addition salts, with organic or inorganic acids, from compounds of Formula (1), (2), (2A-2C), (3A-3D), (4), (5), (5A-5C), (6A-6B) or (7) with a basic nitrogen atom.

Suitable inorganic acids include, but are not limited to, halogen acids, such as hydrochloric acid, sulfuric acid, or phosphoric acid. Suitable organic acids include, but are not limited to, carboxylic, phosphoric, sulfonic or sulfamic acids, for example acetic acid, propionic acid, octanoic acid, decanoic acid, dodecanoic acid, glycolic acid, lactic acid, fumaric acid, succinic acid, adipic acid, pimelic acid, suberic acid, azelaic acid, -malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4 aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 2-naphthalenesulfonic acid, 1,5-naphthalene-disuifonic acid, 2-, 3- or 4 methylbenzenesulfonic acid, methylsulfuric acid, ethylsulfuric acid, dodecylsulfuric acid, N cyclohexylsulfamic acid, N-methyl-, N-ethyl- or N-propyl-sulfamic acid, or other organic protonic acids, such as ascorbic acid. For isolation or purification purposes, it is also possible to use pharmaceutically unacceptable salts, for example picrates or perchlorates. For therapeutic use, only pharmaceutically acceptable salts or free compounds are employed (where applicable in the form of pharmaceutical preparations).

Compounds of the invention in unoxidized form may be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention may be prepared by methods known to those of ordinary skill in the art (e.g., for further details see Saulnier et al., (1994), Bioorganic and Medicinal Chemistry Letters, Vol. 4, p. 1985). For example, appropriate prodrugs may be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention may be made by means known to those of ordinary skill in the art. A detailed description of techniques applicable to the creation of protecting groups and their removal may be found in T. W. Greene, "Protecting Groups in Organic Chemistry", 3$^{rd}$ edition, John Wiley and Sons, Inc., 1999.

Compounds of the invention may be prepared as their individual stereoisomers by reacting a racemic mixture of the compound with an optically active resolving agent to form a pair of diastereoisomeric compounds, separating the diastereomers and recovering the optically pure enantiomers. Resolution of enantiomers may be carried out using covalent diastereomeric derivatives of the compounds of the invention, or by using dissociable complexes (e.g., crystalline diastereomeric salts). Diastereomers have distinct physical properties (e.g., melting points, boiling points, solubilities, reactivity, etc.) and may be readily separated by taking advantage of these dissimilarities. The diastereomers may be separated by fractionated crystallization, chromatography, or by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture may be found in Jean Jacques, Andre Collet, Samuel H. Wilen, "Enantiomers, Racemates and Resolutions", John Wiley And Sons, Inc., 1981.

In summary, the compounds of the invention may be made by a process as described in the Examples; and (a) optionally converting a compound of the invention into a pharmaceutically acceptable salt;

(b) optionally converting a salt form of a compound of the invention to a non-salt form;

(c) optionally converting an unoxidized form of a compound of the invention into a pharmaceutically acceptable N-oxide;

(d) optionally converting an N-oxide form of a compound of the invention to its unoxidized form;

(e) optionally resolving an individual isomer of a compound of the invention from a mixture of isomers;

(f) optionally converting a non-derivatized compound of the invention into a pharmaceutically acceptable prodrug derivative; and (g) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter. One of skill in the art will appreciate that the above transformations are only representative of methods for preparation of the compounds of the present invention, and that other well known methods can similarly be used. The present invention is further exemplified, but not limited, by the following and Examples that illustrate the preparation of the compounds of the invention.

Example 1

N2-(2-isopropoxy-5-methyl-4-(1-methylpiperidin-4-yl)phenyl)-N4-(2-(isopropylsulfonyl)phenyl)pyrazolo[1,5-a][1,3,5]triazine-2,4-diamine (1)

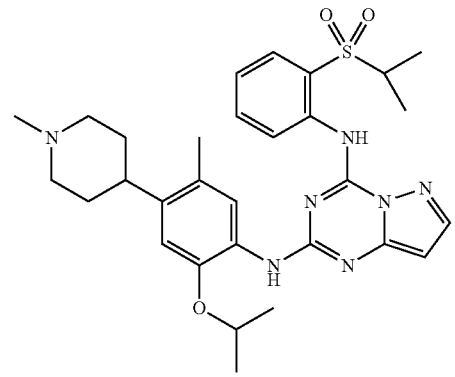 [SMILES: Cc1cc(Nc2nc(Nc3ccccc3S(=O)(=O)C(C)C)n3nccc3n2)c(OC(C)C)cc1C1CCN(C)CC1]

2-(methylthio)pyrazolo[1,5-a][1,3,5]triazin-4-ol

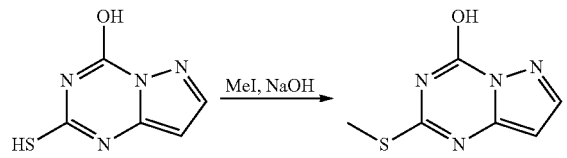

Seven grams of 2-mercaptopyrazolo[1,5-a][1,3,5]triazin-4-ol (prepared according to the method described in *Chemische Berichte*, 1971, 104:3039-47) was dissolved in 5% aqueous NaOH (100 mL). The solution was cooled to 5° C. (ice bath) and 6 g. of methyl iodide was added dropwise. After 15-20 minutes, charcoal was added and the mixture was filtered then acidified with acetic acid. The precipitate (2-(methylthio)pyrazolo[1,5-a][1,3,5]triazin-4-ol was filtered, dried and isolated. Further recrystallization in AcOH gave 2-(methylthio)pyrazolo[1,5-a][1,3,5]triazin-4-ol. MS (ES+): 183.0 (M+1)+.

4-chloro-2-(methylthio)pyrazolo[1,5-a][1,3,5]triazine

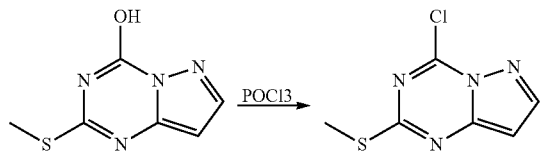

To a mixture of 10 mL of phosphorus oxychloride and 1 mL of N,N-dimethylaniline was added 0.5 g of 2-(methylthio)pyrazolo[1,5-a][1,3,5]triazin-4-ol (crude from previous step). The solution was refluxed for 30-60 minutes until all the solid dissolved. The excess phosphorus was removed under reduced pressure and the syrupy residue poured with vigorous stirring onto a mixture of ice water. After 10 minutes, the aqueous solution was extracted with ether. The ethereal layers were collected and washed with cold water, then dried with anhydrous Na₂SO₄. Filtration and concentration under reduced pressure gave the desired 4-chloro-2-(methylthio)pyrazolo[1,5-a][1,3,5]triazine. MS (ES+): 201.0 (M+1)+.

N-(2-(isopropylsulfonyl)phenyl)-2-(methylthio)pyrazolo[1,5-a][1,3,5]triazin-4-amine

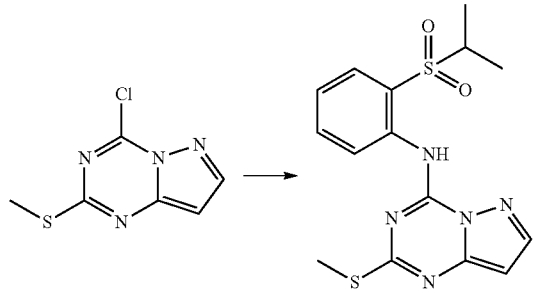 [SMILES: CSc1nc(Cl)n2nccc2n1 ; CSc1nc(Nc2ccccc2S(=O)(=O)C(C)C)n2nccc2n1]

A solution of 4-chloro-2-(methylthio)pyrazolo[1,5-a][1,3,5]triazine (10 mmol) and 2-(N,N-dimethylsulfonyl)aniline (10 mmol) in 100 mL of iso-propanol was stirred at reflux for 1 hour. After cooling to room temperature, Et₃N (12 mmol) was added to the reaction mixture, then the solution was heated under reflux for 30 minutes. After workup, the residue was purified over SiO₂ flash column chromatography (eluent: hexane/EtOAc 4:1) to give the desired N-(2-(isopropylsulfonyl)phenyl)-2-(methylthio)pyrazolo[1,5-a][1,3,5]triazin-4-amine. MS (ES+): 364.08 (M+1)+.

N-(2-(isopropylsulfonyl)phenyl)-2-(methysulfonyl)pyrazolo[1,5-a][1,3,5]triazin-4-amine

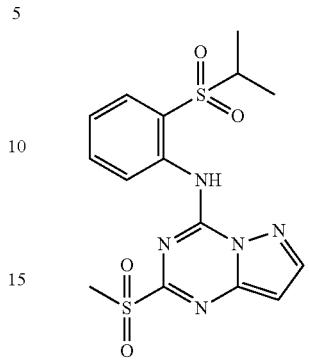

To a solution of N-(2-(isopropylsulfonyl)phenyl)-2-(methylthio)pyrazolo[1,5-a][1,3,5]triazin-4-amine (1 mmol) in 10 mL of 1,2-dicholoroethane, was slowly added MCPBA (3 mmol) at 0° C. The reaction mixture was progressively warmed to RT and stirred for 1 hour. After workup, the residue was purified over SiO₂ flash column chromatography (eluent: CH₂Cl₂/MeOH 9:1) to give N-(2-(isopropylsulfonyl)phenyl)-2-(methysulfonyl)pyrazolo[1,5-a][1,3,5]triazin-4-amine. MS (ES+): 396.07 (M+1)+.

N2-(2-isopropoxy-5-methyl-4-(1-methylpiperidin-4-yl)phenyl)-N4-(2-(isopropylsulfonyl)phenyl)pyrazolo[1,5-a][1,3,5]triazine-2,4-diamine

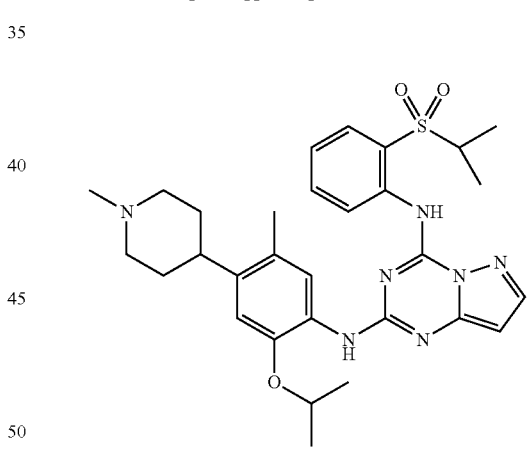

To a suspension of N-(2-(isopropylsulfonyl)phenyl)-2-(methysulfonyl)pyrazolo[1,5-a][1,3,5]triazin-4-amine (0.5 mmol) in 1 mL of isopropanol, was added 2-isopropoxy-5-methyl-4-(1-methylpiperidin-4-yl)aniline (0.5 mmol) and 4-methylbenzenesulfonic acid (1 mmol). The suspension was stirred at 150° C. for 3 hours. After cooling at RT and workup, the residue was purified using a preparative HPLC to afford N2-(2-isopropoxy-5-methyl-4-(1-methylpiperidin-4-yl)phenyl)-N4-(2-(isopropylsulfonyl)phenyl)pyrazolo[1,5-a][1,3,5]triazine-2,4-diamine. ¹H NMR (MeOD, 400 MHz) δ 8.51-8.54 (d, 1H), 7.94-8.04 (m, 2H), 7.35-7.47 (m, 3H), 6.90 (s, 1H), 6.34-6.35 (d, 1H), 4.54-4.60 (m. 1H), 3.82-3.85 (m, 2H), 3.23-3.30 (m, 1H), 2.91-3.01 (m, 6H), 2.25-2.33 (m, 5H), 2.03-2.06 (m, 2H), 1.33-1.35 (d, 6H), 1.26-1.28 (d, 6H); MS (ES+); 578.28 (M+1)+.

Example 2

(R)-(4-(4-(4-(2-(isopropylsulfonyl)phenylamino)
pyrazolo[1,5-a][1,3,5]triazin-2-ylamino)-5-methoxy-
2-methylphenyl)piperidin-1-yl)(morpholin-3-yl)
methanone (70)

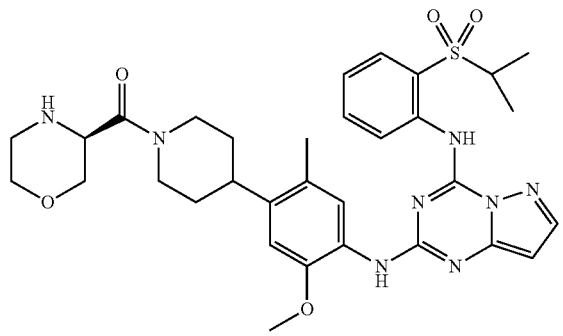 [SMILES: COc1cc(C2CCN(C(=O)[C@H]3COCCN3)CC2)c(C)cc1Nc1nc(Nc2ccccc2S(=O)(=O)C(C)C)n2nccc2n1]

To a mixture of N-(2-(isopropylsulfonyl)phenyl)-2-(methylsulfonyOpyrazolo[1,5-a][1,3,5]triazin-4-amine (6.3 g, 15.9 mmol) and 2-methoxy-5-methyl-4-(piperidin-4-yl) aniline TFA salt (15.9 mmol based on free base) in 80 mL of 2-propanol in a 350 mL round bottom pressure vessel was added TFA (1.22 mL, 15.9 mmol). The resulting mixture was heated at 150° C. for three hours. After cool down to room temperature, the product precipitated. The filtrate was washed with cold 2-propanol, and air dried to give $N^4$-(2-(isopropylsulfonyl)phenyl)-$N^2$-(2-methoxy-5-methyl-4-(piperidin-4-yl)phenyl)pyrazolo[1,5-a][1,3,5]triazine-2,4-diamine as TFA salt.

To a mixture of this TFA salt (1.26 g, 20 mmol), (R)-4-(tert-butoxycarbonyl)morpholine-3-carboxylic acid (0.504 g, 2.2 mmol) and HATU (0.847 g, 2.2 mmol) in 30 mL of DMF was added DIPEA (1.76 mL, 10 mmol). The resulting solution was stirred at room temperature for 30 minutes and then dropwise added into 150 mL of water. The precipitate was collected by filtration and air dry to give (R)-tert-butyl 3-(4-(4-(4-(2-(isopropylsulfonyl)phenylamino)pyrazolo[1,5-a][1,3,5]triazin-2-ylamino)-5-methoxy-2-methylphenyl) piperidine-1-carbonyl)morpholine-4-carboxylate as white solid. This carboxylate (1.3 g, 1.7 mmol) was dissolved in 10 mL of 4M HCl in 1,4-dioxane and stirred for 30 minutes at room temperature. Solvent was removed by evaporation and the residue was partitioned between 100 mL of $CH_2Cl_2$ and 100 mL of saturated $NaHCO_3$. The layers were separated and the aqueous layer was extracted with $CH_2Cl_2$ (3×100 mL). Combined organic layers were dried over $NaSO_3$, concentrated and purified by silica chromatography (0 to 8% MeOH in $CH_2Cl_2$ as eluent) to give the title compound as white solid. $^1$H NMR (CDCl$_3$, 400 MHz): δ 10.85 (broad s, 1H), 8.82-8.84 (dd, 1H), 8.30 (broad s, 1H), 7.98-7.99 (d, 1H), 7.95-7.98 (dd, 1H), 7.73-7.77 (dd, 1H), 7.46 (s, 1H), 7.32-7.36 (dd, 1H), 6.65-6.67 (d, 1H), 6.15-6.16 (d, 1H), 4.78-4.82 (m, 1H), 4.10-4.13 (m, 1H), 3.93-4.04 (m, 2H), 3.90 (s, 3H), 3.80-3.84 (m, 1H), 3.35-3.15 (m, 2H), 3.27-3.34 (m, 1H), 3.15-3.25 (m, 1H), 2.94-3.12 (m, 3H), 2.65-2.71 (m, 1H), 2.36 (s, 3H), 1.45-1.95 (m, 5H), 1.33-1.35 (d, 6H); MS (ES$^+$): 649.40 (M+1)$^+$.

Example 3

N5-(2-isopropoxy-5-methyl-4-(piperidin-4-yl)phenyl)-N7-(2-(isopropylsulfonyl)phenyl)pyrazolo[1,5-a]pyrimidine-5,7-diamine (82)

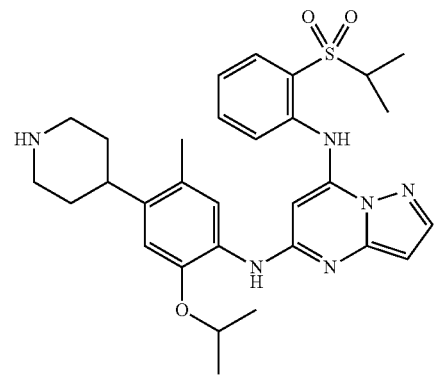 [SMILES: Cc1cc(Nc2cc(Nc3ccccc3S(=O)(=O)C(C)C)n3nccc3n2)c(OC(C)C)cc1C1CCNCC1]

5-chloro-N-(2-(isopropylsulfonyl)phenyl)pyrazolo[1,5-a]pyrimidin-7-amine

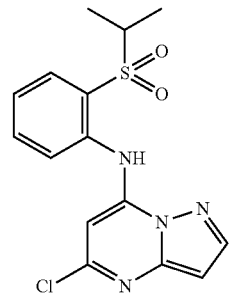 [SMILES: CC(C)S(=O)(=O)c1ccccc1Nc1cc(Cl)nc2ccnn12]

To a solution of 5,7-dichloro-pyrazolo[1,5-a]pyrimidine (1.0 mmol) and 2-(isopropylsulfonyl)aniline(1.0 mmol) in 5 mL of DMF, was added carefully NaH (24 mg). The resulting suspension was stirred at 50° C. for 2 hours. After cooling at RT and careful quenching (ice), water was added and the mixture was extracted with EtOAc. The organic layers were collected, dried (Na$_2$SO$_4$), filtrated and concentrated. The residue was purified over SiO$_2$ column chromatography (eluent: 9:1 Hexane:EtOAc), to give the desired 5-chloro-N-(2-(isopropylsulfonyl)phenyl)pyrazolo[1,5-a]pyrimidin-7-amine. MS (ES$^+$): 351.06 (M+1)$^+$.

N5-(2-isopropoxy-5-methyl-4-(piperidin-4-yl)phenyl)-N7-(2-(isopropylsulfonyl)phenyl)pyrazolo[1,5-a]pyrimidine-5,7-diamine To a solution of 5-chloro-N-(2-(isopropylsulfonyl)phenyl) pyrazolo[1,5-a]pyrimidin-7-amine (0.1 mmol) and 2-isopropoxy-5-methyl-4-(piperidin-4-yl)aniline (0.1 mmol) in 2 mL of isopropanol, was added 25 uL of HCl in dioxane (2 N). The suspension was stirred at 150° C. for 3 hours. After work-up and prep-HPLC, product was obtained. $^1$H NMR (CDCl$_3$, 400 MHz) δ 7.88-7.95 (m, 3H), 7.73-7.75 (d, 1H), 7.61-7.64 (m, 1H), 7.23-7.26 (m, 1H), 6.88 (s, 1H), 6.75 (s, 1H), 6.17-6.18 (d, 1H), 6.09 (s, 1H), 4.46-4.54 (m. 1H), 3.30-3.34 (m, 2H), 3.12-3.21 (m, 1H), 2.79-2.83 (m, 3H), 2.27 (s, 3H), 1.77-1.79 (m, 4H), 1.15-1.28 (m, 12H); MS (ES⁺): 563.28 (M+1)⁺.

Table 1 describes representative compounds of the invention, prepared following the procedures described above. IC50 values are as measured in an NPM-ALK BaF3 assay.

TABLE 1

| Ex # | Structure | Physical Data $^1$H NMR 400 MHz and/or MS (m/z) | IC$_{50}$ (nM) |
|---|---|---|---|
| 1 | 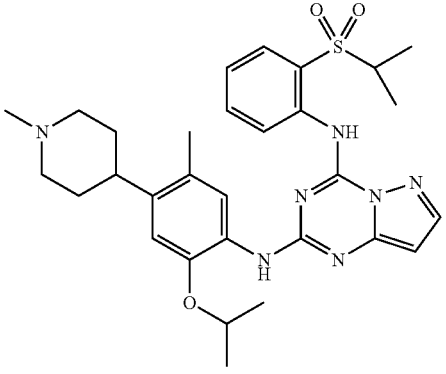<br>N2-(2-isopropoxy-5-methyl-4-(1-methylpiperidin-4-yl)phenyl)-N4-(2-(isopropylsulfonyl)phenyl)pyrazolo[1,5-a][1,3,5]triazine-2,4-diamine | $^1$H NMR (MeOD, 400 MHz) δ 8.51-8.54 (d, 1H), 7.94-8.04 (m, 2H), 7.35-7.47 (m, 3H), 6.90(s, 1H), 6.34-6.35 (d, 1H), 4.54-4.60 (m. 1H), 3.82-3.85 (m, 2H), 3.23-3.30 (m, 1H), 2.91-3.01 (m, 6H), 2.25-2.33 (m, 5H), 2.03-2.06 (m, 2H), 1.33-1.35 (d, 6H), 1.26-1.28(d, 6H); MS (ES⁺): 578.28 (M + 1)⁺. | 115 |
| 2 | 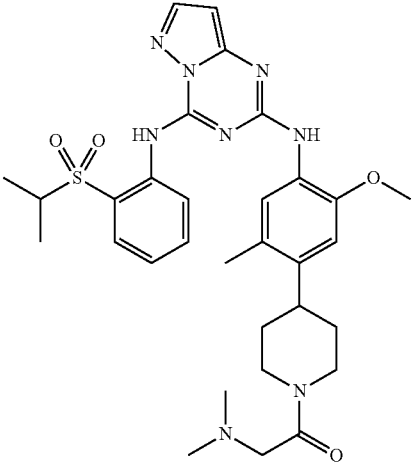<br>2-(dimethylamino)-1-(4-(4-(4-(2-(isopropylsulfonyl)phenylamino)pyrazolo[1,5-a][1,3,5]triazin-2-ylamino)-5-methoxy-2-methylphenyl)piperidin-1-yl)ethanone | $^1$H NMR (CDCl₃, 400 MHz) δ 10.85 (s, 1H), 8.83 (dd, 1H), 8.29 (s, 1H), 7.98 (d, 1H), 7.96 (dd, 1H), 7.74 (m, 1H), 7.46 (s, 1H), 7.34 (m, 1H), 6.69 (s, 1H), 6.15 (d, 1H), 4.78 (dm, 1H), 4.20 (dm, 1H), 3.89 (s, 3H), 3.34-3.23 (m, 2H), 3.22-3.08 (m, 1H), 3.02-2.90 (m, 1H), 2.74-2.64 (m, 1H), 2.39 (s, 6H), 2.36 (s, 3H), 2.02-1.90 (m, 1H), 1.88-1.80 (m, 2H), 1.70-1.56 (m, 2H), 1.34 (d, 6H); MS (ES⁺): 621.7 (M + 1)⁺. | 11 |

TABLE 1-continued

| Ex # | Structure | Physical Data<br>¹H NMR 400 MHz and/or MS<br>(m/z) | IC$_{50}$<br>(nM) |
|---|---|---|---|
| 3 | 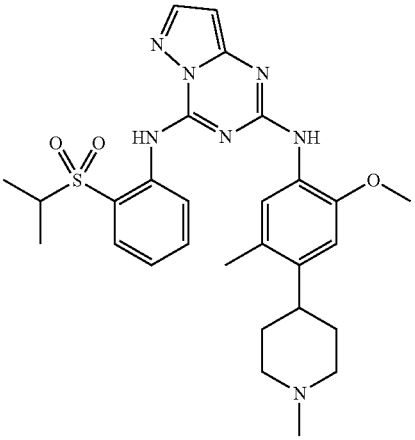<br>N4-(2-(isopropylsulfonyl)phenyl)-N2-(2-methoxy-5-methyl-4-(1-methylpiperidin-4-yl)phenyl)pyrazolo[1,5-a][1,3,5]triazine-2,4-diamine | MS (ES$^+$): 550.7 (M + 1)$^+$. | 19 |
| 4 | 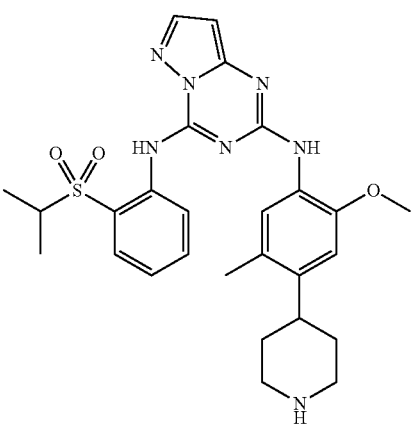<br>N4-(2-(isopropylsulfonyl)phenyl)-N2-(2-methoxy-5-methyl-4-(piperidin-4-yl)phenyl)pyrazolo[1,5-a][1,3,5]triazine-2,4-diamine | ¹H NMR (CDCl$_3$, 400 MHz): δ 8.82-8.84 (dd, 1H), 8.25 (broad s, 1H), 7.97-7.98 (d, 1H), 7.94-7.97 (dd, 1H), 7.72-7.76 (dd, 1H), 7.45 (broad s, 1H), 7.32-7.36 (dd, 1H), 6.82(s, 1H), 6.13-6.14 (d, 1H), 3.89(s, 3H), 3.27-3.34(m, 1H), 3.21-3.24(m, 2H), 2.76-2.87(m, 3H), 2.34(s, 3H), 1.77-1.80(m, 2H), 1.63-1.73(m, 2H), 1.33-1.35(d, 6H); MS (ES$^+$): 536.2 (M + 1)$^+$. | 38 |

TABLE 1-continued

| Ex # | Structure | Physical Data<br>¹H NMR 400 MHz and/or MS<br>(m/z) | IC$_{50}$<br>(nM) |
|---|---|---|---|
| 5 | 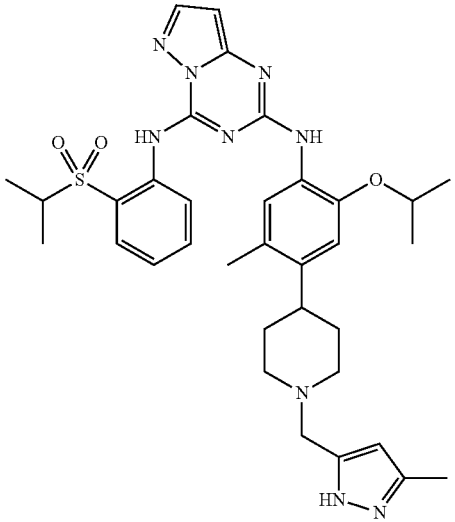<br>N2-(2-isopropoxy-5-methyl-4-(1-((3-methyl-1H-pyrazol-5-yl)methyl)piperidin-4-yl)phenyl)-N4-(2-(isopropylsulfonyl)phenyl)pyrazolo[1,5-a][1,3,5]triazine-2,4-diamine | MS (ES$^+$): 658.3 (M + 1)$^+$. | 140 |
| 6 | 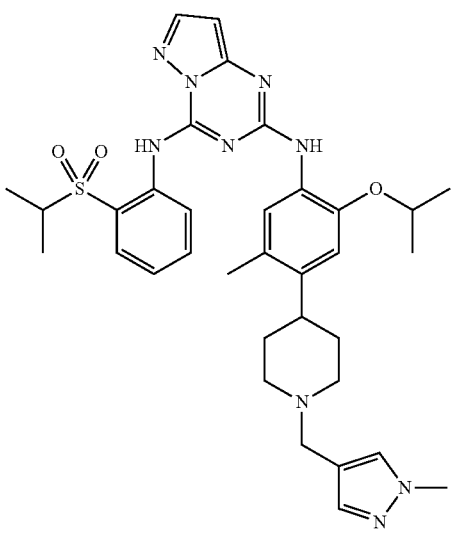<br>N2-(2-isopropoxy-5-methyl-4-(1-((1-methyl-1H-pyrazol-4-yl)methyl)piperidin-4-yl)phenyl)-N4-(2-(isopropylsulfonyl)phenyl)pyrazolo[1,5-a][1,3,5]triazine-2,4-diamine | MS (ES$^+$): 658.3 (M + 1)$^+$. | 80 |

TABLE 1-continued

| Ex # | Structure | Physical Data $^1$H NMR 400 MHz and/or MS (m/z) | IC$_{50}$ (nM) |
|---|---|---|---|
| 7 | 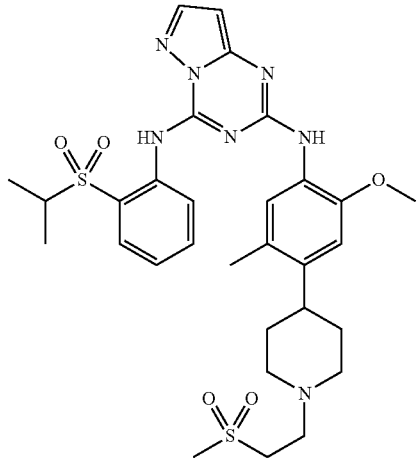 N4-(2-(isopropylsulfonyl)phenyl)-N2-(2-methoxy-5-methyl-4-(1-(2-(methylsulfonyl)ethyl)piperidin-4-yl)phenyl)pyrazolo[1,5-a][1,3,5]triazine-2,4-diamine | $^1$H NMR (CDCl$_3$, 400 MHz): δ 10.86 (broad s, 1H), 8.83-8.85 (dd, 1H), 8.28 (broad s, 1H), 7.98-7.99 (d,1H), 7.96-7.98 (dd, 1H), 7.73-7.77 (dd, 1H), 7.46 (s, 1H), 7.33-7.37 (dd, 1H), 6.76(s, 1H), 6.15-6.16 (d, 1H), 3.90 (s, 3H), 3.27-3.34 (m, 1H), 3.20-3.23(m, 2H), 3.07-3.09(m, 5H), 2.93-2.96(m, 2H), 2.69-2.77(m, 1H), 2.34(s, 3H), 2.19-2.25(m, 2H), 1.81-1.85(m, 2H), 1.67-1.77(m, 2H), 1.33-1.35(d, 6H); MS (ES$^+$): 642.3 (M + 1)$^+$. | 50 |
| 8 | 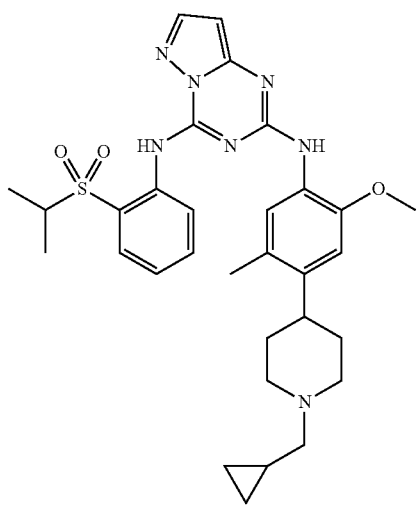 N2-(4-(1-(cyclopropylmethyl)piperidin-4-yl)-2-methoxy-5-methylphenyl)-N4-(2-(isopropylsulfonyl)phenyl)pyrazolo[1,5-a][1,3,5]triazine-2,4-diamine | MS (ES$^+$): 590.7 (M + 1)$^+$. | 43 |

TABLE 1-continued

| Ex # | Structure | Physical Data $^1$H NMR 400 MHz and/or MS (m/z) | IC$_{50}$ (nM) |
|---|---|---|---|
| 9 | N2-(4-(1-ethylpiperidin-4-yl)-2-methoxy-5-methylphenyl)-N4-(2-(isopropylsulfonyl)phenyl)pyrazolo[1,5-a][1,3,5]triazine-2,4-diamine | MS (ES$^+$): 564.78 (M + 1)$^+$. | |
| 10 | N4-(2-(isopropylsulfonyl)phenyl)-N2-(2-methoxy-5-methyl-4-(tetrahydro-2H-pyran-4-yl)phenyl)pyrazolo[1,5-a][1,3,5]triazine-2,4-diamine | MS (ES$^+$): 537.6 (M + 1)$^+$. | 138 |
| 11 | N2-(5-chloro-2-methyl-4-(piperidin-4-yl)phenyl)-N4-(2-(isopropylsulfonyl)phenyl)pyrazolo[1,5-a][1,3,5]triazine-2,4-diamine | MS (ES$^+$): 541.1 (M + 1)$^+$. | 1400 |

TABLE 1-continued

| Ex # | Structure | Physical Data $^1$H NMR 400 MHz and/or MS (m/z) | IC$_{50}$ (nM) |
|---|---|---|---|
| 12 | 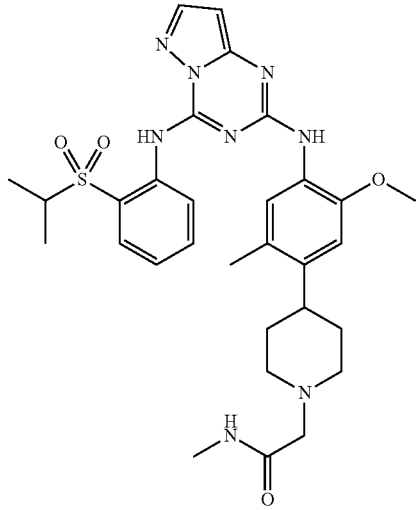<br>2-(4-(4-(4-(2-(isopropylsulfonyl)phenylamino)pyrazolo[1,5-a][1,3,5]triazin-2-ylamino)-5-methoxy-2-methylphenyl)piperidin-1-yl)-N-methylacetamide | $^1$H NMR (CDCl$_3$, 400 MHz) δ 10.84 (s, 1H), 8.82 (dd, 1H), 8.26 (s,, 1H), 7.97 (d, 1H), 7.95 (dd, 1H), 7.73 (m, 1H), 7.45 (s, 1H), 7.33 (m, 1H), 7.25-7.18 (m, 1H), 6.77 (s, 1H), 6.14 (d, 1H), 3.92 (s, 3H), 3.30 (septet, 1H), 3.06 (s, 2H), 2.98 (dm, 2H), 2.88 (d, 3H), 2.76-2.66 (m, 1H), 2.38-2.28 (m, 2H), 2.33 (s, 3H), 1.90-1.66 (m, 4H), 1.33 (d, 6H); MS (ES$^+$): 607.7 (M + 1)$^+$. | 28 |
| 13 | 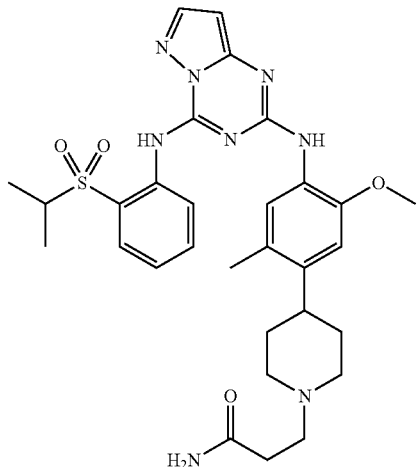<br>3-(4-(4-(4-(2-(isopropylsulfonyl)phenylamino)pyrazolo[1,5-a][1,3,5]triazin-2-ylamino)-5-methoxy-2-methylphenyl)piperidin-1-yl)propanamide | MS (ES$^+$): 607.7 (M + 1)$^+$. | 15 |

TABLE 1-continued

| Ex # | Structure | Physical Data<br>¹H NMR 400 MHz and/or MS<br>(m/z) | IC$_{50}$<br>(nM) |
|---|---|---|---|
| 14 | 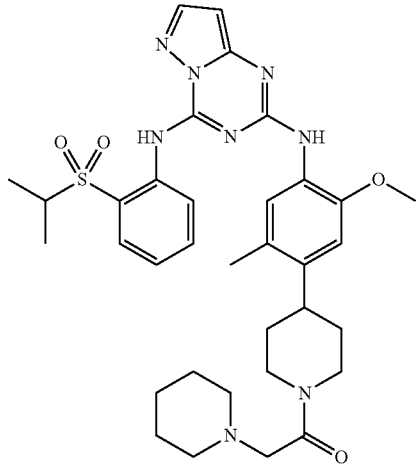<br>1-(4-(4-(4-(2-(isopropylsulfonyl)phenylamino)pyrazolo[1,5-a][1,3,5]triazin-2-ylamino)-5-methoxy-2-methylphenyl)piperidin-1-yl)-2-(piperidin-1-yl)ethanone | MS (ES⁺): 661.8 (M + 1)⁺. | 26 |
| 15 | 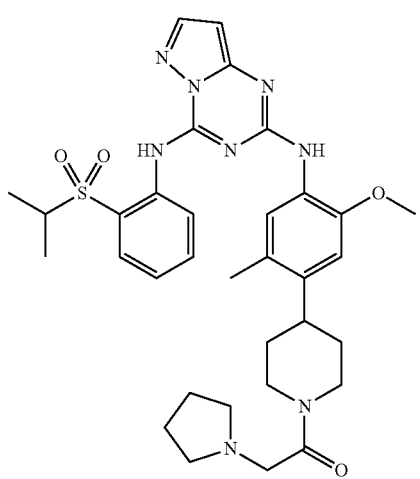<br>1-(4-(4-(4-(2-(isopropylsulfonyl)phenylamino)pyrazolo[1,5-a][1,3,5]triazin-2-ylamino)-5-methoxy-2-methylphenyl)piperidin-1-yl)-2-(pyrrolidin-1-yl)ethanone | ¹H NMR (CDCl₃, 400 MHz) δ 10.85 (s, 1H), 8.82 (dd, 1H), 8.30 (s, 1H), 7.97 (d, 1H), 7.95 (dd, 1H), 7.74 (m, 1H), 7.46 (s, 1H), 7.34 (m, 1H), 6.68 (s, 1H), 6.15 (d, 1H), 4.76 (dm, 1H), 4.00-3.86 (m, 2H), 3.90 (s, 3H), 3.84-3.75 (m, 1H), 3.30 (septet, 1H), 3.25-3.12 (m, 5H), 3.02-2.90 (m, 1H), 2.76-2.66 (m, 1H), 2.35 (s, 3H), 2.10-1.98 (m, 4H), 1.92-1.82 (m, 2H), 1.70-1.56 (m, 2H), 1.33 (d, 6H); MS (ES+): 647.3 (M + 1)⁺. | 31 |

TABLE 1-continued

| Ex # | Structure | Physical Data ¹H NMR 400 MHz and/or MS (m/z) | IC$_{50}$ (nM) |
|---|---|---|---|
| 16 | 3-(4-(4-(4-(2-(isopropylsulfonyl)phenylamino)pyrazolo[1,5-a][1,3,5]triazin-2-ylamino)-5-methoxy-2-methylphenyl)piperidin-1-yl)-N,N-dimethylpropanamide | MS (ES$^+$): 635.8 (M + 1)$^+$. | |
| 17 | 1-(4-(4-(4-(2-(isopropylsulfonyl)phenylamino)pyrazolo[1,5-a][1,3,5]triazin-2-ylamino)-5-methoxy-2-methylphenyl)piperidin-1-yl)-2-(methylamino)ethanone | ¹H NMR (CDCl$_3$, 400 MHz) δ 8.82 (dd, 1H), 8.29 (s, 1H), 7.97 (d, 1H), 7.95 (dd, 1H), 7.74 (m, 1H), 7.46 (s, 1H), 7.33 (m, 1H), 6.71 (s, 1H), 6.67 (s, 1H), 6.14 (d, 1H), 4.78 (dm, 1H), 4.12-3.60 (m, 3H), 3.90 (s, 3H), 3.31 (septet, 1H), 3.24-3.10 (m, 1H), 3.02-2.90 (m, 1H), 2.80-2.68 (m, 1H), 2.64 (s, 3H), 2.50-2.40 (m, 1H), 2.34 (s, 3H), 1.94-1.76 (m, 2H), 1.74-1.58 (m, 2H), 1.33 (d, 6H); MS (ES$^+$): 607.7 (M + 1)$^+$. | 22 |

TABLE 1-continued

| Ex # | Structure | Physical Data $^1$H NMR 400 MHz and/or MS (m/z) | IC$_{50}$ (nM) |
|---|---|---|---|
| 18 | 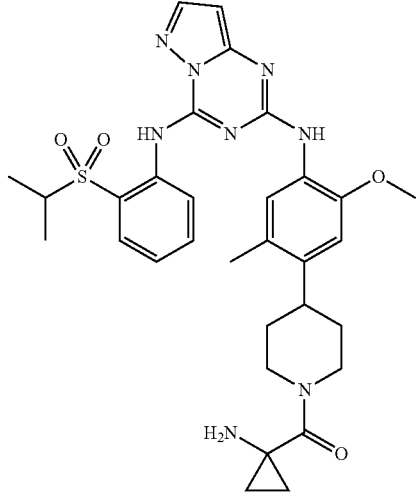<br>(1-aminocyclopropyl)(4-(4-(4-(2-(isopropylsulfonyl)phenylamino)pyrazolo[1,5-a][1,3,5]triazin-2-ylamino)-5-methoxy-2-methylphenyl)piperidin-1-yl)methanone | $^1$H NMR (CDCl$_3$, 400 MHz) δ 8.82 (dd, 1H), 8.30 (s, 1H), 7.98 (d, 1H), 7.95 (dd, 1H), 7.74 (m, 1H), 7.46 (s, 1H), 7.34 (m, 1H), 6.68 (s, 1H), 6.15 (d, 1H), 4.62 (dm, 2H), 3.89 (s, 3H), 3.30 (septet, 1H), 3.05-2.90 (m, 3H), 2.37 (s, 3H), 1.92-1.80 (m, 3H), 1.70-1.55 (m, 3H), 1.33 (d, 6H), 1.05 (dd, 2H), 0.85 (dd, 2H); MS (ES$^+$): 619.7 (M + 1)$^+$. | 39 |
| 19 | 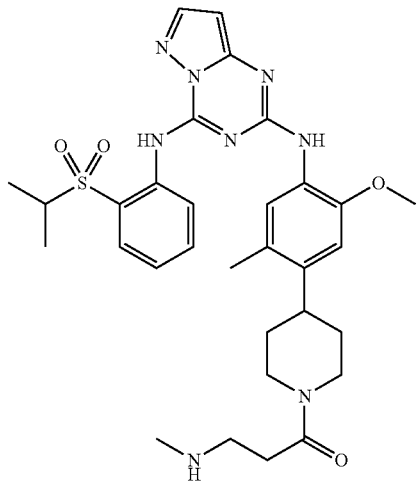<br>1-(4-(4-(4-(2-(isopropylsulfonyl)phenylamino)pyrazolo[1,5-a][1,3,5]triazin-2-ylamino)-5-methoxy-2-methylphenyl)piperidin-1-yl)-3-(methylamino)propan-1-one | MS (ES$^+$): 621.7 (M + 1)$^+$. | 68 |

TABLE 1-continued

| Ex # | Structure | Physical Data $^1$H NMR 400 MHz and/or MS (m/z) | IC$_{50}$ (nM) |
|---|---|---|---|
| 20 | 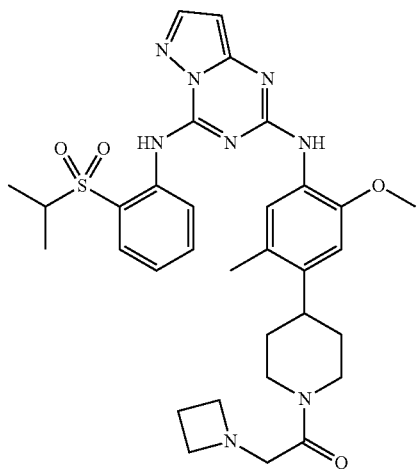 2-(azetidin-1-yl)-1-(4-(4-(4-(2-(isopropylsulfonyl)phenylamino)pyrazolo[1,5-a][1,3,5]triazin-2-ylamino)-5-methoxy-2-methylphenyl)piperidin-1-yl)ethanone | MS (ES$^+$): 633.8 (M + 1)$^+$. | 26 |
| 21 | 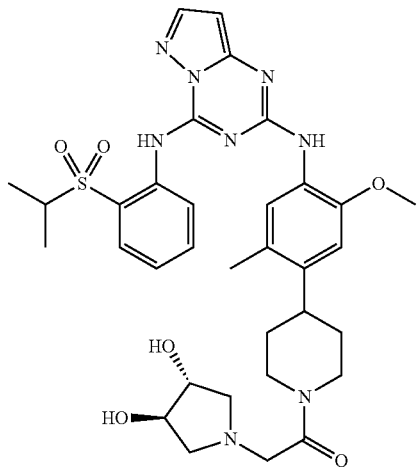 2((3R,4R)-3,4-dihydroxypyrrolidin-1-yl)-1-(4-(4-(4-(2-(isopropylsulfonyl)phenylamino)pyrazolo[1,5-a][1,3,5]triazin-2-ylamino)-5-methoxy-2-methylphenyl)piperidin-1-yl)ethanone | MS (ES$^+$): 679.8 (M + 1)$^+$. | 286 |

TABLE 1-continued

| Ex # | Structure | Physical Data $^1$H NMR 400 MHz and/or MS (m/z) | IC$_{50}$ (nM) |
|---|---|---|---|
| 22 | 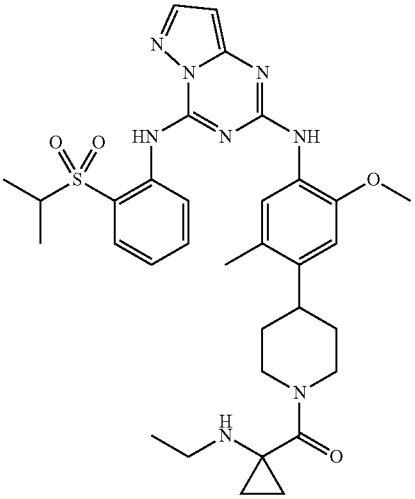<br>(1-(ethylamino)cyclopropyl)(4-(4-(4-(2-(isopropylsulfonyl)phenylamino)pyrazolo[1,5-a][1,3,5]triazin-2-ylamino)-5-methoxy-2-methylphenyl)piperidin-1-yl)methanone | $^1$H NMR (CDCl$_3$, 400 MHz) δ 8.83 (dd, 1H), 8.30 (s, 1H), 7.98 (d, 1H), 7.96 (dd, 1H), 7.74 (m, 1H), 7.46 (s, 1H), 7.34 (m, 1H), 6.67 (s, 1H), 6.15 (d, 1H), 4.67 (dm, 2H), 3.89 (s, 3H), 3.30 (septet, 1H), 3.04-2.92 (m, 2H), 2.80 (s, 1H), 2.75 (q, 2H), 2.37 (s, 3H), 1.91-1.83 (m, 2H), 1.67-1.54 (m, 3H), 1.33 (d, 6H), 1.10 (t, 3H), 1.04 (dd, 2H), 0.81 (dd, 2H); MS (ES$^+$): 647.8 (M + 1)$^+$. | 23 |
| 23 | 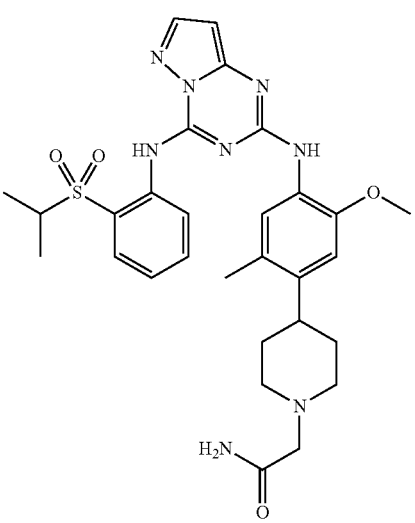<br>2-4-(4-(4-(2-(isopropylsulfonyl)phenylamino)pyrazolo[1,5-a][1,3,5]triazin-2-ylamino)-5-methoxy-2-methylphenyl)piperidin-1-yl)acetamide | MS (ES$^+$): 593.7 (M + 1)$^+$. | 16 |

TABLE 1-continued

| Ex # | Structure | Physical Data $^1$H NMR 400 MHz and/or MS (m/z) | IC$_{50}$ (nM) |
|---|---|---|---|
| 24 | 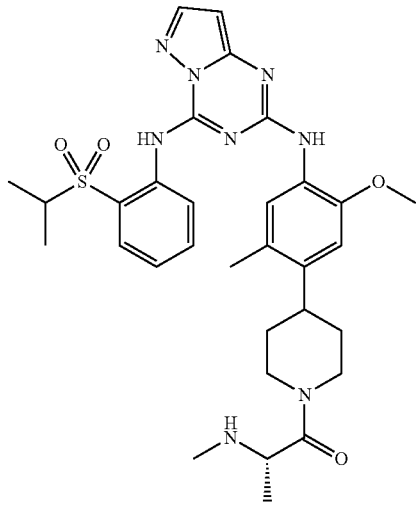<br>(S)-1-(4-(4-(4-(2-(isopropylsulfonyl)phenylamino)pyrazolo[1,5-a][1,3,5]triazin-2-ylamino)-5-methoxy-2-methylphenyl)piperidin-1-yl)-2-(methylamino)propan-1-one | $^1$H NMR (CDCl$_3$, 400 MHz) δ 8.82 (dd, 1H), 8.30 (s, 1H), 7.97 (d, 1H), 7.95 (dd, 1H), 7.74 (m, 1H), 7.46 (s, 1H), 7.34 (m, 1H), 6.67 (d, 1H), 6.15 (d, 1H), 4.92-4.76 (m, 1H), 4.08-3.98 (m, 1H), 3.89 (s, 3H), 3.66-3.54 (m, 1H), 3.30 (septet, 1H), 3.26-3.12 (m, 1H), 3.04-2.92 (m, 1H), 2.78-2.66 (m, 1H), 2.39 (d, 3H), 2.36 (s, 3H), 1.94-1.82 (m, 2H), 1.72-1.46 (m, 2H), 1.33 (d, 6H), 1.29 (dd, 3H); MS (ES$^+$): 621.7 (M + 1)$^+$. | 21 |
| 25 | 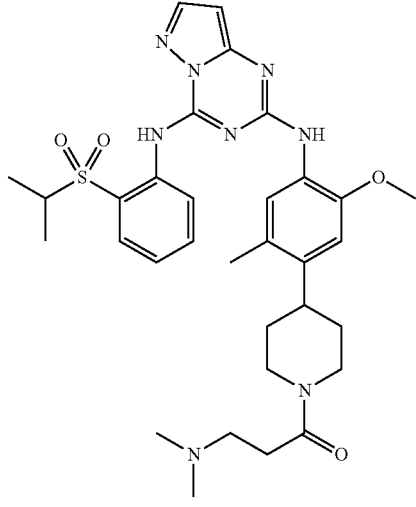<br>3-(dimethylamino)-1-(4-(4-(4-(2-(isopropylsulfonyl)phenylamino)pyrazolo[1,5-a][1,3,5]triazin-2-ylamino)-5-methoxy-2-methylphenyl)piperidin-1-yl)propan-1-one | $^1$H NMR (CDCl$_3$, 400 MHz): δ 10.84 (broad s, 1H), 8.81-8.83 (dd, 1H), 8.26 (broad s, 1H), 7.95-7.96 (d,1H), 7.93-7.95 (dd, 1H), 7.72-7.76 (dd, 1H), 7.45 (s, 1H), 7.31-7.35 (dd, 1H), 6.77(s, 1H), 6.12-6.13 (d, 1H), 4.67-4.71 (m, 1H), 3.94-3.98 (m, 1H), 3.92(s, 3H), 3.41-3.52(m, 2H), 3.29-3.36(m, 1H), 3.12-3.27(m, 1H), 2.94-3.05(m, 8H), 2.82-2.90(m, 1H), 2.71-2.77(m, 1H), 2.36 (s, 3H), 1.81-1.84(m, 2H), 1.62-1.73(m, 2H), 1.34-1.36(d, 6H); MS (ES$^+$): 635.3 (M + 1)$^+$. | 22 |

TABLE 1-continued

| Ex # | Structure | Physical Data ¹H NMR 400 MHz and/or MS (m/z) | IC$_{50}$ (nM) |
|---|---|---|---|
| 26 | 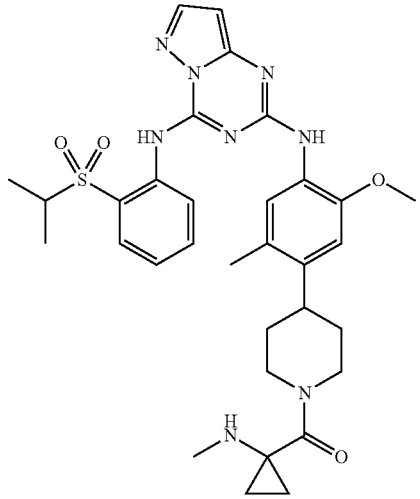<br>(4-(4-(4-(2-(isopropylsulfonyl)phenylamino)pyrazolo[1,5-a][1,3,5]triazin-2-ylamino)-5-methoxy-2-methylphenyl)piperidin-1-yl)(1-(methylamino)cyclopropyl)methanone | MS (ES$^+$): 633.8 (M + 1)$^+$. | 25 |
| 27 | 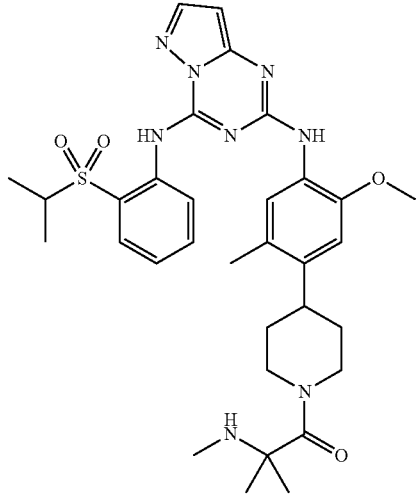<br>1-(4-(4-(4-(2-(isopropylsulfonyl)phenylamino)pyrazolo[1,5-a][1,3,5]triazin-2-ylamino)-5-methoxy-2-methylphenyl)piperidin-1-yl)(2-methyl-2-(methylamino)propan-1-one | MS (ES$^+$): 635.8 (M + 1)$^+$. | 44 |

TABLE 1-continued

| Ex # | Structure | Physical Data ¹H NMR 400 MHz and/or MS (m/z) | IC$_{50}$ (nM) |
|---|---|---|---|
| 28 | 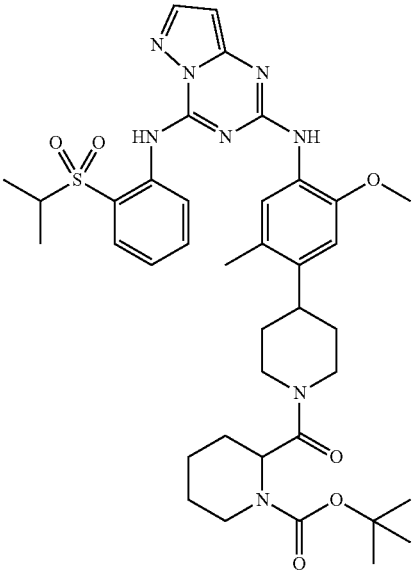<br>tert-butyl 2-(4-(4-(4-(2-(isopropylsulfonyl)phenylamino)pyrazolo[1,5-a][1,3,5]triazin-2-ylamino)-5-methoxy-2-methylphenyl)piperidine-1-carbonyl)piperidine-1-carboxylate | MS (ES$^+$): 747.9 (M + 1)$^+$. | |
| 29 | 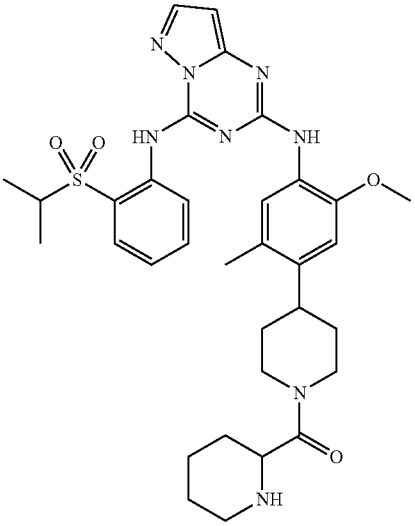<br>(4-(4-(4-(2(isopropylsulfonyl)phenylamino)pyrazolo[1,5-a][1,3,5]triazin-2-ylamino)-5-methoxy-2-methylphenyl)piperidin-1-yl)(piperidin-2-yl)methanone | MS (ES$^+$): 647.8 (M + 1)$^+$. | 54 |

TABLE 1-continued

| Ex # | Structure | Physical Data ¹H NMR 400 MHz and/or MS (m/z) | IC$_{50}$ (nM) |
|---|---|---|---|
| 30 | t-butyl 3-(4-(4-(4-(2-(isopropylsulfonyl)phenyl amino)pyrazolo[1,5-a][1,3,5]triazin-2-ylamino)-5-methoxy-2-methylphenyl)piperidine-1-carbonyl)morpholine-4-carboxylate | MS (ES$^+$): 749.9 (M + 1)$^+$. | |
| 31 | (4-(4-(4-(2-(isopropylsulfonyl)phenylamino)pyrazolo[1,5-a][1,3,5]triazin-2-ylamino)-5-methoxy-2-methylphenyl)piperidine-1-yl)(pyrrolidin-2-yl)methanone | MS (ES$^+$): 633.8 (M + 1)$^+$. | 36 |

TABLE 1-continued

| Ex # | Structure | Physical Data<br>¹H NMR 400 MHz and/or MS<br>(m/z) | IC$_{50}$<br>(nM) |
| --- | --- | --- | --- |
| 32 | (4-(4-(4-(2-(isopropylsulfonyl)phenylamino)pyrazolo[1,5-a][1,3,5]triazin-2-ylamino)-5-methoxy-2-methylphenyl)piperidin-1-yl)(morpholin-3-yl)methanone | MS (ES⁺): 649.8 (M + 1)⁺. | 29 |
| 33 | N2-(2,5-dimethyl-4-(piperidin-4-yl)phenyl)-N4-(2-(isopropylsulfonyl)phenyl)pyrazolo[1,5-a][1,3,5]triazine-2,4-diamine | MS (ES⁺): 520.7 (M + 1)⁺. | |

TABLE 1-continued

| Ex # | Structure | Physical Data<br>¹H NMR 400 MHz and/or MS<br>(m/z) | IC$_{50}$<br>(nM) |
|---|---|---|---|
| 34 | (4-(4-(4-(2-(isopropylsulfonyl)phenylamino)pyrazolo[1,5-a][1,3,5]triazin-2-ylamino)-5-methoxy-2-methylphenyl)piperidin-1-yl)(1-methylpyrrolidin-2-yl)methanone | MS (ES⁺): 647.8 (M + 1)⁺. | 25 |
| 35 | N4-(2-(isopropylsulfonyl)phenyl)-N2-(2-methoxy-5-(3-methyl-1,2,4-oxadiazol-5-yl)phenyl)pyrazolo[1,5-a][1,3,5]triazine-2,4-diamine | MS (ES⁺): 521.6 (M + 1)⁺. | |
| 36 | N2-(2-isopropoxy-5-(3-methylisoxazol-5-yl)phenyl)-N4-(2-(isopropylsulfonyl)phenyl)pyrazolo[1,5-a][1,3,5]triazine-2,4-diamine | MS (ES⁺): 548.6 (M + 1)⁺. | |

TABLE 1-continued

| Ex # | Structure | Physical Data $^1$H NMR 400 MHz and/or MS (m/z) | IC$_{50}$ (nM) |
|---|---|---|---|
| 37 | N4-(2-(isopropylsulfonyl)phenyl)-N2-(4-(piperidin-4-yl)phenyl)pyrazolo[1,5-a][1,3,5]triazine-2,4-diamine | MS (ES$^+$): 492.6 (M + 1)$^+$. | 130 |
| 38 | (S)-2-amino-3-(4-(4-(2-(isopropylsulfonyl)phenylamino)pyrazolo[1,5-a][1,3,5]triazin-2-ylamino)phenyl)propanoic acid | MS (ES$^+$): 496.6 (M + 1)$^+$. | |
| 39 | N4-(2-(isopropylsulfonyl)phenyl)-N2-(2-(2-(methylsulfonyl)ethyl)-1,2,3,4-tetrahydroisoquinolin-7-yl)pyrazolo[1,5-a][1,3,5]triazine-2,4-diamine | MS (ES$^+$): 570.7 (M + 1)$^+$. | 464 |

TABLE 1-continued

| Ex # | Structure | Physical Data ¹H NMR 400 MHz and/or MS (m/z) | IC$_{50}$ (nM) |
|---|---|---|---|
| 40 | N4-(2-(isopropylsulfonyl)phenyl)-N2-(2-(2-(methylsulfonyl)ethyl)-1,2,3,4-tetrahydroisoquinolin-6-yl)pyrazolo[1,5-a][1,3,5]triazine-2,4-diamine | MS (ES$^+$): 570.7 (M + 1)$^+$. | 136 |
| 41 | N4-(2-(isopropylsulfonyl)phenyl)-N2-(1,2,3,4-tetrahydroisoquinolin-6-yl)pyrazolo[1,5-a][1,3,5]triazine-2,4-diamine | MS (ES$^+$): 464.6 (M + 1)$^+$. | 85 |
| 42 | N4-(2-(isopropylsulfonyl)phenyl)-N2-(1,2,3,4-tetrahydroisoquinolin-7-yl)pyrazolo[1,5-a][1,3,5]triazine-2,4-diamine | MS (ES$^+$): 464.6 (M + 1)$^+$. | 1017 |

TABLE 1-continued

| Ex # | Structure | Physical Data<br>¹H NMR 400 MHz and/or MS<br>(m/z) | IC₅₀<br>(nM) |
|---|---|---|---|
| 43 | (R)-2-(2,3-dihydroxypropylamino)-1-(4-(4-(4-(2-(isopropylsulfonyl)phenylamino)pyrazolo[1,5-a][1,3,5]triazin-2-ylamino)-5-methoxy-2-methylphenyl)piperidin-1-yl)ethanone | MS (ES+): 667.8 (M + 1)+. | 150 |
| 44 | (R)-1-(4-(4-(4-(2-(isopropylsulfonyl)phenylamino)pyrazolo[1,5-a][1,3,5]triazin-2-ylamino)-5-methoxy-2-methylphenyl)piperidin-1-yl)-2-(methylamino)propan-1-one | ¹H NMR (CDCl₃, 400 MHz) δ 8.82 (dd, 1H), 8.30 (s, 1H), 7.97 (d, 1H), 7.95 (dd, 1H), 7.74 (m, 1H), 7.46 (s, 1H), 7.34 (m, 1H), 6.67 (d, 1H), 6.15 (d, 1H), 4.92-4.76 (m, 1H), 4.08-3.98 (m, 1H), 3.89 (s, 3H), 3.66-3.54 (m, 1H), 3.30 (septet, 1H), 3.26-3.12 (m, 1H), 3.04-2.92 (m, 1H), 2.78-2.66 (m, 1H), 2.39 (d, 3H), 2.36 (s, 3H), 1.94-1.82 (m, 2H), 1.72-1.46 (m, 2H), 1.33 (d, 6H), 1.29 (dd, 3H); MS (ES+): 621.7 (M + 1)+. | 18 |
| 45 | N2-(2,5-dimethyl-4-(1-(2-(methylsulfonyl)ethyl)piperidin-4-yl)phenyl)-N4-(2-(isopropylsulfonyl)phenyl)pyrazolo[1,5-a][1,3,5]triazine-2,4-diamine | MS (ES+): 626.8 (M + 1)+. | 62 |

TABLE 1-continued

| Ex # | Structure | Physical Data $^1$H NMR 400 MHz and/or MS (m/z) | IC$_{50}$ (nM) |
|---|---|---|---|
| 46 | 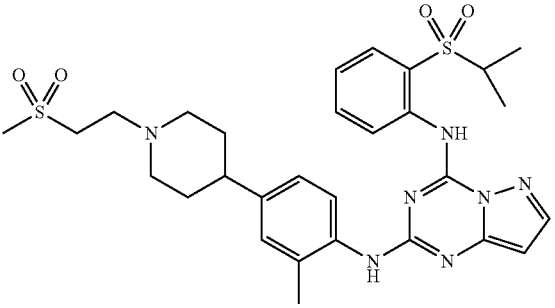<br>N4-(2-(isopropylsulfonyl)phenyl)-N2-(2-methyl-4-(1-(2-(methylsulfonyl)ethyl)piperidin-4-yl)phenyl)prazolo[1,5-a][1,3,5]triazine-2,4-diamine | MS (ES$^+$): 612.8 (M + 1)$^+$. | 31 |
| 47 | 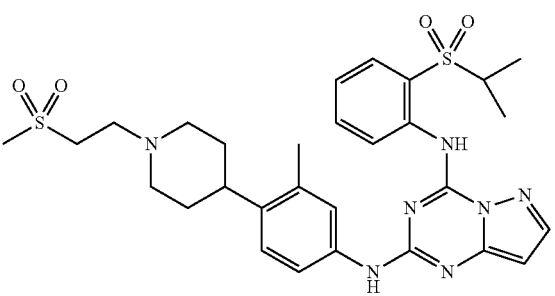<br>N4-(2-(isopropylsulfonyl)phenyl)-N2-(3-methyl-4-(1-(2-(methylsulfonyl)ethyl)piperidin-4-yl)phenyl)prazolo[1,5-a][1,3,5]triazine-2,4-diamine | MS (ES$^+$): 612.8 (M + 1)$^+$. | 46 |
| 48 | 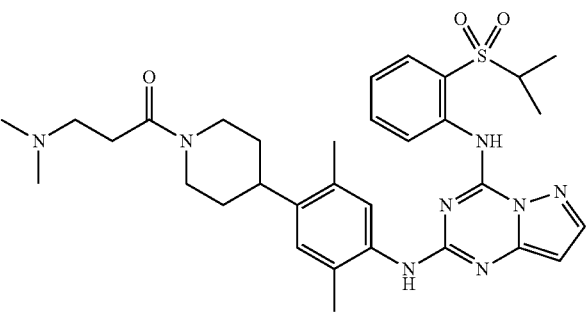<br>3-(dimethylamino-1-(4-(4-(4-(2-(isopropylsulfonyl)phenylamino)pyrazolo[1,5-a][1,3,5]triazin-2-ylamino)-2,5-dimethylphenyl)piperidin-1-yl)propan-1-one | MS (ES$^+$): 619.8 (M + 1)$^+$. | 59 |

TABLE 1-continued

| Ex # | Structure | Physical Data ¹H NMR 400 MHz and/or MS (m/z) | IC$_{50}$ (nM) |
|---|---|---|---|
| 49 | 3-(dimethylamino-1-(4-(4-(4-(2-(isopropylsulfonyl)phenylamino)pyrazolo[1,5-a][1,3,5]triazin-2-ylamino)-3-methylphenyl)piperidin-1-yl)propan-1-one | MS (ES⁺): 605.8 (M + 1)⁺. | 129 |
| 50 | ((2S,4R)-4-hydroxy-1-methylpyrrolidin-2-yl)(4-(4-(4-(2-(isopropylsulfonyl)phenylamino)pyrazolo[1,5-a][1,3,5]triazin-2-ylamino)-5-methoxy-2-methylphenyl)piperidin-1-yl)methanone | MS (ES⁺): 663.8 (M + 1)⁺. | 52 |
| 51 | ((2S,4R)-4-hydroxypyrrolidin-2-yl)(4-(4-(4-(2-(isopropylsulfonyl)phenylamino)pyrazolo[1,5-a][1,3,5]triazin-2-ylamino)-5-methoxy-2-methylphenyl)piperidin-1-yl)methanone | MS (ES⁺): 649.8 (M + 1)⁺. | |

TABLE 1-continued

| Ex # | Structure | Physical Data<br>¹H NMR 400 MHz and/or MS<br>(m/z) | IC$_{50}$<br>(nM) |
|---|---|---|---|
| 52 | (S)-(4-(4-(4-(2-(isopropylsulfonyl)phenylamino)pyrazolo[1,5-a][1,3,5]triazin-2-ylamino)-5-methoxy-2-methylphenyl)piperidin-1-yl)(pyrrolidin-2-yl)methanone | MS (ES⁺): 633.8 (M + 1)⁺. | |
| 53 | ((2S,3S)-3-hydroxypyrrolidin-2-yl)(4-(4-(4-(2-(isopropylsulfonyl)phenylamino) pyrazolo[1,5-a][1,3,5]triazin-2-ylamino)-5-methoxy-2-methylphenyl)piperidin-1-yl)methanone | MS (ES⁺): 649.8 (M + 1)⁺. | |
| 54 | ((2S,4S)-4-fluoropyrrolidin-2-yl)(4-(4-(4-(2-(isopropylsulfonyl)phenylamino) pyrazolo[1,5-a][1,3,5]triazin-2-ylamino)-5-methoxy-2-methylphenyl)piperidin-1-yl)methanone | MS (ES⁺): 651.8 (M + 1)⁺. | 42 |

TABLE 1-continued

| Ex # | Structure | Physical Data<br>¹H NMR 400 MHz and/or MS<br>(m/z) | IC$_{50}$<br>(nM) |
|---|---|---|---|
| 55 | ((2S,4S)-4-hydroxypyrrolidin-2-yl)(4-(4-(4-(2-(isopropylsulfonyl)phenylamino) pyrazolo[1,5-a][1,3,5]triazin-2-ylamino)-5-methoxy-2-methylphenyl)piperidin-1-yl)methanone | MS (ES⁺): 649.8 (M + 1)⁺. | 63 |
| 56 | ((2R,4R)-4-hydroxypyrrolidin-2-yl)(4-(4-(4-(2-(isopropylsulfonyl)phenylamino) pyrazolo[1,5-a][1,3,5]triazin-2-ylamino)-5-methoxy-2-methylphenyl)piperidin-1-yl)methanone | MS (ES⁺): 649.8 (M + 1)⁺. | 79 |
| 57 | 2-(isopropylamino)-1-(4-(4-(4-(2-(isopropylsulfonyl)phenylamino)pyrazolo[1,5-a][1,3,5]triazin-2-ylamino)-5-methoxy-2-methylphenyl)piperidin-1-yl)ethanone | MS (ES⁺): 635.8 (M + 1)⁺. | 32 |

TABLE 1-continued

| Ex # | Structure | Physical Data <br> 1H NMR 400 MHz and/or MS (m/z) | IC50 (nM) |
|---|---|---|---|
| 58 | 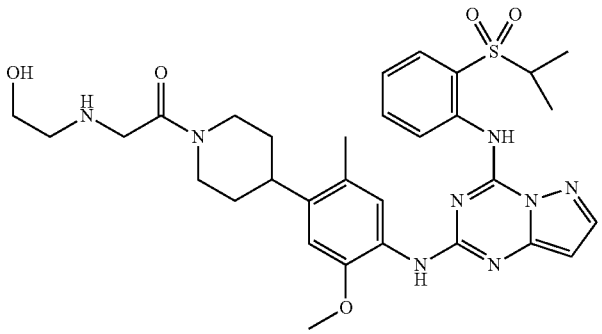 <br> 2-(2-hydroxyethylamino)-1-(4-(4-(4-(2-(isopropylsulfonyl)phenylamino)pyrazolo[1,5-a][1,3,5]triazin-2-ylamino)-5-methoxy-2-methylphenyl)piperidin-1-yl)ethanone | 1H NMR (CDCl$_3$, 400 MHz) δ 8.82 (dd, 1H), 8.30 (s, 1H), 7.98 (d, 1H), 7.96 (dd, 1H), 7.74 (m, 1H), 7.46 (s, 1H), 7.34 (m, 1H), 6.67 (s, 1H), 6.15 (d, 1H), 4.82 (dm, 1H), 3.94-3.82 (m, 1H), 3.90 (s, 3H), 3.65 (dd, 2H), 3.55 (dd, 2H), 3.30 (septet, 1H), 3.22-3.07 (m, 1H), 3.03-2.93 (m, 1H), 2.90-2.82 (m, 2H), 2.78-2.67 (m, 1H), 2.36 (s, 3H), 1.92-1.80 (m, 2H), 1.72-1.52 (m, 2H), 1.33 (d, 6H); MS (ES$^+$): 637.8 (M + 1)$^+$. | 86 |
| 59 | 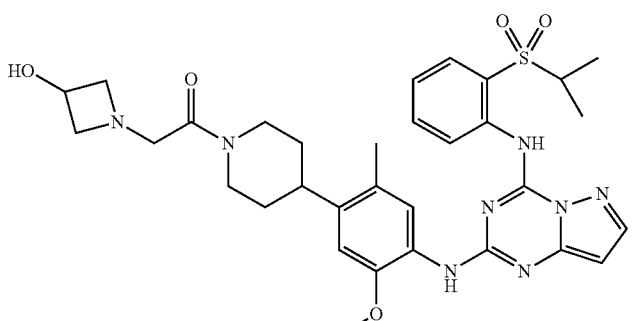 <br> 2-(3-hydroxyazetidin-1-yl)-1-(4-(4-(4-(2-(isopropylsulfonyl)phenylamino)pyrazolo[1,5-a][1,3,5]triazin-2-ylamino)-5-methoxy-2-methylphenyl)piperidin-1-yl)ethanone | MS (ES$^+$): 649.8 (M + 1)$^+$. | 193 |
| 60 | 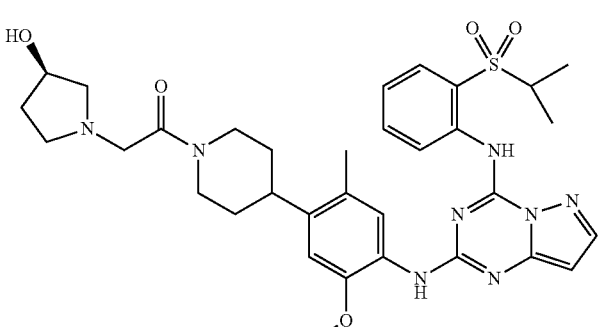 <br> (R)-2-(3-hydroxypyrrolidin-1-yl)-1-(4-(4-(4-(2-(isopropylsulfonyl)phenylamino)pyrazolo[1,5-a][1,3,5]triazin-2-ylamino)-5-methoxy-2-methylphenyl)piperidin-1-yl)ethanone | MS (ES$^+$): 663.8 (M + 1)$^+$. | 31 |

TABLE 1-continued

| Ex # | Structure | Physical Data $^1$H NMR 400 MHz and/or MS (m/z) | IC$_{50}$ (nM) |
|---|---|---|---|
| 61 | 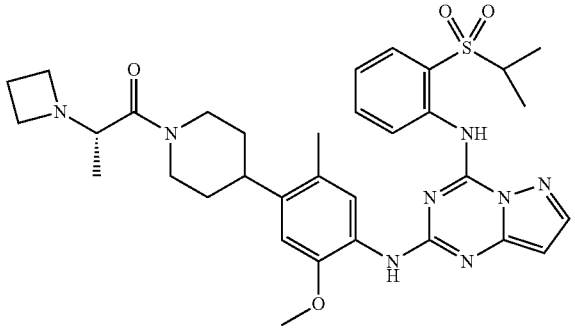 (S)-2-(azetidin-1-yl)-1-(4-(4-(4-(2-(isopropylsulfonyl)phenylamino)pyrazolo[1,5-a][1,3,5]triazin-2-ylamino)-5-methoxy-2-methylphenyl)piperidin-1-yl)propan-1-one | MS (ES$^+$): 647.8 (M + 1)$^+$. | 34 |
| 62 | 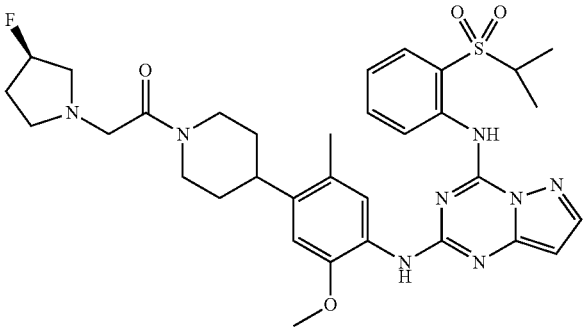 (R)-2-(3-fluoropyrrolidin-1-yl)-1-(4-(4-(4-(2-(isopropylsulfonyl)phenylamino) pyrazolo[1,5-a][1,3,5]triazin-2-ylamino)-5-methoxy-2-methylphenyl)piperidin-1-yl)ethanone | $^1$H NMR (CDCl$_3$, 400 MHz) δ 10.84 (s, 1H), 8.82 (dd, 1H), 8.28 (s, 1H), 7.97 (d, 1H), 7.96 (dd, 1H), 7.74 (m, 1H), 7.46 (s, 1H), 7.34 (m, 1H), 6.68 (d, 1H), 6.14 (d, 1H), 5.20 (dm, 1H), 4.78 (dm, 1H), 4.16 (m, 1H), 3.88 (d, 3H), 3.62-3.24 (m, 3H), 3.20-2.84 (m, 4H), 2.74-2.52 (m, 2H), 2.35 (s, 3H), 2.30-1.98 (m, 2H), 1.96-1.48 (m, 5H), 1.33 (d, 6H); MS (ES$^+$): 665.8 (M + 1)$^+$. | 58 |
| 63 | 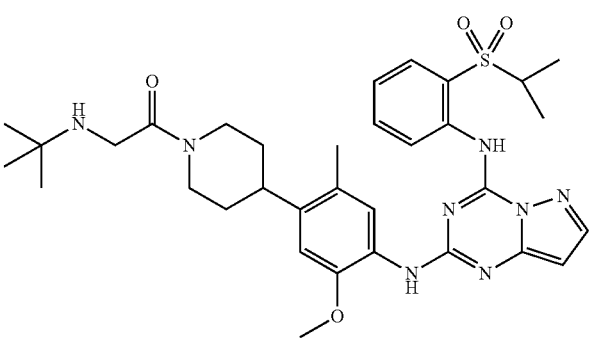 2-(tert-butylamino)-1-(4-(4-(4-(2-(isopropylsulfonyl)phenylamino)pyrazolo[1,5-a][1,3,5]triazin-2-ylamino)-5-methoxy-2-methylphenyl)piperidin-1-yl)ethanone | MS (ES$^+$): 649.8 (M + 1)$^+$. | 53 |

TABLE 1-continued

| Ex # | Structure | Physical Data $^1$H NMR 400 MHz and/or MS (m/z) | IC$_{50}$ (nM) |
|---|---|---|---|
| 64 | (S)-2-(isopropylamino)-1-(4-(4-(4-(2-(isopropylsulfonyl)phenylamino)pyrazolo[1,5-a][1,3,5]triazin-2-ylamino)-5-methoxy-2-methylphenyl)piperidin-1-yl)propan-1-one | MS (ES$^+$): 649.8 (M + 1)$^+$. | 28 |
| 65 | (S)-2-(2-hydroxyethylamino)-1-(4-(4-(4-(2-(isopropylsulfonyl)phenylamino)pyrazolo[1,5-a][1,3,5]triazin-2-ylamino)-5-methoxy-2-methylphenyl)piperidin-1-yl)propan-1-one | $^1$H NMR (CDCl$_3$, 400 MHz) δ 8.82 (dd, 1H), 8.30 (s, 1H), 7.97 (d, 1H), 7.95 (dd, 1H), 7.74 (m, 1H), 7.47 (s, 1H), 7.39 (s, 1H), 6.66 (d, 1H), 6.15 (d, 1H), 4.92-4.78 (m, 1H), 4.08-3.96 (m, 1H), 3.89 (s, 3H), 3.70-3.52 (m, 3H), 3.30 (septet, 1H), 3.24-3.12 (m, 1H), 3.06-2.92 (m, 1H), 2.86-2.60 (m, 3H), 2.36 (s, 3H), 1.96-1.82 (m, 2H), 1.72-1.46 (m, 2H), 1.33 (d, 6H), 1.29 (dd, 3H); MS(ES$^+$): 651.8 (M + 1)$^+$. | 37 |
| 66 | (S(S)-2-(dimethylamino)-1-(4-(4-(4-(2-(isopropylsulfonyl)phenylamino)pyrazolo[1,5-a][1,3,5]triazin-2-ylamino)-5-methoxy-2-methylphenyl)piperidin-1-yl)propan-1-one | MS (ES$^+$): 635.8 (M + 1)$^+$. | 32 |

TABLE 1-continued

| Ex # | Structure | Physical Data $^1$H NMR 400 MHz and/or MS (m/z) | IC$_{50}$ (nM) |
|---|---|---|---|
| 67 | 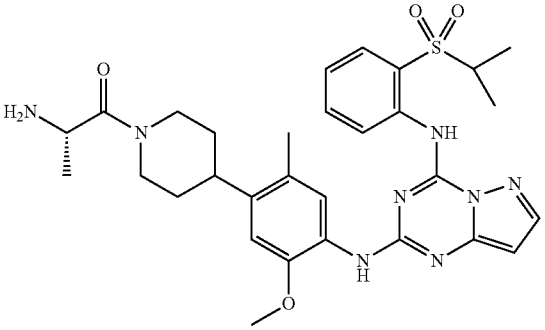<br>(S)-2-amino-1-(4-(4-(4-(2-(isopropylsulfonyl)phenylamino)pyrazolo[1,5-a][1,3,5]triazin-2-ylamino)-5-methoxy-2-methylphenyl)piperidin-1-yl)propan-1-one | $^1$H NMR (CDCl$_3$, 400 MHz) δ 8.82 (dd, 1H), 8.29 (s, 1H), 7.97 (d, 1H), 7.95 (dd, 1H), 7.74 (m, 1H), 7.46 (s, 1H), 7.34 (m, 1H), 6.67 (d, 1H), 6.14 (d, 1H), 4.83 (dm, 1H), 4.06-3.84 (m, 2H), 3.89 (s, 3H), 3.80-3.40 (s, br, 2H), 3.30 (septet, 1H), 3.24-3.10 (m, 1H), 3.06-2.90 (m, 1H), 2.78-2.64 (m, 1H), 2.36 (s, 3H), 1.96-1.78 (m, 2H), 1.72-1.46 (m, 2H), 1.33 (d, 6H), 1.31 (dd, 3H); MS (ES$^+$): 607.7 (M + 1)$^+$. | 40 |
| 68 | 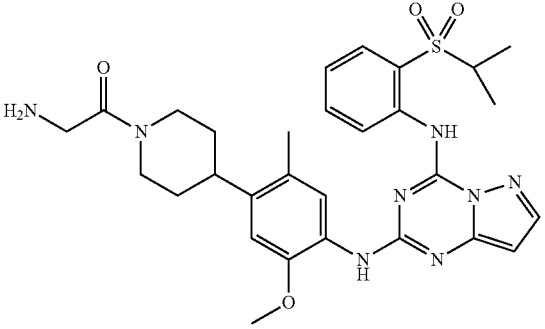<br>2-amino-1-(4-(4-(4-(2-(isopropylsulfonyl)phenylamino)pyrazolo[1,5-a][1,3,5]triazin-2-ylamino)-5-methoxy-2-methylphenyl)piperidin-1-yl)ethanone | $^1$H NMR (CDCl$_3$, 400 MHz) δ 8.83 (dd, 1H), 8.30 (s, 1H), 7.98 (d, 1H), 7.96 (dd, 1H), 7.74 (m, 1H), 7.46 (s, 1H), 7.34 (m, 1H), 6.67 (s, 1H), 6.15 (d, 1H), 4.82 (dm, 1H), 3.92-3.82 (m, 1H), 3.89 (s, 3H), 3.53 (m, 2H), 3.30 (septet, 1H), 3.18-3.06 (m, 1H), 3.04-2.92 (m, 1H), 2.78-2.66 (m, 1H), 2.36 (s, 3H), 1.90-1.78 (m, 2H), 1.72-1.48 (m, 2H), 1.33 (d, 6H); MS (ES$^+$): 593.7 (M + 1)$^+$. | 17 |
| 69 | 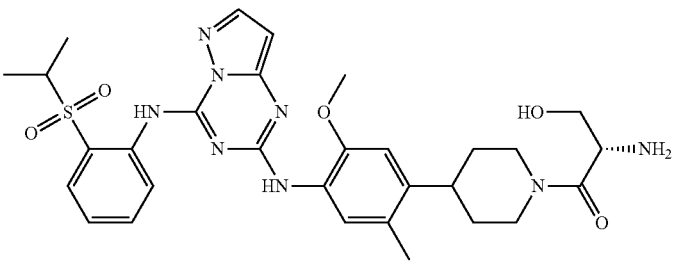<br>(S)-2-amino-3-hydroxy-1-(4-(4-(4-(2-(isopropylsulfonyl)phenylamino)pyrazolo[1,5-a][1,3,5]triazin-2-ylamino)-5-methoxy-2-methylphenyl)piperidin-1-yl)propan-1-one | $^1$H NMR (CDCl$_3$, 400 MHz): δ 8.82-8.84 (dd, 1H), 8.31 (broad s, 1H), 7.98-7.99 (d, 1H), 7.95-7.97 (dd, 1H), 7.73-7.77 (dd, 1H), 7.46 (s, 1H), 7.32-7.36 (dd, 1H), 6.67-6.68(d, 1H), 6.15-6.16 (d, 1H), 4.79-4.82 (m, 1H), 4.10-4.13 (m, 1H), 3.89 (s, 3H), 3.69-3.74(m, 1H), 3.51-3.57 (m, 1H), 3.26-3.33(m, 1H), 3.17-3.25(m, 1H), 2.95-3.01(m, 1H), 2.69-2.75(m, 1H), 2.36(s, 3H), 1.86-1.93(m, 2H), 1.54-1.70(m, 2H), 1.33-1.35(d, 6H); MS (ES$^+$): 623.2 (M + 1)$^+$. | 59 |

TABLE 1-continued

| Ex # | Structure | Physical Data $^1$H NMR 400 MHz and/or MS (m/z) | IC$_{50}$ (nM) |
|---|---|---|---|
| 70 | 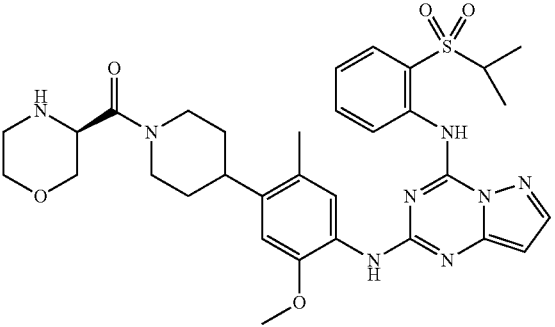<br>(R)-1-(4-(4-(4-(2-(isopropylsulfonyl)phenylamino)pyrazolo[1,5-a][1,3,5]triazin-2-ylamino)-5-methoxy-2-methylphenyl)piperidin-1-yl)(morpholin-3-yl)methanone | $^1$H NMR (CDCl$_3$, 400 MHz): δ 10.85 (broad s, 1H), 8.82-8.84 (dd, 1H), 8.30 (broad s, 1H), 7.98-7.99 (d, 1H), 7.95-7.98 (dd, 1H), 7.73-7.77 (dd, 1H), 7.46 (s, 1H), 7.32-7.36 (dd, 1H), 6.65-6.67(d, 1H), 6.15-6.16 (d, 1H), 4.78-4.82 (m, 1H), 4.10-4.13 (m, 1H), 3.93-4.04(m, 2H), 3.90 (s, 3H), 3.80-3.84 (m, 1H), 3.35-3.51(m, 2H), 3.27-3.34(m, 1H), 3.15-3.25(m, 1H), 2.94-3.12(m, 3H), 2.65-2.71(m, 1H), 2.36(s, 3H), 1.45-1.95(m, 5H), 1.33-1.35(d, 6H); MS (ES$^+$): 649.40 (M + 1)$^+$. | 35 |
| 71 | 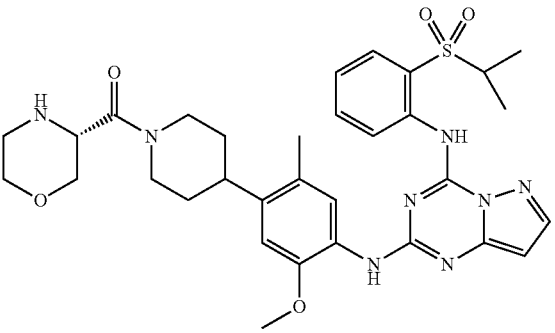<br>(S)-1-(4-(4-(4-(2-(isopropylsulfonyl)phenylamino)pyrazolo[1,5-a][1,3,5]triazin-2-ylamino)-5-methoxy-2-methylphenyl)piperidin-1-yl)(morpholin-3-yl)methanone | MS (ES$^+$): 649.3 (M + 1)$^+$. | 22 |
| 72 | 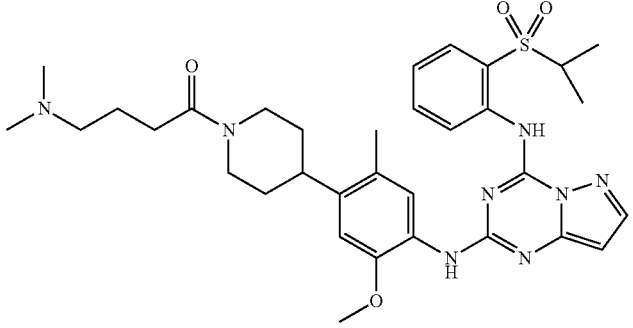<br>4-(dimethylamino)-1-(4-(4-(4-(2-(isopropylsulfonyl)phenylamino)pyrazolo[1,5-a][1,3,5]triazin-2-ylamino)-5-methoxy-2-methylphenyl)piperidin-1-yl)butan-1-one | MS (ES$^+$): 649.8 (M + 1)$^+$. | 58 |

TABLE 1-continued

| Ex # | Structure | Physical Data <br> ¹H NMR 400 MHz and/or MS (m/z) | IC$_{50}$ (nM) |
|---|---|---|---|
| 73 | 2-hydroxy-1-(4-(4-(4-(2-(isopropylsulfonyl)phenylamino)pyrazolo[1,5-a][1,3,5]triazin-2-ylamino)-5-methoxy-2-methylphenyl)piperidin-1-yl)ethanone | ¹H NMR (CDCl$_3$, 400 MHz) δ 10.86 (s, 1H), 8.82 (dd, 1H), 8.31 (s, 1H), 7.98 (d, 1H), 7.96 (dd, 1H), 7.74 (m, 1H), 7.47 (s, 1H), 7.34 (m, 1H), 6.66 (s, 1H), 6.15 (d, 1H), 4.79 (dm, 1H), 4.30-4.14 (m, 2H), 3.90 (s, 3H), 3.76-3.68 (m, 1H), 3.68-3.58 (m, 1H), 3.30 (septet, 1H), 3.20-3.08 (m, 1H), 3.04-2.94 (m, 1H), 2.84-2.76 (m, 1H), 2.36 (s, 3H), 1.92-1.83 (m, 2H), 1.73-1.53 (m, 2H), 1.33 (d, 6H); MS (ES$^+$): 594.7 (M + 1)$^+$. | 40 |
| 74 | 1-(4-(4-(4-(2-(isopropylsulfonyl)phenylamino)pyrazolo[1,5-a][1,3,5]triazin-2-ylamino)-5-methoxy-2-methylphenyl)piperidin-1-yl)-2-(2-methoxyethylamino)ethanone | MS (ES$^+$): 651.8 (M + 1)$^+$. | 28 |
| 75 | ((2R,4R)-4-hydroxypyrrolidin-2-yl)(4-(4-(4-(2-(isopropylsulfonyl)phenylamino)pyrazolo[1,5-a][1,3,5]triazin-2-ylamino)-5-methoxy-2-methylphenyl)piperidin-1-yl)methanone | MS (ES$^+$): 649.8 (M + 1)$^+$. | |

TABLE 1-continued

| Ex # | Structure | Physical Data $^1$H NMR 400 MHz and/or MS (m/z) | IC$_{50}$ (nM) |
|---|---|---|---|
| 76 | 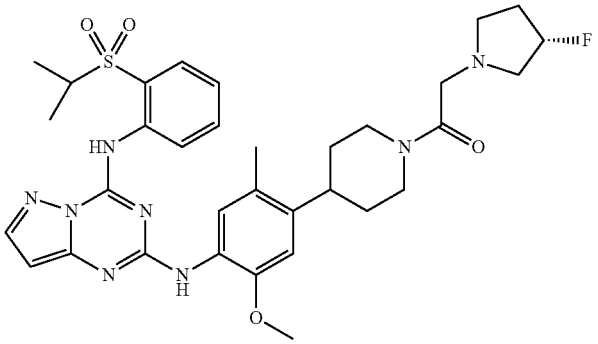<br>(S)-2-(3-fluoropyrrolidin-1-yl)-1-(4-(4-(4-(2-(isopropylsulfonyl)phenylamino) pyrazolo[1,5-a][1,3,5]triazin-2-ylamino)-5-methoxy-2-methylphenyl)piperidin-1-yl)ethanone | $^1$H NMR (CDCl$_3$, 400 MHz) δ 10.84 (s, 1H), 8.82 (dd, 1H), 8.28 (s, 1H), 7.97 (d, 1H), 7.96 (dd, 1H), 7.74 (m, 1H), 7.46 (s, 1H), 7.34 (m, 1H), 6.68 (d, 1H), 6.14 (d, 1H), 5.20 (dm, 1H), 4.78 (dm, 1H), 4.16 (m, 1H), 3.88 (d, 3H), 3.62-3.24 (m, 3H), 3.20-2.84 (m, 4H), 2.74-2.52 (m, 2H), 2.35 (s, 3H), 2.30-1.98 (m, 2H), 1.96-1.48 (m, 5H), 1.33 (d, 6H); MS (ES$^+$): 665.8 (M + 1)$^+$. | 75 |
| 77 | 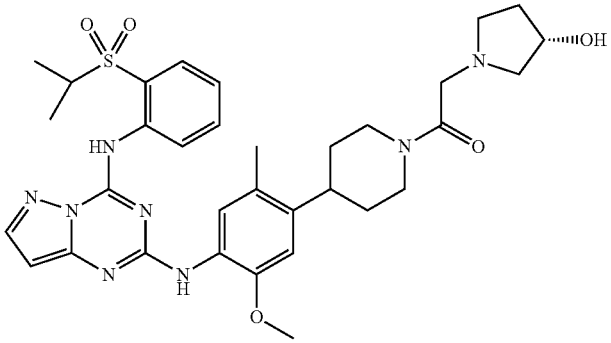<br>(S)-2-(3-hydroxypyrrolidin-1-yl)-1-(4-(4-(4-(2-(isopropylsulfonyl)phenylamino) pyrazolo[1,5-a][1,3,5]triazin-2-ylamino)-5-methoxy-2-methylphenyl)piperidin-1-yl)ethanone | MS (ES$^+$): 663.8 (M + 1)$^+$. | 36 |
| 78 | 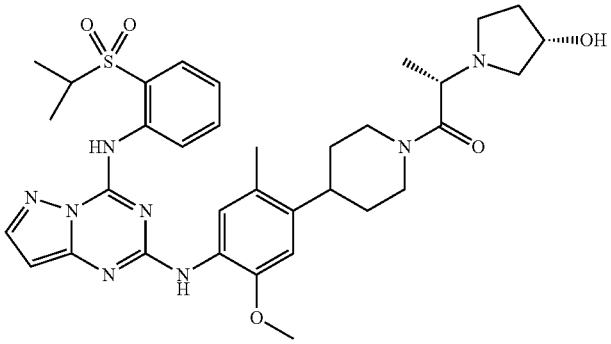<br>(S)-2-((S)-3-hydroxypyrrolidin-1-yl)-1-(4-(4-(4-(2-(isopropylsulfonyl)phenylamino) pyrazolo[1,5-a][1,3,5]triazin-2-ylamino)-5-methoxy-2-methylphenyl)piperidin-1-yl)propan-1-one | MS (ES$^+$): 677.8 (M + 1)$^+$. | 36 |

TABLE 1-continued

| Ex # | Structure | Physical Data $^1$H NMR 400 MHz and/or MS (m/z) | IC$_{50}$ (nM) |
|---|---|---|---|
| 79 | (S)-2-((R)-3-hydroxypyrrolidin-1-yl)-1-(4-(4-(4-(2-(isopropylsulfonyl)phenylamino)pyrazolo[1,5-a][1,3,5]triazin-2-ylamino)-5-methoxy-2-methylphenyl)piperidin-1-yl)propan-1-one | $^1$H NMR (CDCl$_3$, 400 MHz) δ 10.84 (s, 1H), 8.82 (dd, 1H), 8.29 (d, 1H), 7.97 (d, 1H), 7.95 (dd, 1H), 7.74 (m, 1H), 7.46 (s, 1H), 7.34 (m, 1H), 6.67 (dd, 1H), 6.14 (d, 1H), 4.88-4.76 (m, 1H), 4.38-4.14 (m, 2H), 3.89 (s, 3H), 3.84-3.68 (m, 1H), 3.30 (septet, 1H), 3.24-3.04 (m, 2H), 3.02-2.86 (m, 3H), 2.84-2.72 (m, 1H), 2.72-2.56 (m, 2H), 2.35 (s, 3H), 2.18-1.98 (m, 1H), 1.96-1.78 (m, 3H), 1.70-1.48 (m, 2H), 1.44-1.28 (m, 3H), 1.33 (d, 6H); MS (ES$^+$): 677.8 (M + 1)$^+$. | 38 |
| 80 | (S)-1-(4-(4-(4-(2-(isopropylsulfonyl)phenylamino)pyrazolo[1,5-a][1,3,5]triazin-2-ylamino)-5-methoxy-2-methylphenyl)piperidin-1-yl)-2-(pyrrolidin-1-yl)propan-1-one | $^1$H NMR (CDCl$_3$, 400 MHz) δ 10.82 (s, 1H), 8.83 (dd, 1H), 8.29 (s, 1H), 7.98 (d, 1H), 7.95 (dd, 1H), 7.74 (m, 1H), 7.46 (s, 1H), 7.34 (m, 1H), 6.67 (s, 1H), 6.15 (d, 1H), 4.90-4.78 (m, 1H), 4.62-4.44 (m, 1H), 3.89 (s, 3H), 3.64-3.48 (m, 1H), 3.30 (septet, 1H), 3.18-3.04 (m, 1H), 3.02-2.90 (m, 1H), 2.78-2.54 (m, 5H), 2.36 (s, 3H), 1.90-1.72 (m, 6H), 1.70-1.46 (m, 2H), 1.40-1.22 (m, 3H), 1.33 (d, 6H); MS (ES$^+$): 661.3 (M + 1)$^+$. | 33 |
| 81 | (R)-2-(azetidin-1-yl)-1-(4-(4-(4-(2-(isopropylsulfonyl)phenylamino)pyrazolo[1,5-a][1,3,5]triazin-2-ylamino)-5-methoxy-2-methylphenyl)piperidin-1-yl)propan-1-one | MS (ES$^+$): 647.3 (M + 1)$^+$. | 26 |

TABLE 1-continued

| Ex # | Structure | Physical Data ¹H NMR 400 MHz and/or MS (m/z) | IC$_{50}$ (nM) |
| --- | --- | --- | --- |
| 82 | N5-(2-isopropoxy-5-methyl-4-(piperidin-4-yl)phenyl)-N7-(2-(isopropylsulfonyl)phenyl)pyrazolo[1,5-a]pyrimidine-5,7-diamine | ¹H NMR (CDCl$_3$, 400 MHz) δ 7.88-7.95 (m, 3H), 7.73-7.75 (d, 1H), 7.61-7.64 (m,1H), 7.23-7.26 (m, 1H), 6.88 (s, 1H), 6.75 (s, 1H), 6.17-6.18 (d, 1H), 6.09(s, 1H), 4.46-4.54 (m. 1H), 3.30-3.34 (m, 2H), 3.12-3.21 (m, 1H), 2.79-2.83(m, 3H), 2.27 (s, 3H), 1.77-1.79 (m, 4H), 1.15-1.28(m, 12H); MS (ES$^+$): 563.28 (M + 1)$^+$. | |
| 83 | N4-(2-(isopropylsulfonyl)phenyl)-N2-(2-methoxy-5-methyl-4-(1-(tetrahydro-2H-pyran-4-yl)piperidin-4-yl)phenyl)pyrazolo[1,5-a][1,3,5]triazine-2,4-diamine | MS (ES+): 620.4 (M + 1)+. | 23 |
| 84 | N4-(2-(isopropylsulfonyl)phenyl)-N2-(2-methoxy-5-methyl-4-(1-(tetrahydro-2H-thiopyran-4-yl)piperidin-4-yl)phenyl)pyrazolo[1,5-a][1,3,5]triazine-2,4-diamine | MS (ES$^+$): 636.2 (M + 1)$^+$. | 25 |

TABLE 1-continued

| Ex # | Structure | Physical Data<br>¹H NMR 400 MHz and/or MS<br>(m/z) | IC$_{50}$<br>(nM) |
|---|---|---|---|
| 85 | (R)-(6,6-dimethylmorpholin-3-yl)(4-(4-(4-(2-(isopropylsulfonyl)phenylamino) pyrazolo[1,5-a][1,3,5]triazin-2-ylamino)-5-methoxy-2-methylphenyl)piperidin-1-yl)methanone | MS (ES⁺): 677.3 (M + 1)⁺. | 34 |
| 86 | (R)-2-amino-3-hydroxy-1-(4-(4-(4-(2-(isopropylsulfonyl)phenylamino)pyrazolo[1,5-a][1,3,5]triazin-2-ylamino)-5-methoxy-2-methylphenyl)piperidin-1-yl)propan-1-one | ¹H NMR (CDCl₃, 400 MHz): δ 8.82-8.84 (dd, 1H), 8.31 (broad s, 1H), 7.98-7.99 (d, 1H), 7.95-7.97 (dd, 1H), 7.73-7.77 (dd, 1H), 7.46 (s, 1H), 7.32-7.36 (dd, 1H), 6.67-6.68(d, 1H), 6.15-6.16 (d, 1H), 4.79-4.82 (m, 1H), 4.10-4.13 (m, 1H), 3.89 (s, 3H), 3.69-3.74(m, 1H), 3.51-3.57 (m, 1H), 3.26-3.33(m, 1H), 3.17-3.25(m, 1H), 2.95-3.01(m, 1H), 2.69-2.75(m, 1H), 2.36(s, 3H), 1.86-1.93(m, 2H), 1.54-1.70(m, 2H), 1.33-1.35(d, 6H); MS (ES⁺): 623.2 (M + 1)⁺. | 34 |
| 87 | (S)-(6,6-dimethylmorpholin-3-yl)(4-(4-(4-(2-(isopropylsulfonyl)phenylamino) pyrazolo[1,5-a][1,3,5]triazin-2-ylamino)-5-methoxy-2-methylphenyl)piperidin-1-yl)methanone | MS (ES+): 677.3 (M + 1)+. | 29 |

TABLE 1-continued

| Ex # | Structure | Physical Data $^1$H NMR 400 MHz and/or MS (m/z) | IC$_{50}$ (nM) |
|---|---|---|---|
| 88 | 1-(4-(4-(4-(2-(isopropylsulfonyl)phenylamino)pyrazolo[1,5-a][1,3,5]triazin-2-ylamino)-5-methoxy-2-methylphenyl)piperidin-1-yl)-2-morpholinoethanone | 1H NMR (CDCl3, 400 MHz) δ 10.85 (s, 1H), 8.83 (dd, 1H), 8.30 (s, 1H), 7.98 (d, 1H), 7.96 (dd, 1H), 7.74 (m, 1H), 7.46 (s, 1H), 7.34 (m, 1H), 6.66 (s, 1H), 6.15 (d, 1H), 4.79 (dm, 1H), 4.20 (dm, 1H), 3.87 (s, 3H), 3.78-3.71 (m, 4H), 3.36-3.24 (m, 2H), 3.24-3.08 (m, 2H), 3.04-2.92 (m, 1H), 2.73-2.63 (m, 1H), 2.63-2.48 (m, 4H), 2.36 (s, 3H), 1.92-1.78 (m, 2H), 1.68-1.54 (m, 2H), 1.33 (d, 6H); MS (ES+): 663.3 (M + 1)+. | 47 |
| 89 | 1-(azetidin-1-yl)-3-(4-(4-(4-(2-(isopropylsulfonyl)phenylamino)pyrazolo[1,5-a][1,3,5]triazin-2-ylamino)-5-methoxy-2-methylphenyl)piperidin-1-yl)propan-1-one | MS (ES+): 647.3 (M + 1)+. | 15 |
| 90 | 3-(4-(4-(4-(2-(isopropylsulfonyl)phenylamino)pyrazolo[1,5-a][1,3,5]triazin-2-ylamino)-5-methoxy-2-methylphenyl)piperidin-1-yl)-N-methylpropanamide | 1H NMR (CDCl3, 400 MHz) δ 10.85 (s, 1H), 8.83 (dd, 1H), 8.28 (s,, 1H), 7.98 (d, 1H), 7.96 (dd, 1H), 7.89 (s, 1H), 7.74 (m, 1H), 7.46 (s, 1H), 7.34 (m, 1H), 6.77 (s, 1H), 6.15 (d, 1H), 3.92 (s, 3H), 3.31 (septet, 1H), 3.13 (dm, 2H), 2.83 (d, 3H), 2.80-2.65 (m, 2H), 2.48-2.41 (m, 2H), 2.34 (s, 3H), 2.22-2.10 (m, 2H), 1.92-1.58 (m, 5H), 1.34 (d, 6H); MS (ES+): 621.3 (M + 1)+. | 13 |
| 91 | 2-(4-(4-(4-(2-(isopropylsulfonyl)phenylamino)pyrazolo[1,5-a][1,3,5]triazin-2-ylamino)phenyl)piperidin-1-yl)propanamide | MS (ES+): 549.2 (M + 1)+. | 128 |

TABLE 1-continued

| Ex # | Structure | Physical Data<br>¹H NMR 400 MHz and/or MS (m/z) | IC$_{50}$ (nM) |
|---|---|---|---|
| 92 | 3-(4-(4-(4-(2-(isopropylsulfonyl)phenylamino)pyrazolo[1,5-a][1,3,5]triazin-2-ylamino)phenyl)piperidin-1-yl)propanamide | MS (ES+): 563.3 (M + 1)+. | 130 |
| 93 | 2-(azetidin-1-yl)-1-(4-(4-(4-(2-(isopropylsulfonyl)phenylamino)pyrazolo[1,5-a][1,3,5]triazin-2-ylamino)phenyl)piperidin-1-yl)ethanone | MS (ES+): 589.3 (M + 1)+. | 132 |
| 94 | (S)-2-amino-1-(4-(4-(4-(2-(isopropylsulfonyl)phenylamino)pyrazolo[1,5-a][1,3,5]triazin-2-ylamino)-5-methoxy-2-methylphenyl)piperidin-1-yl)-3-methoxypropan-1-one | 1H NMR (CDCl3, 400 MHz) δ 8.82 (dd, 1H), 8.29 (s, 1H), 7.97 (d, 1H), 7.95 (dd, 1H), 7.74 (m, 1H), 7.46 (s, 1H), 7.34 (m, 1H), 6.68 (d, 1H), 6.14 (d, 1H), 4.88-4.76 (m, 1H), 4.20-4.00 (m, 2H), 3.89 (s, 3H), 3.58-3.50 (m, 1H), 3.50-3.34 (m, 1H), 3.38 (s, 3H), 3.30 (septet, 1H), 3.24-3.12 (m, 1H), 3.04-2.92 (m, 1H), 2.78-2.64 (m, 1H), 2.35 (s, 3H), 1.94-1.78 (m, 2H), 1.74-1.54 (m, 2H), 1.33 (d, 6H); MS (ES+): 637.3 (M + 1)+. | 16 |
| 95 | (S)-2-((2-hydroxyethyl)(methyl)amino)-1-(4-(4-(4-(2-(isopropylsulfonyl)phenylamino)pyrazolo[1,5-a][1,3,5]triazin-2-ylamino)-5-methoxy-2-methylphenyl)piperidin-1-yl)propan-1-one | 1H NMR (CDCl3, 400 MHz) δ 10.82 (s, 1H), 8.82 (dd, 1H), 8.29 (s, 1H), 7.98 (d, 1H), 7.96 (dd, 1H), 7.74 (m, 1H), 7.46 (s, 1H), 7.34 (m, 1H), 6.69 (d, 1H), 6.15 (d, 1H), 4.92-4.76 (m, 1H), 4.26-4.12 (m, 1H), 3.89 (s, 3H), 3.78-3.68 (m, 1H), 3.64-3.56 (m, 2H), 3.30 (septet, 1H), 3.26-3.08 (m, 1H), 3.04-2.90 (m, 1H), 2.82-2.58 (m, 3H), 2.38-2.28 (m, 3H), 2.35 (s, 3H), 1.94-1.80 (m, 2H), 1.72-1.46 (m, 3H), 1.33 (d, 6H), 1.28-1.21 (m, 3H); MS (ES+): 665.3 (M + 1)+. | 22 |

TABLE 1-continued

| Ex # | Structure | Physical Data ¹H NMR 400 MHz and/or MS (m/z) | IC$_{50}$ (nM) |
|---|---|---|---|
| 96 | (R)-1-(4-(4-(4-(2-(isopropylsulfonyl)phenylamino)pyrazolo[1,5-a][1,3,5]triazin-2-ylamino)-5-methoxy-2-methylphenyl)piperidin-1-yl)-2-(pyrrolidin-1-yl)propan-1-one | 1H NMR (CDCl3, 400 MHz) δ 10.82 (s, 1H), 8.83 (dd, 1H), 8.29 (s, 1H), 7.98 (d, 1H), 7.95 (dd, 1H), 7.74 (m, 1H), 7.46 (s, 1H), 7.34 (m, 1H), 6.67 (s, 1H), 6.15 (d, 1H), 4.90-4.78 (m, 1H), 4.62-4.44 (m, 1H), 3.89 (s, 3H), 3.64-3.48 (m, 1H), 3.30 (septet, 1H), 3.18-3.04 (m, 1H), 3.02-2.90 (m, 1H), 2.78-2.54 (m, 5H), 2.36 (s, 3H), 1.90-1.72 (m, 6H), 1.70-1.46 (m, 2H), 1.40-1.22 (m, 3H), 1.33 (d, 6H); MS (ES+): 661.3 (M + 1)+. | 32 |
| 97 | (R)-2-(2-hydroxyethylamino)-1-(4-(4-(4-(2-(isopropylsulfonyl)phenylamino)pyrazolo[1,5-a][1,3,5]triazin-2-ylamino)-5-methoxy-2-methylphenyl)piperidin-1-yl)propan-1-one | 1H NMR (CDCl3, 400 MHz) δ 8.82 (dd, 1H), 8.30 (s, 1H), 7.97 (d, 1H), 7.95 (dd, 1H), 7.74 (m, 1H), 7.47 (s, 1H), 7.39 (s, 1H), 6.66 (d, 1H), 6.15 (d, 1H), 4.92-4.78 (m, 1H), 4.08-3.96 (m, 1H), 3.89 (s, 3H), 3.70-3.52 (m, 3H), 3.30 (septet, 1H), 3.24-3.12 (m, 1H), 3.06-2.92 (m, 1H), 2.86-2.60 (m, 3H), 2.36 (s, 3H), 1.96-1.82 (m, 2H), 1.72-1.46 (m, 2H), 1.33 (d, 6H), 1.29 (dd, 3H); MS (ES+): 651.3 (M + 1)+. | 32 |
| 98 | (R)-2-((2-hydroxyethyl)(methyl)amino)-1-(4-(4-(4-(2-(isopropylsulfonyl)phenylamino)pyrazolo[1,5-a][1,3,5]triazin-2-ylamino)-5-methoxy-2-methylphenyl)piperidin-1-yl)propan-1-one | 1H NMR (CDCl3, 400 MHz) δ 10.82 (s, 1H), 8.82 (dd, 1H), 8.29 (s, 1H), 7.98 (d, 1H), 7.96 (dd, 1H), 7.74 (m, 1H), 7.46 (s, 1H), 7.34 (m, 1H), 6.69 (d, 1H), 6.15 (d, 1H), 4.92-4.76 (m, 1H), 4.26-4.12 (m, 1H), 3.89 (s, 3H), 3.78-3.68 (m, 1H), 3.64-3.56 (m, 2H), 3.30 (septet, 1H), 3.26-3.08 (m, 1H), 3.04-2.90 (m, 1H), 2.82-2.58 (m, 3H), 2.38-2.28 (m, 3H), 2.35 (s, 3H), 1.94-1.80 (m, 2H), 1.72-1.46 (m, 3H), 1.33 (d, 6H), 1.28-1.21 (m, 3H); MS (ES+): 665.3 (M + 1)+. | 13 |
| 99 | 3-(diethylamino)-1-(4-(4-(4-(2-(isopropylsulfonyl)phenylamino)pyrazolo[1,5-a][1,3,5]triazin-2-ylamino)-5-methoxy-2-methylphenyl)piperidin-1-yl)propan-1-one | 1H NMR (CDCl3, 400 MHz) δ 10.79 (s, 1H), 8.82 (dd, 1H), 8.29 (s, 1H), 7.97 (d, 1H), 7.95 (dd, 1H), 7.74 (m, 1H), 7.46 (s, 1H), 7.34 (m, 1H), 6.68 (s, 1H), 6.14 (d, 1H), 4.82 (dm, 1H), 4.03 (dm, 1H), 3.89 (s, 3H), 3.30 (septet, 1H), 3.22-3.12 (m, 1H), 3.00-2.84 (m, 3H), 2.70-2.58 (m, 7H), 2.35 (s, 3H), 1.90-1.76 (m, 2H), 1.70-1.52 (m, 2H), 1.33 (d, 6H), 1.10 (t, 6H); MS (ES+): 663.3 (M + 1)+. | 35 |

| Ex # | Structure | Physical Data ¹H NMR 400 MHz and/or MS (m/z) | IC$_{50}$ (nM) |
|---|---|---|---|
| 100 | 1-(4-(4-(4-(2-(isopropylsulfonyl)phenylamino)pyrazolo[1,5-a][1,3,5]triazin-2-ylamino)-5-methoxy-2-methylphenyl)piperidin-1-yl)-4-(pyrrolidin-1-yl)butan-1-one | MS (ES+): 675.3 (M + 1)+. | 33 |
| 101 | 1-(4-(4-(4-(2-(isopropylsulfonyl)phenylamino)pyrazolo[1,5-a][1,3,5]triazin-2-ylamino)-5-methoxy-2-methylphenyl)piperidin-1-yl)-4-morpholinobutan-1-one | MS (ES+): 691.3 (M + 1)+. | 31 |
| 102 | 2-(dipropylamino)-1-(4-(4-(4-(2-(isopropylsulfonyl)phenylamino)pyrazolo[1,5-a][1,3,5]triazin-2-ylamino)-5-methoxy-2-methylphenyl)piperidin-1-yl)ethanone | 1H NMR (CDCl3, 400 MHz) δ 10.84 (s, 1H), 8.33 (dd, 1H), 8.28 (s, 1H), 7.97 (d, 1H), 7.95 (dd, 1H), 7.74 (m, 1H), 7.46 (s, 1H), 7.34 (m, 1TI), 6.68 (s, 1H), 6.14 (d, 1H), 4.77 (dm, 1H), 4.31 (dm, 1H), 3.88 (s, 3H), 3.52-3.43 (m, 1H), 3.38-3.24 (m, 2H), 3.16-3.06 (M, 1H), 3.02-2.90 (m, 1H), 2.73-2.63 (m, 1H), 2.62-2.45 (m, 4H), 2.35 (s, 3H), 1.83 (dm, 2H), 1.74-1.59 (m, 2H), 1.58-1.46 (m, 4H), 1.33 (d, 6H), 0.91 (t, 6H); MS (ES+): 677.4 (M + 1)+. | 49 |
| 103 | 1-(4-(4-(4-(2-(isopropylsulfonyl)phenylamino)pyrazolo[1,5-a][1,3,5]triazin-2-ylamino)-5-methoxy-2-methylphenyl)piperidin-1-yl)-2-(propylamino)ethanone | 1H NMR (CDCl3, 400 MHz) δ 8.82 (dd, 1H), 8.29 (s, 1H), 7.97 (d, 1H), 7.95 (dd, 1H), 7.74 (m, 1H), 7.46 (s, 1H), 7.33 (m, 1H), 6.69 (s, 1H), 6.14 (d, 1H), 4.78 (dm, 1H), 3.95-3.81 (m, 1H), 3.90 (s, 3H), 3.65 (q, 2H), 3.30 (septet, 1H), 3.22-3.10 (m, 1H), 3.02-2.92 (m, 1H), 2.78-2.68 (m, 3H), 2.35 (s, 3H), 1.92-1.76 (m, 2H), 1.74-1.50 (m, 5H), 1.33 (d, 6H), 0.98 (t, 3H); MS (ES+): 635.3 (M + 1)+. | 16 |

TABLE 1-continued

| Ex # | Structure | Physical Data ¹H NMR 400 MHz and/or MS (m/z) | IC$_{50}$ (nM) |
|---|---|---|---|
| 104 | 1-(4-(4-(4-(2-(isopropylsulfonyl)phenylamino)pyrazolo[1,5-a][1,3,5]triazin-2-ylamino)-5-methoxy-2-methylphenyl)piperidin-1-yl)-3-(pyrrolidin-1-yl)propan-1-one | MS (ES+): 661.3 (M + 1)+. | 49 |
| 105 | 2-(ethylamino)-1-(4-(4-(4-(2-(isopropylsulfonyl)phenylamino)pyrazolo[1,5-a][1,3,5]triazin-2-ylamino)-5-methoxy-2-methylphenyl)piperidin-1-yl)ethanone | 1H NMR (CDCl3, 400 MHz) δ 8.83 (dd, 1H), 8.30 (s, 1H), 7.98 (d, 1H), 7.96 (dd, 1H), 7.74 (m, 1H), 7.46 (s, 1H), 7.34 (m, 1H), 6.67 (s, 1H), 6.15 (d, 1H), 4.82 (dm, 1H), 3.97-3.84 (m, 1H), 3.89 (s, 3H), 3.50 (q, 2H), 3.30 (septet, 1H), 3.20-3.08 (m, 1H), 3.02-2.92 (m, 1H), 2.76-2.64 (m, 3H), 2.36 (s, 3H), 1.90-1.78 (m, 2H), 1.70-1.52 (m, 3H), 1.34 (d, 6H), 1.16 (t, 3H). MS (ES+): 621.3 (M + 1)+. | 15 |
| 106 | 3-hydroxy-2-(hydroxymethyl)-1-(4-(4-(4-(2-(isopropylsulfonyl)phenylamino)pyrazolo[1,5-a][1,3,5]triazin-2-ylamino)-5-methoxy-2-methylphenyl)piperidin-1-yl)-2-methylpropan-1-one | MS (ES+): 652.3 (M + 1)+. | 16 |
| 107 | 2-(ethylamino)-1-(4-(5-hydroxy-4-(4-(2-(isopropylsulfonyl)phenylamino)pyrazolo[1,5-a][1,3,5]triazin-2-ylamino)-2-methylphenyl)piperidin-1-yl)ethanone | 1H NMR (CDCl3, 400 MHz) δ 8.75 (dd, 1H), 7.96 (dd, 1H), 7.95 (d, 1H), 7.74 (m, 1H), 7.36 (m, 1H), 7.14 (s, 1H), 7.07 (s, 1H), 6.82 (s, 1H), 6.11 (d, 1H), 4.77 (dm, 1H), 3.87 (dm, 1H), 3.52 (q, 1H), 3.29 (septet, 1H), 3.16-3.04 (m, 1H), 2.92-2.80 (m, 1H), 2.78-2.62 (m, 3H), 2.26 (s, 3H), 1.88-1.76 (m, 2H), 1.66-1.50 (m, 2H), 1.33 (d, 6H), 1.19 (t, 3H); MS (ES+): 607.3 (M + 1)+. | |

TABLE 1-continued

| Ex # | Structure | Physical Data $^1$H NMR 400 MHz and/or MS (m/z) | IC$_{50}$ (nM) |
|---|---|---|---|
| 108 | (4-(4-(4-(2-(isopropylsulfonyl)phenylamino)pyrazolo[1,5-a][1,3,5]triazin-2-ylamino)-5-methoxy-2-methylphenyl)piperidin-1-yl)(3-methyloxetan-3-yl)methanone | MS (ES+): 634.3 (M + 1)+. | |
| 109 | 1-(4-(5-ethoxy-4-(4-(2-(isopropylsulfonyl)phenylamino)pyrazolo[1,5-a][1,3,5]triazin-2-ylamino)-2-methylphenyl)piperidin-1-yl)-2-(ethylamino)ethanone | MS (ES+): 635.3 (M + 1)+. | |
| 110 | 2-(dimethylamino)-1-(4-(4-(4-(2-(isopropylsulfonyl)phenylamino)pyrazolo[1,5-a][1,3,5]triazin-2-ylamino)-5-methoxy-2-methylphenyl)piperidin-1-yl)ethanone | 1H NMR (CDCl3, 400 MHz) δ 10.84 (s, 1H), 8.83 (dd, 1H), 8.29 (s, 1H), 7.98 (d, 1H), 7.96 (dd, 1H), 7.74 (m, 1H), 7.45 (s, 1H), 7.34 (m, 1H), 6.68 (s, 1H), 6.15 (d, 1H), 4.79 (dm, 1H), 4.37 (dm, 1H), 3.88 (s, 3H), 3.40-3.20 (m, 2H), 3.16-3.04 (m, 1H), 3.02-2.90 (m, 1H), 2.72-2.62 (m, 4H), 2.36 (s, 3H), 1.88-1.78 (m, 2H), 1.70-1.54 (m, 4H), 1.34 (d, 6H), 1.07 (t, 6H);MS (ES+): 649.3 (M + 1)+. | 16 |

Assays

Compounds of the present invention may be assessed for their ability to inhibit ALK using assays described below, as well as other assays known in the art.

Ba/F3 Cell Line Panel and Reagents

Ba/F3 is a murine IL-3-dependent pro-B lymphoma cell line. Parental Ba/F3 cells are used to generate a panel of sublines whose proliferation and survival is rendered IL-3-independent by stable transduction with individual tyrosine kinases activated by fusion with the amino-terminal portion of TEL (amino acid 1-375) or BCR. In order to generate Ba/F3 cell lines transformed by Tel-Tyrosine Kinase (TK) fusions, parental Ba/F3 cells are infected with a retrovirus harboring each kinase domain and subjected to puromycin selection and IL-3 withdrawal to obtain IL-3-independent, transformed Ba/F3 cells.

Each transformed Ba/F3 cells are cultured in RPMI-1640 media (Gibco Cat #11875093, Carlsbad, Calif.) supplemented with 10% FBS (Hyclone Cat #SV30014.03, Logan, Utah), 4.5 g/L glucose (Sigma #G5400, St. Louis, Mo.), 1.5 g/L sodium bicarbonate (Biowhittaker #17-613E, Walkersville, Md.) and Pen/Strep (Gibco #10378-016, Carlsbad, Calif.). Cells are splitted twice weekly.

Ba/F3 Cell Viability Inhibition Assay

The potency of test compounds against various Tel-TK transformed Ba/F3 lines is determined as follows. Exponentially growing BaF3 Tel-TK cells are diluted in fresh medium to 75,000 cells/mL and seeded into 384-well plates (3750 cells/well) at 50 µL/well using a µFill liquid dispenser (BioTek, Winooski, Vt., USA). Duplicate plates are run for each cell line. Test and control compounds are serially diluted with DMSO and arrayed in a polypropylene 384-well plate. 50 nL of compound is transferred into the assay plates using a pin-transfer device, and the plates are incubated at 37° C. (5% CO2) for 48 hours. 25 µL Bright-Glo (Promega, Madison, Wis., USA) is added and luminescence is quantified using Analyst GT (Perkin Elmer, Wellesley, Mass.). Custom curve-fitting software is used to produce a logistic fit of percent cell viability as a function of the logarithm of inhibitor concentration. The $IC_{50}$ is interpolated as the concentration of compound needed to reduce cell viability to 50% of a DMSO control. Parental Ba/F3 cells that are maintained and cultured in presence of IL-3 (1 ng/ml in final) are diluted in fresh medium containing IL-3 (1 ng/ml in final) to 75,000 cells/mL following the same procedure as described above.

Kapas 299 Cellular Assay

Luciferized Karpas 299 (Karpas299-Luc) is generated by infecting retrovirus encoding luciferase gene, and cultured in RPMI-1649 medium supplemented with 10% FBS, 1% P/S/L-Glu. At day 1, cells are harvested and resuspended at density of 150,000 cells/ml (cell number is measured using ViCell (BD). Cells are dispensed from a diluted suspension into a 384-well assay plate in 50 µl volume using µFill (BioTEK). Serially diluted compounds (in DMSO) are transferred into plate using 50 nL pinhead. Assay plates are incubated at 37° C. for 48 hours. At day 4, 25 µl/well of Bright-Glo reagent (Promega) is added using µFill (Bio-TEK). Within 30 minutes, a luciferase signal is measured using Analyst GT in default setting for luminescence detection.

Enzymatic HTRF Assay

IGF-1R and INSR (insulin receptor) are purchased from Upstate. Following reagents are prepared in-house; 10× kinas buffer (KB) (200 mM Tris (pH 7.0), 100 mM $MgCl_2$, 30 mM $MnCl_2$, 50 nM $NaVO_4$), 10 mM ATP, 100 mg/ml BSA, 0.5 M EDTA, 4 M KF. Proxiplate-384 from Perkin-Elmer is used for set up assay. All the HTRF reagents including substrate (Biotin-poly-GT (61GT0BLB), Mab PT66-K, (61T66KLB), Streptavidin-Xr$^{ent}$ (611SAXLB)) are purchased from CISUS, Inc.

The substrate/ATP mix is prepared by adding ATP (final concentration, 3 µM) and biotinylated poly-GT (final concentration, 10 ng/µl) into 1× KB, and dispensed into Proxiplate-384 at 5 µl/well using µFill (Bio-TEK). Serially diluted compounds (in DMSO) are transferred into plate using 50 nL pinhead. 5 µL of prepared Enzyme mix (enzyme (final concentration, 5 ng/µl), mixed with BSA and DTT in 1× KB) is added to initiate kinase reaction using µFill (Bio-TEK). Assay plate is incubated at room temperature for 2 hours. Detection mix is prepared by adding both Mab PT66-K and Streptavidin-XL$^{ent}$ into 0.5× KB solution containing KF (final concentration, 125 mM), EDTA (final concentration, 50 mM) and BSA (final concentration, 100 µg/ml) in. At the end of reaction, 10 µL of detection mix is added and incubated for 30 minutes at room temperature before measurement. HTRF signal is detected using Analyst-GT (molecular dynamic).

Reporter Assay in U2OS Cells using RE1-pGL3 for IGF1-S3-5 or INSR-S3-5

Seed 10M cells/T175 Flask in Mc Coy 10% FBS and 4 days later, suck off media and add fresh media. Next day (5 days after seeding), trypsinize cells, wash once with PBS, then resuspend cells in Mc-Coy media 4% delipidated serum with P/S/G. Count cells and dilute to 400,000 cells/ml.

For 95 ml of cells (400000 cells/ml (40M)), prepare the following DNA/Fugene6 mix: 5 ml Mc-Coy media without serum; 120 µg DNA mix (20 µg IGF1R-S3-5 or INSR-S3-5+100 µg RE1-pGL3); and 240 µL Fugene6 reagent. Incubate DNA/Fugene6 mix for 15 min before adding it to cells in 4% delipidated serum. Dispense 50 µL/well in 384 well plate. 22-24 h later, add 50 nL of serially diluted compounds using pinhead. 30 min later, add 2 µL of 26× IGF1 (or 100× Insulin) dose diluted in Mc-Coy 4% delipidated serum using µ-Fill. 30 hours later, add 25 µL 100% bright-glo and read on Analyst-GT for measuring luminescence.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

The invention claimed is:

1. A compound of Formula (1):

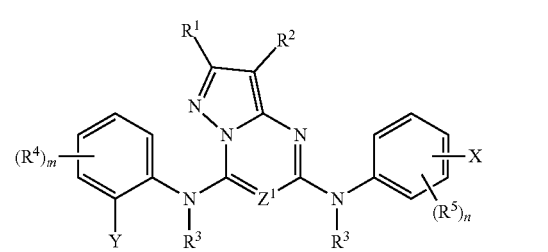

or a physiologically acceptable salt thereof;

X is a $C_{3-12}$ carbocyclic ring, $C_{6-10}$ aryl, or a 5-10 membered heteroaryl or 4-10 membered heterocyclic ring containing $NR^6$, O or S, each of which is optionally substituted with 1-3 $R^{5'}$ groups;

alternatively, X is a $C_{1-6}$ alkyl, $C_{2-6}$ alkenyl or $C_{2-6}$ alkynyl, each of which may be optionally substituted with halo, amino, hydroxyl or alkoxy; or X is $(CR_2)_{0-4}CO_2R^7$ or $(CR_2)_{0-4}CR(NRR^7)(CO_2R^7)$;

Y is $S(O)_{0-2}R^8$, $SO_2NRR^7$ or $CONRR^7$;

$Z^1$ is N;

$R^1$ and $R^2$ are independently H, halo, $C_{1-6}$ alkyl, $C_{2-6}$ alkenyl or $C_{2-6}$ alkynyl; or $R^1$ and $R^2$ together with the ring atoms to which they are attached form a fused 5-, 6- or 7-membered cycloalkyl, aryl, heteroaryl or heterocyclic ring;

each $R^3$ is the same or different and is independently H or $C_{1-6}$ alkyl;

$R^4$ and $R^5$ are independently $C_{1-6}$ alkyl, $C_{1-6}$ alkoxy, $C_{2-6}$ alkenyl or $C_{2-6}$ alkynyl, each of which may be optionally substituted with halo, amino or hydroxyl; halo, nitro, cyano, $C(R)(OR^7)(R^7)$, $OR^7$, $NR(R^7)$, $C(R)(NRR^7)(R^7)$, $(CR_2)_q$—W, $C(O)O_{0-1}R^7$, $C(O)NR(R^7)$, $C(O)CRR^7$—$NR(R^7)$, $C(O)NR(CR_2)_pNR(R^7)$, $C(O)NR(CR_2)_pOR^7$, $C(O)NR(CR_2)_pSR^7$, $C(O)NR(CR_2)_qS(O)_{1-2}R^8$, $S(O)_{0-2}R^8$, $(CR_2)_{1-6}NR(CR_2)_pOR^7$, $(CR_2)_{1-6}NR(CR_2)_qC(O)R^8$, $S(O)_2NRR^7$, $S(O)_2NR(CR_2)_pNR(R^7)$, or $S(O)_2NR(CR_2)_pOR^7$;

$R^6$ is H, $C_{1-6}$ alkyl, $C_{2-6}$ alkenyl or $C_{2-6}$ alkynyl, each of which may be optionally substituted with halo, amino, hydroxyl or alkoxy; —$(CR_2)_{1-4}$—CN, $(CR_2)_p$—$OR^7$, $(CR_2)_p$—$NR(R^7)$, -L-W, -L-C(O)—$R^7$, —$(CR_2)_{1-4}$—

C(O)—(CR$_2$)$_q$—OR$^7$, —C(O)OR$^8$, -L-C(O)—NRR$^7$, -L-CR(OR$^7$)—C$_t$F$^{(2t+1)}$ wherein t is 1-3; -L-C(O)—CR(R$^7$)—NRR$^7$, -L-C(O)—NR—(CR$_2$)$_p$—NRR$^7$, -L-C(O)NR(CR$_2$)$_p$OR$^7$, -L-C(O)—(CR$_2$)$_q$—NR—C(O)—R$^8$, -L-C(O)NR(CR$_2$)$_p$SR$^7$, -L-C(O)NR(CR$_2$)$_q$S(O)$_{1-2}$R$^8$, (CR$_2$)$_p$NR(CR$_2$)$_p$OR$^7$, (CR$_2$)$_p$NR-L-C(O)R$^8$, -L-S(O)$_2$R$^8$, -L-S(O)$_2$NRR$^7$, -L-S(O)$_2$NR(CR$_2$)$_p$NR(R$^7$), -L-S(O)$_2$NR(CR$_2$)$_p$OR$^7$ or a radical selected from formula (a), (b) or (c):

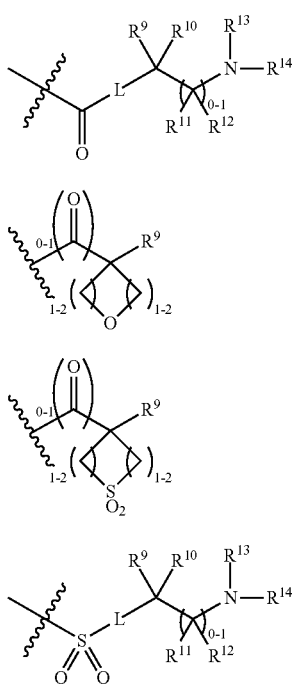

wherein R$^9$, R$^{10}$, R$^{11}$, R$^{12}$, R$^{13}$ and R$^{14}$ are independently selected from H, or C$_{1-6}$ alkyl, C$_{1-6}$ alkoxy, C$_{2-6}$ alkenyl or C$_{2-6}$ alkynyl, each of which may be optionally substituted with halo, amino, hydroxyl or alkoxy; or R$^9$ and R$^{10}$, R$^{10}$ and R$^{13}$, R$^{13}$ and R$^{14}$, R$^{11}$ and R$^{12}$, or R$^{11}$ and R$^{13}$ together with the carbon and/or nitrogen atoms to which they are attached may form a 3-7 membered saturated, unsaturated or partially unsaturated ring optionally containing up to 3 atoms or groups selected from C(O), N, O and S(O)$_{0-2}$ and optionally substituted with 1-3 R$^5$ groups;

L is (CR$_2$)$_{1-4}$ or a bond;

R$^7$ and R$^8$ are independently (CR$_2$)$_q$—W, or C$_{1-6}$ alkyl, C$_{2-6}$ alkenyl or C$_{2-6}$ alkynyl, each of which may be optionally substituted with halo, amino, hydroxyl, or alkoxy; or R$^7$ is H;

W is a C$_{3-12}$ carbocyclic ring, C$_{6-10}$ aryl, or a 5-10 membered heteroaryl or 4-10 membered heterocyclic ring, each of which is optionally substituted with 1-3 R$^{5'}$ groups wherein R$^{5'}$ is selected from R$^5$;

each R is H or C$_{1-6}$ alkyl;

m and n are independently 0-2;

p is 2-4; and q is 0-4.

2. The compound of claim 1, wherein X is a 5-6 membered heteroaryl; or X is a C$_{1-6}$ alkyl, C$_{2-6}$ alkenyl or C$_{2-6}$ alkynyl, each of which may be optionally substituted with halo, amino or hydroxyl; (CR$_2$)$_{1-4}$CO$_2$R$^7$ or (CR$_2$)$_{1-4}$CR(NRR$^7$)(CO$_2$R$^7$);

n is 0-1; and

R$^{5'}$ if present on X, is hydroxyl, C$_{1-6}$ alkyl, C$_{1-6}$ alkoxy, halo-substituted C$_{1-6}$ alkyl or halo-substituted C$_{1-6}$ alkoxy.

3. The compound of claim 1, wherein X is a 6 membered heterocyclic ring containing NR$^6$, O or S.

4. The compound of claim 1, wherein said compound is of Formula (3A) or (3B):

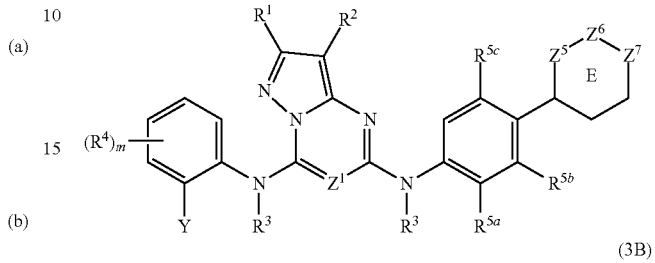

(3A)

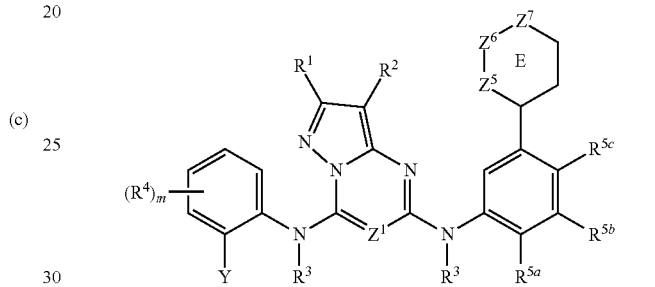

(3B)

wherein R$^{5a}$, R$^{5b}$ and R$^{5c}$ are independently H, halo, hydroxyl, C$_{1-6}$ alkyl, C$_{1-6}$ alkoxy, halo-substituted C$_{1-6}$ alkyl or halo-substituted C$_{1-6}$ alkoxy;

one of Z$^5$, Z$^6$ and Z$^7$ is NR$^6$, O or S, and the others are CH$_2$; and

R$^1$, R$^2$, R$^3$, R$^4$, R$^5$, R$^6$ and m are as defined in claim 1.

5. The compound of claim 4, wherein Z$^7$ is NR$^6$ or O; and Z$^5$ and Z$^6$ are CH$_2$.

6. The compound of claim 5, wherein R$^6$ is H, C$_{1-6}$ alkyl, C$_{2-6}$ alkenyl or C$_{2-6}$ alkynyl, each of which may be optionally substituted with halo, amino or hydroxyl groups; halo, nitro or cyano; L-W, -L-C(O)—R$^7$, —(CR$_2$)$_{1-4}$—C(O)—(CR$_2$)$_q$—OR$^7$, —C(O)OR$^8$, -L-C(O)—NRR$^7$, -L-C(O)—CR(R$^7$)—NRR$^7$, -L-S(O)$_2$R$^8$, or a radical of formula (a) or (b):

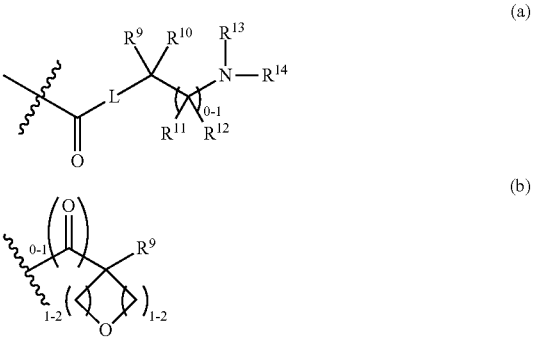

wherein R, R$^7$, R$^8$, R$^9$, R$^{10}$, R$^{11}$, R$^{12}$, R$^{13}$, R$^{14}$ and L are as defined in claim 1.

7. The compound of claim 4, wherein R$^{5b}$ is H; and R$^{5a}$ and R$^{5c}$ are independently halo, hydroxyl, C$_{1-6}$ alkyl, C$_{1-6}$ alkoxy, halo-substituted C$_{1-6}$ alkyl or halo-substituted C$_{1-6}$ alkoxy.

8. The compound of claim 1, wherein said compound is of Formula (3C) or (3D):

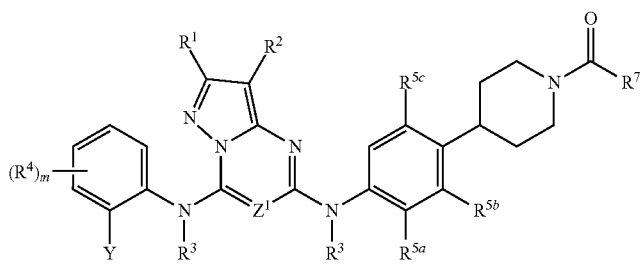

(3C)

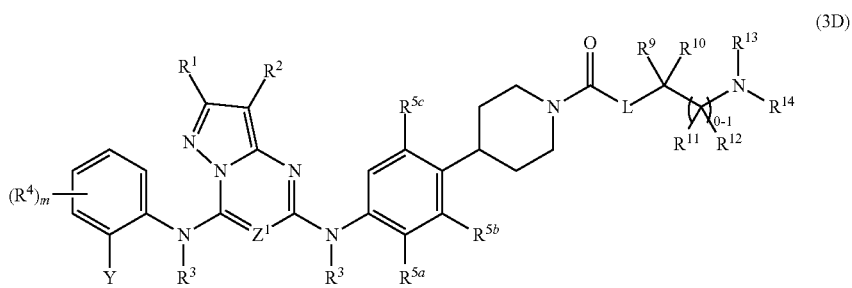

(3D)

wherein $R^{5a}$, $R^{5b}$ and $R^{5c}$ independently H, halo, hydroxyl, $C_{1-6}$ alkyl, $C_{1-6}$ alkoxy, halo-substituted $C_{1-6}$ alkyl or halo-substituted $C_{1-6}$ alkoxy;

$R^7$ is $(CR_2)_q$—W, or $C_{1-6}$ alkyl, $C_{2-6}$ alkenyl or $C_{2-6}$ alkynyl, each of which may be optionally substituted with halo, amino, hydroxyl, or alkoxy;

W is a 5-6 membered heterocyclic ring; and

R, $R^1$, $R^2$, $R^3$, $R^4$, $R^9$, $R^{10}$, $R^{11}$, $R^{12}$, $R^{13}$, $R^{14}$, L, q and m are as defined in claim 1.

9. The compound of claim 1, wherein $R^1$, $R^2$ and $R^3$ are H.

10. The compound of claim 1, wherein Y is $SO_2R^8$ and $R^7$ and $R^8$ are $C_{1-6}$ alkyl.

11. The compound of claim 1, wherein m is 0.

12. The compound of claim 1, wherein said compound is selected from the group consisting of:

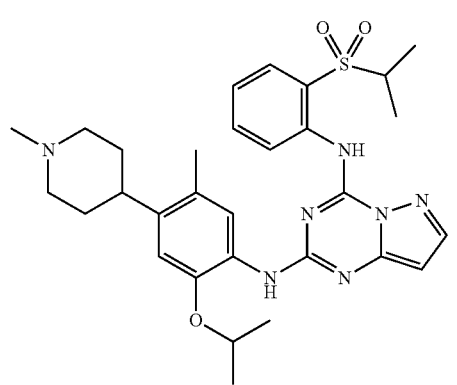

1

N2-(2-isopropoxy-5-methyl-4-(1-methylpiperidin-4-yl)phenyl)-N4-(2-(isopropylsulfonyl)phenyl)pyrazolo[1,5-a][1,3,5]triazine-2,4-diamine

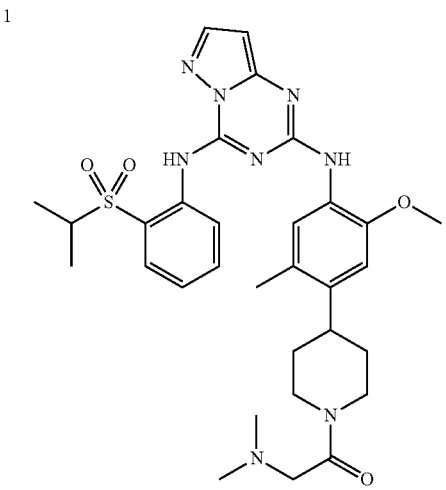

2

2-(dimethylamino)-1-(4-(4-(4-(2-(isopropylsulfonyl)phenylamino)pyrazolo-[1,5-a][1,3,5]triazin-2-ylamino)-5-methoxy-2-methylphenyl)piperidin-1-yl)ethanone

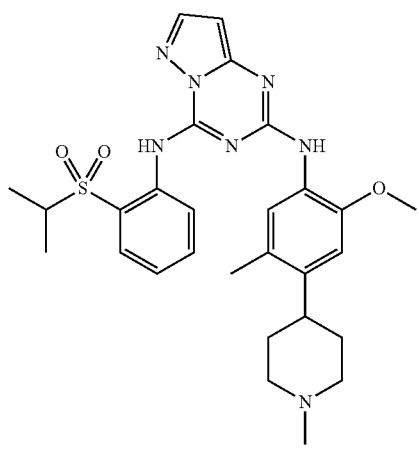

N4-(2-(isopropylsulfonyl)phenyl)-N2-(2-methoxy-5-methyl-4-(1-methylpiperidin-4-yl)-phenyl)pyrazolo[1,5-a][1,3,5]triazine-2,4-diamine

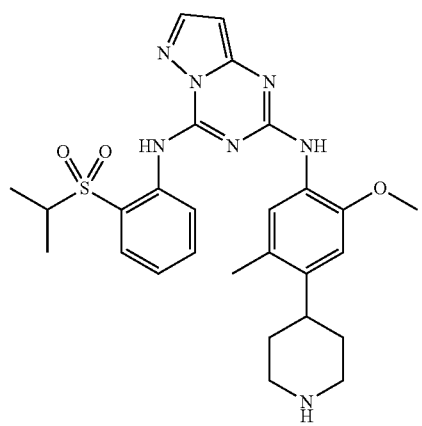

N4-(2-(isopropylsulfonyl)phenyl)-N2-(2-methoxy-5-methyl-4-(piperidin-4-yl)-phenyl)pyrazolo[1,5-a][1,3,5]triazine-2,4-diamine

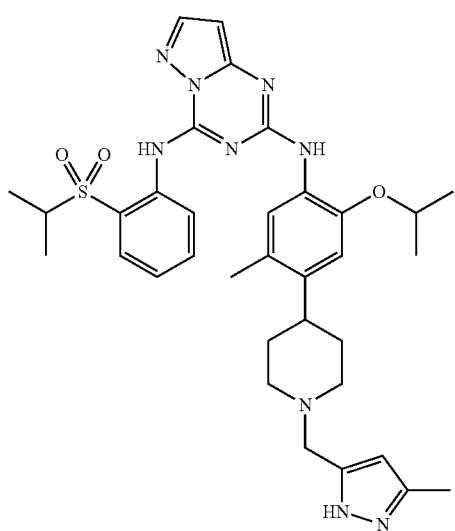

N2-(2-isopropoxy-5-methyl-4-(1-((3-methyl-1H-pyrazol-5-yl)methyl)piperidin-4-yl)phenyl)-N4-(2-(isopropylsulfonyl)-phenyl)pyrazolo[1,5-a][1,3,5]triazine-2,4-diamine

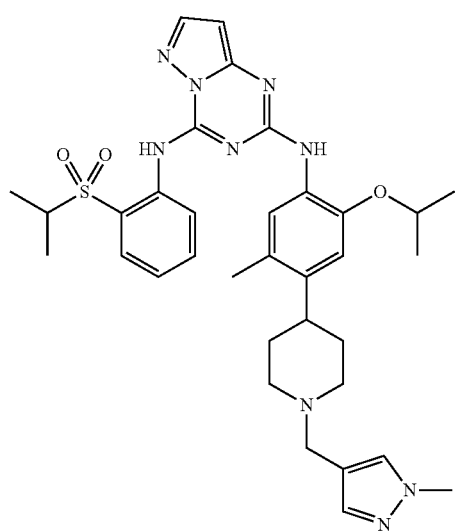

N2-(2-isopropoxy-5-methyl-4-(1-((1-methyl-1H-pyrazol-4-yl)methyl)piperidin-4-yl)phenyl)-N4-(2-(isopropylsulfonyl)-phenyl)pyrazolo[1,5-a][1,3,5]triazine-2,4-diamine

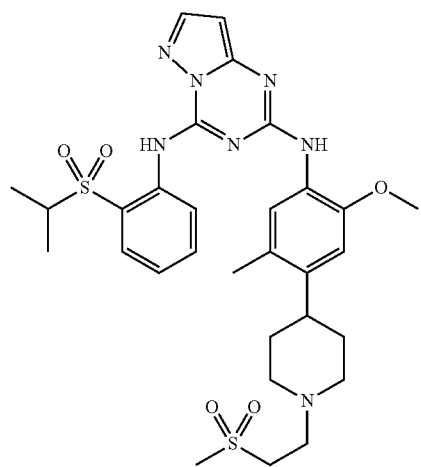

N4-(2-(isopropylsulfonyl)phenyl)-N2-(2-methoxy-5-methyl-4-(1-(2-(methylsulfonyl)ethyl)piperidin-4-yl)phenyl)-pyrazolo[1,5-a][1,3,5]triazine-2,4-diamine

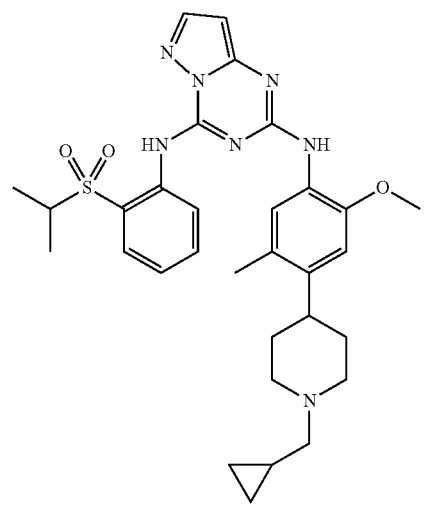

N2-(4-(1-(cyclopropylmethyl)piperidin-4-yl)-2-methoxy-5-methylphenyl)-N4-(2-(isopropylsulfonyl)phenyl)pyrazolo[1,5-a][1,3,5]triazine-2,4-diamine

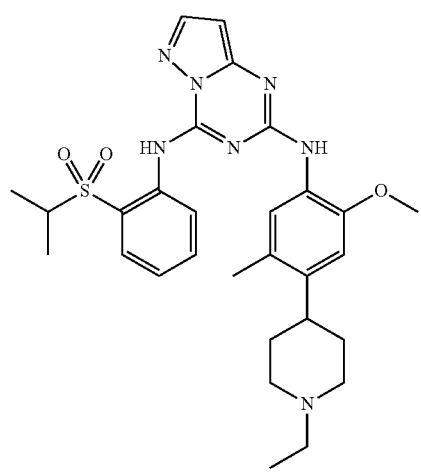

N2-(4-(1-ethylpiperidin-4-yl)-2-methoxy-5-methylphenyl)-N4-(2-(isopropylsulfonyl)-phenyl)pyrazolo[1,5-a][1,3,5]triazine-2,4-diamine

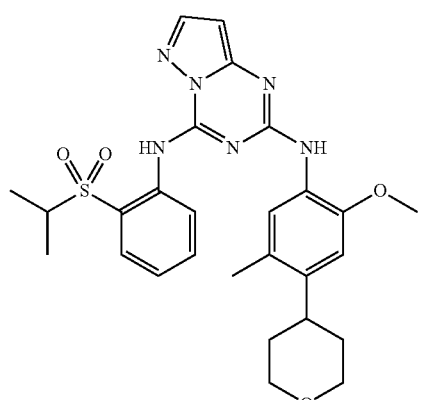

N4-(2-(isopropylsulfonyl)phenyl)-N2-(2-methoxy-5-methyl-4-(tetrahydro-2H-pyran-4-yl)phenyl)pyrazolo[1,5-a][1,3,5]-triazine-2,4-diamine

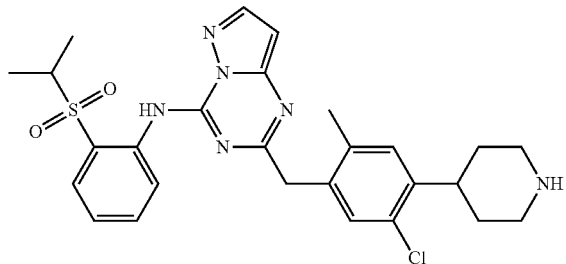

N2-(5-chloro-2-methyl-4-(piperidin-4-yl)-
phenyl)-N4-(2-(isopropylsulfonyl)phenyl)-
pyrazolo[1,5-a][1,3,5]triazine-2,4-diamine

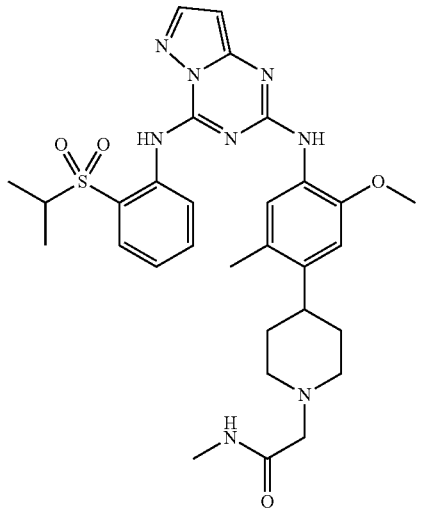

2-(4-(4-(4-(2-(isopropylsulfonyl)pheylamino)-
pyrazolo[1,5-a][1,3,5]triazin-2-ylamino)-5-
methoxy-2-methylphenyl)piperidin-1-yl)-N-
methylacetamide

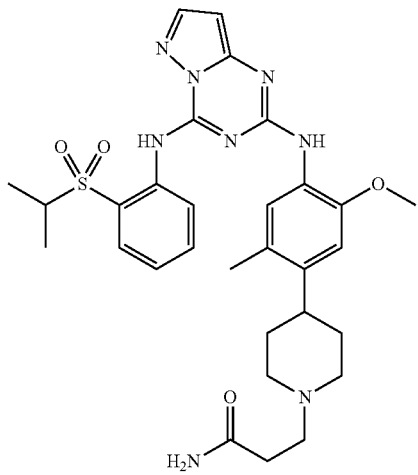

3-(4-(4-(4-(2-(isopropylsulfonyl)phenylamino)pyrazolo-
[1,5-a][1,3,5]triazin-2-ylamino)-5-methoxy-2-
methylphenyl)piperidin-1-yl)propanamide

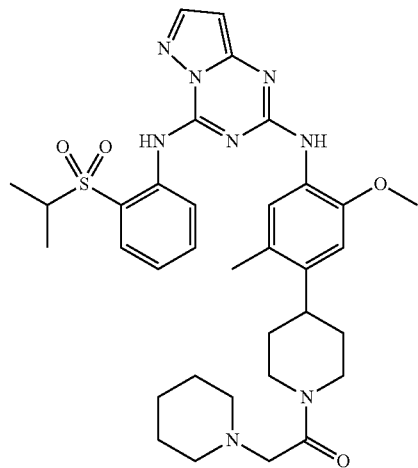

1-(4-(4-(4-(2-(isopropylsulfonyl)phenylamino)pyrazolo-
[1,5-a][1,3,5]triazin-2-ylamino)-5-methoxy-2-methylphenyl)-
piperidin-1-yl)-2-(piperidin-1-yl)ethanone

15

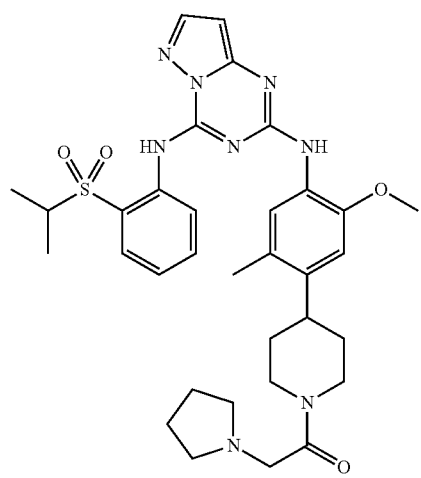

1-(4-(4-(4-(2-(isopropylsulfonyl)-
phenylamino)pyrazolo[1,5-a][1,3,5]-
triazin-2-ylamino)-5-methoxy-2-
methylphenyl)piperidin-1-yl)-2-
(pyrrolidin-1-yl)ethanone

16

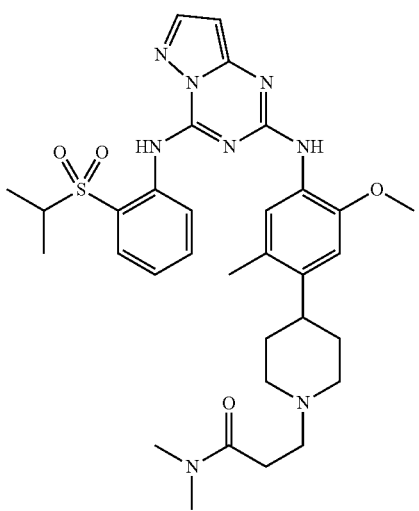

3-(4-(4-(4-(2-(isopropylsulfonyl)phenylamino)-
pyrazolo[1,5-a][1,3,5]triazin-2-ylamino)-5-methoxy-
2-methylphenyl)piperidin-1-yl)-N,N-dimethylpropanamide

17

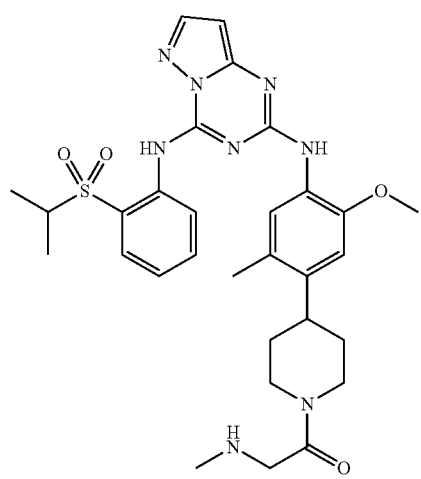

1-(4-(4-(4-(2-(isopropylsulfonyl)phenylamino)-
pyrazolo[1,5-a][1,3,5]triazin-2-ylamino)-5-
methoxy-2-methylphenyl)piperidin-1-yl)-
2-(methylamino)ethanone

18

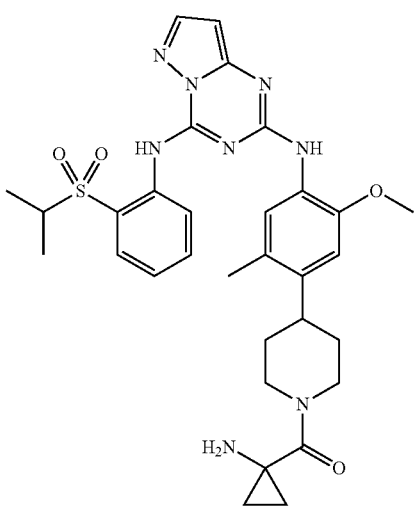

(1-aminocyclopropyl)(4-(4-(4-(2-
(isopopylsulfonyl)phenylamino)pyrazolo-
[1,5-a][1,3,5]triazin-2-ylamino)-5-methoxy-2-
methylphenyl)piperidin-1-yl-methanone

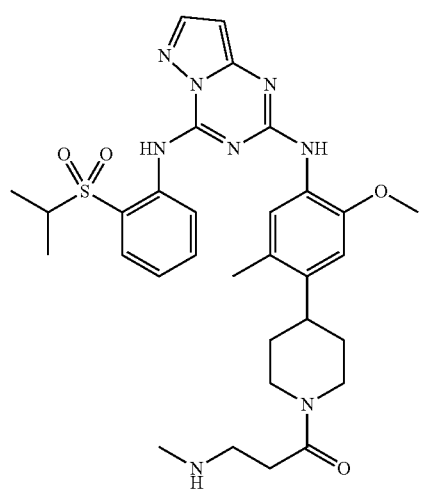

19

1-(4-(4-(4-(2-(isopropylsulfonyl)phenylamino)-pyrazolo[1,5-a][1,3,5]triazin-2-ylamino)-5-methoxy-2-methylphenyl)piperidin-1-yl)-3-(methylamino)-propan-1-one

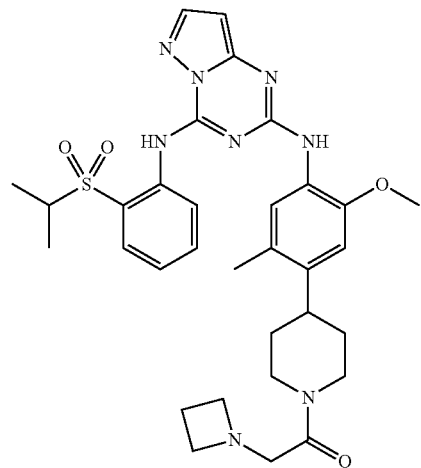

20

2-(azetidin-1-yl)-1-(4-(4-(4-(2-(isopropylsulfonyl)-phenylamino)pyrazolo[1,5-a][1,3,5]triazin-2-ylamino)-5-methoxy-2-methylphenyl)piperidin-1-yl)ethanone

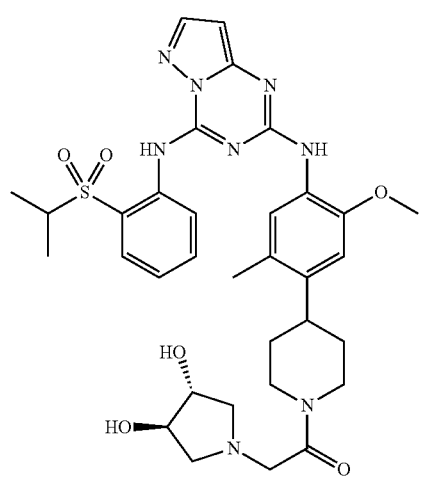

21

2-((3R,4R)-3,4-dihydroxypyrrolidin-1-yl)-1-(4-(4-(4-(2-(isopropylsulfonyl)phenylamino)-pyrazolo[1,5a][1,3,5]triazin-2-ylamino)-5-methoxy-2-methylphenyl)piperidin-1-yl)ethanone

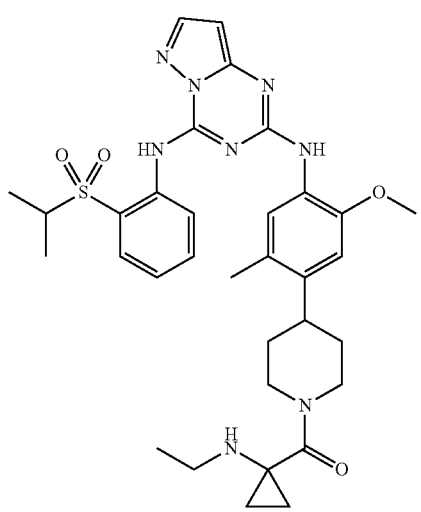

22

(1-(ethylamino)cyclopropyl)(4-(4-(4-(2-(isopropylsulfonyl)-phenylamino)pyrazolo[1,5-a][1,3,5]triazin-2-ylamino)-5-methoxy-2-methylphenyl)piperidin-1-yl)methanone

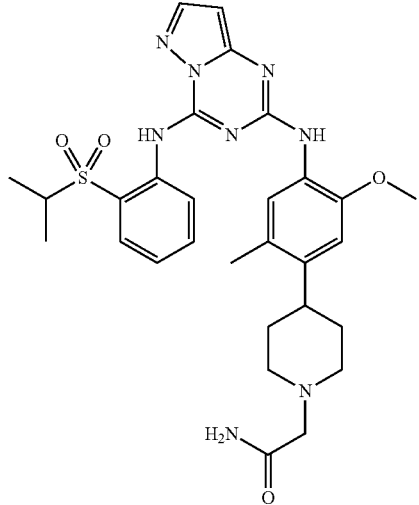

23

2-(4-(4-(4-(2-(isopropylsulfonyl)-
phenylamino)pyrazolo[1,5-a][1,3,5]-
triazin-2-ylamino)-5-methoxy-2-
methylphenyl)-piperidin-1-yl)acetamide

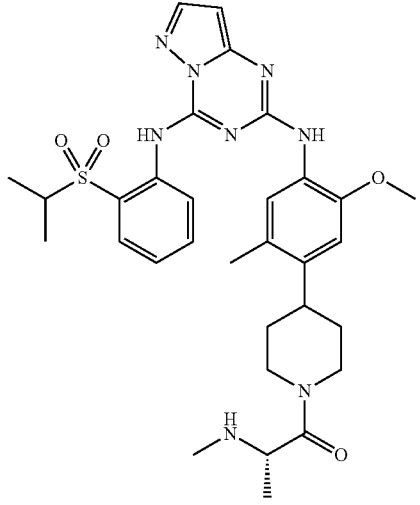

24

(S)-1-(4-(4-(4-(2-(isopropylsulfonyl)-
phenylamino)pyrazolo[1,5-a][1,3,5]-
triazin-2-ylamino)-5-methoxy-2-
methylphenyl)piperidin-1-yl)-2-
(methylamino)propan-1-one

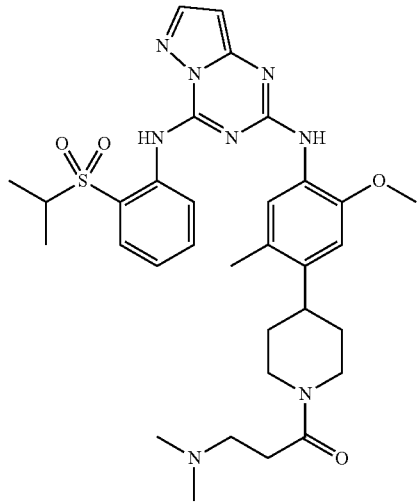

25

3-(dimethylamino)-1-(4-(4-(4-(2-
(isopropylsulfonyl)phenylamino)pyrazolo-
[1,5-a][1,3,5]triazin-2-ylamino)-5-methoxy-
2-methylphenyl)piperidin-1-yl)propan-1-one

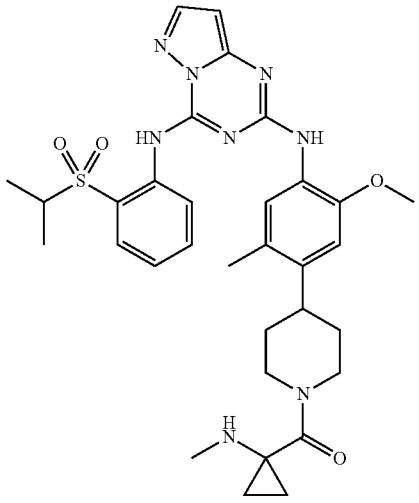

26

(4-(4-(4-(2-(isopropylsulfonyl)-
phenylamino)pyrazolo[1,5-a][1,3,5]-
triazin-2-ylamino)-5-methoxy-2-methylphenyl)-
piperidin-1-yl)(1-(methylamino)cyclopropyl)methanone

27

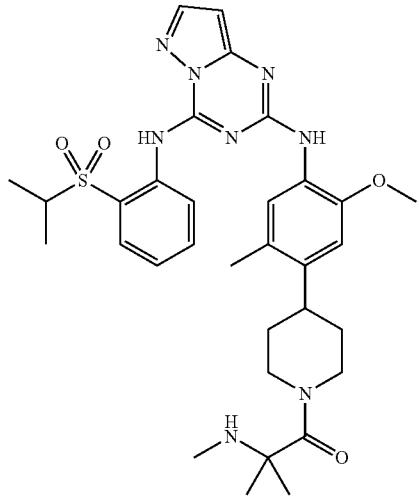

1-(4-(4-(4-(2-(isopropylsulfonyl)-
phenylamino)pyrazolo[1,5-a][1,3,5]triazin-
2-ylamino)-5-methoxy-2-methylphenyl)
piperidin-1-yl)-2-methyl-2-(methylamino)-
propan-1-one

28

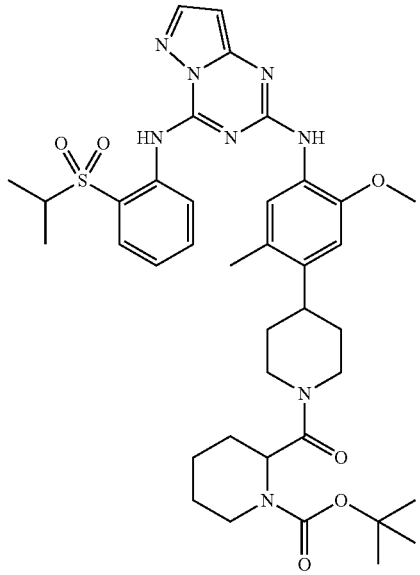

tert-butyl 2-(4-(4-(4-(2-(isopropylsulfonyl)-
phenylamino)pyrazolo[1,5-a][1,3,5]triazin-2-
ylamino)-5-methoxy-2-methylphenyl)
piperidine-1-carbonyl)piperidine-1-carboxylate

29

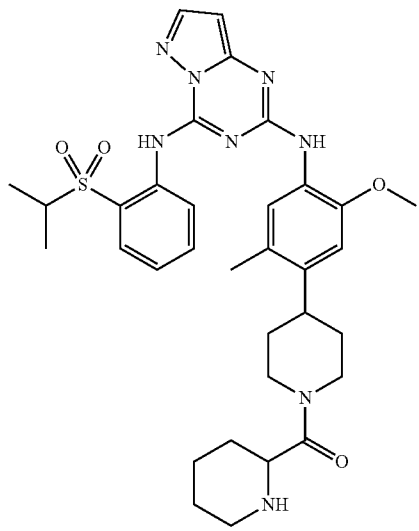

(4-(4-(4-(2-(isopropylsulfonyl)-
phenylamino)-pyrazolo[1,5-a][1,3,5]-
triazin-2-ylamino)-5-methoxy-2-
methylphenyl)piperidin-1-yl)piperidin-
2-yl)methanone

30

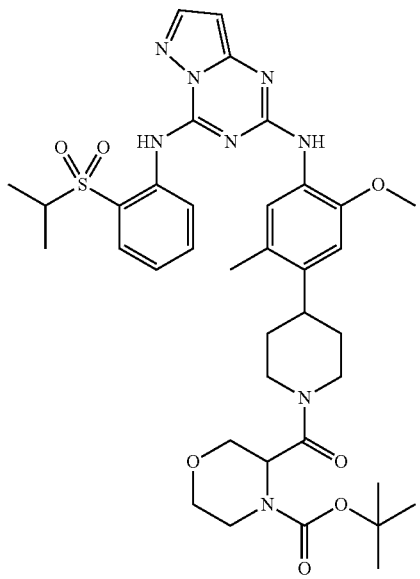

t-butyl 3-(4-(4-(4-(2-(isopropylsulfonyl)-
phenyl amino)pyrazolo[1,5-a][1,3,5]triazin-
2-ylamino)-5-methoxy-2-methylphenyl)
piperidine-1-carbonyl)morpholine-4-
carboxylate

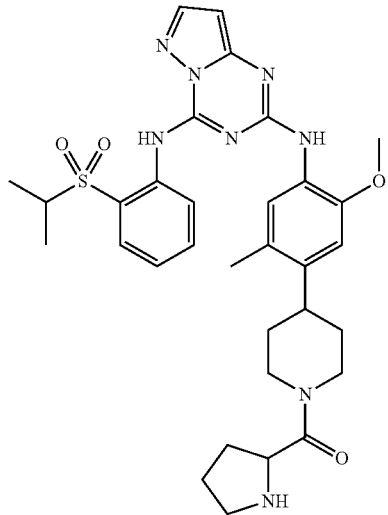

(4-(4-(4-(2-(isopropylsulfonyl)-
phenylamino)pyrazolo[1,5-a][1,3,5]-
triazin-2-ylamino)-5-methoxy-2-methyl-
phenyl)piperidin-1-yl)(pyrrolidin-2-yl)-
methanone

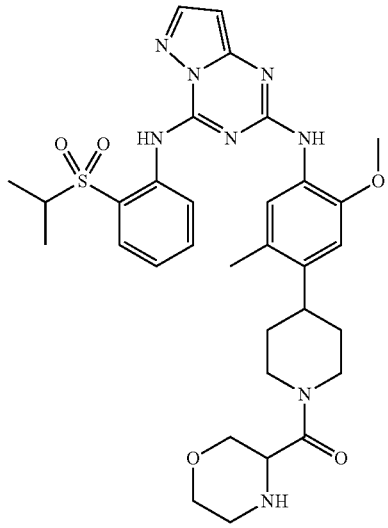

(4-(4-(4-(2-(isopropylsulfonyl)
phenylamino)pyrazolo[1,5-a]-
[1,3,5]triazin-2-ylamino)-5-methoxy-
2-methylphenyl)piperidin-1-yl)(morpholin-
3-yl)methanone

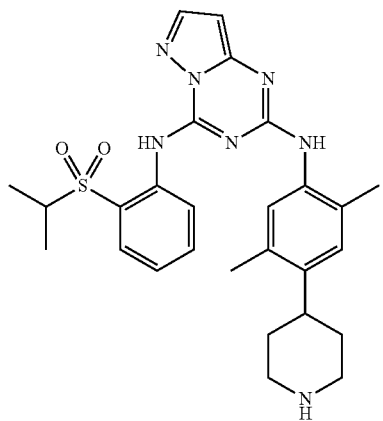

N2-(2,5-dimethyl-4-(piperidin-4-yl)-
phenyl)-N4-(2-(isopropylsulfonly)phenyl)-
pyrazolo[1,5-a][1,3,5]triazin-2,4-diamine

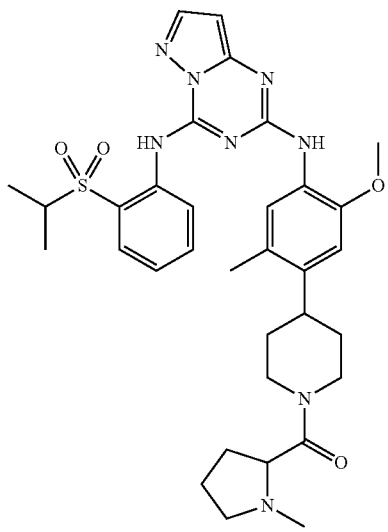

(4-(4-(4-(2-(isopropulsulfonyl)-
phenylamino)pyrazolo[1,5-a]1,3,5]-
triazin-2-ylamino)-5-methoxy-2-
methylphenyl)piperidin-1-yl)(1-
methylpyrrolidin-2-yl)methanone

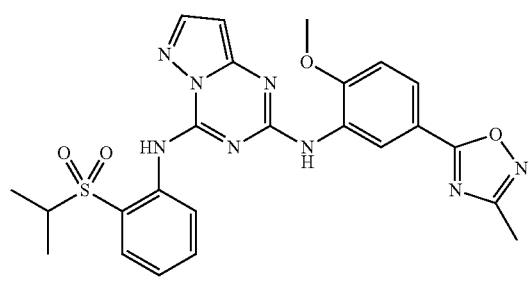

35

N4-(2-isopropylsulfonyl)phenyl)-N2-(2-
methoxy-5-(3-methyl-1,2,4-oxadiazol-5-
yl)phenyl)pyrazolo[1,5-a][1,3,5]triazin-
2,4-diamine

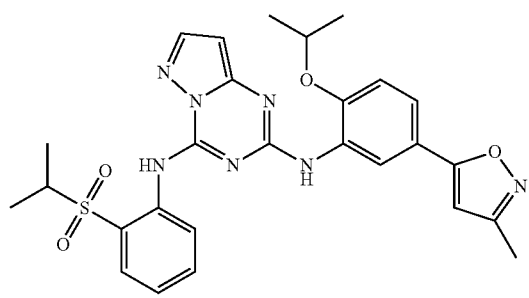

36

N2-(2-isopropoxy-5-(3-methylisoxazol-
5-yl)phenyl)-N4-(2-(isopropylsulfonyl)-
phenyl)pyrazolo[1,5-a][1,3,5]triazine-2,4-
diamine

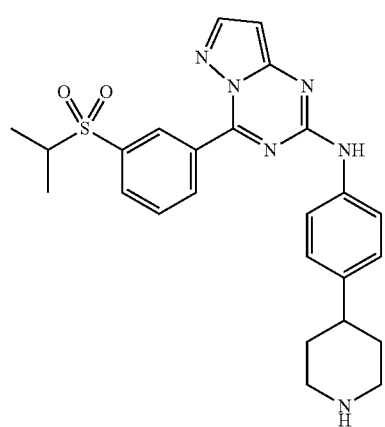

37

N4-(2-(isopropylsulfonyl)phenyl)-N2-
(4-(piperidin-4-yl)phenyl)pyrazolo[1,5-a]
[1,3,5]triazine-2,4-diamine

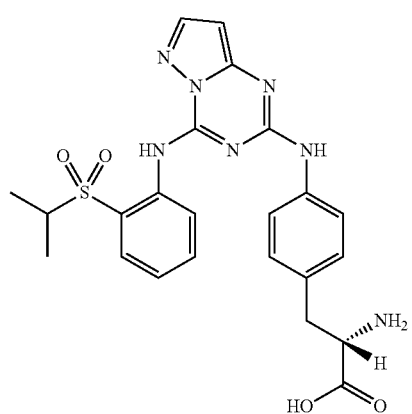

38

(S)-2-amino-3-(4-(4-(2-(isopropylsulfonyl)-
phenylamino)pyrazolo[1,5-a][1,3,5]triazin-2-
ylamino)phenyl)propanoic acid

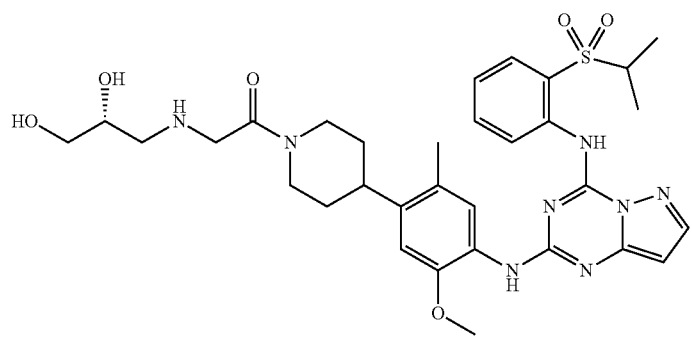

43

(R)-2-(2,3-dihydroxypropylamino)-1-(4-
(4-(2-(isopropylsulfonyl)phenylamino)
pyrazolo[1,5-a][1,3,5]triazin-2-ylamino)-
5-methoxy-2-methylphenyl)piperidin-1-
yl)ethanone

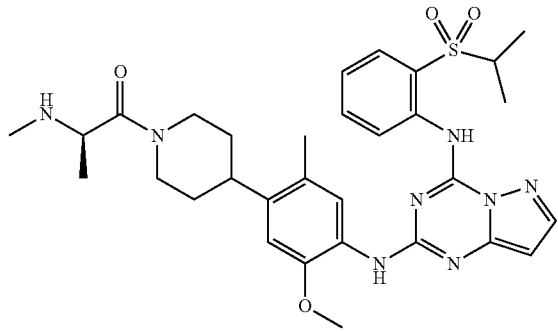

44

(R)-1-(4-(4-(4-(2-(isopropylsulfonyl)-
phenylamino)pyrazolo[1,5-a][1,3,5]-
triazin-2-ylamino)-5-methoxy-2-
methylphenyl)piperidin-1-yl)-2-
(methylamino)propan-1-one

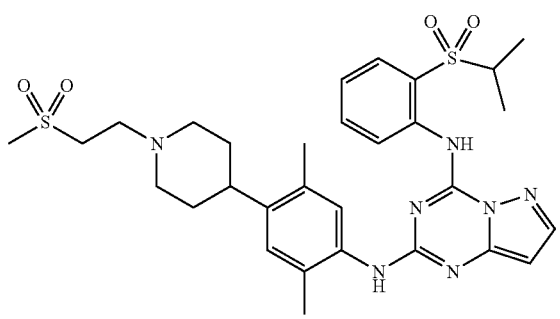

45

N2-(2,5-dimethyl-4-(1-(2-
(methylsulfonyl)ethyl)piperidin-
4-yl)phenyl)-N4-(2-(isopropysulfonyl)-
phenyl)pyrazolo[1,5-a][1,3,5]triazine-
2,4-diamine

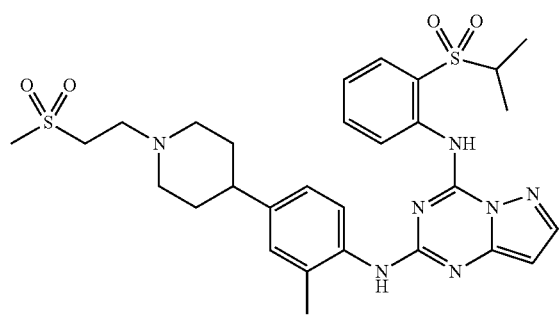

46

N4-(2-(isopropylsulfonyl)phenyl)-
N2-(2-methyl-4-(1-(2-(methylsulfonyl)-
ethyl)piperidin-4-yl)phenyl)pyrazolo[1,5-a]-
[1,3,5]triazine-2,4-diamine

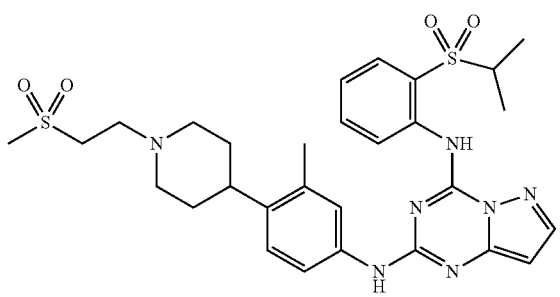

47

N4-(2-(isopropylsulfonyl)phenyl)-N2-
(3-methyl-4-(1-(2-(methylsulfonyl)-
ethyl)piperidin-4-yl)phenyl)pyrazolo[1,5-a]-
[1,3,5]triazine-2,4-diamine

48

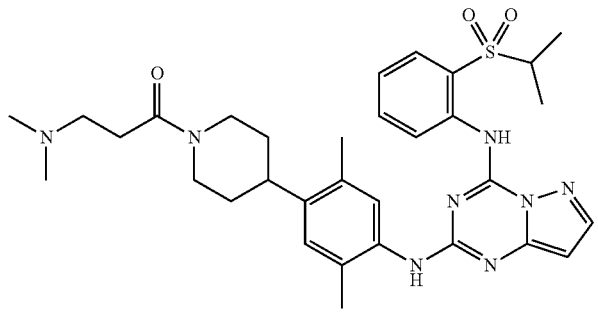

3-(dimethylamino)-1-(4-(4-(4-(2-(isopropylsulfonyl)phenylamino)-pyrazolo[1,5-a][1,3,5]triazin-2-ylamino)-2,5-dimethylphenyl)piperidin-1-yl)propan-1-one

49

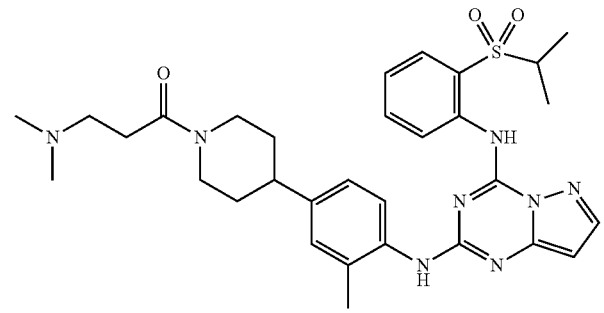

3-(dimethylamino)-1-(4-(4-(4-(2-(isopropylsulfonyl)phenylamino)-pyrazolo[1,5-a][1,3,5]triazin-2-ylamino)-3-methylphenyl)piperidin-1-yl)propan-1-one

50

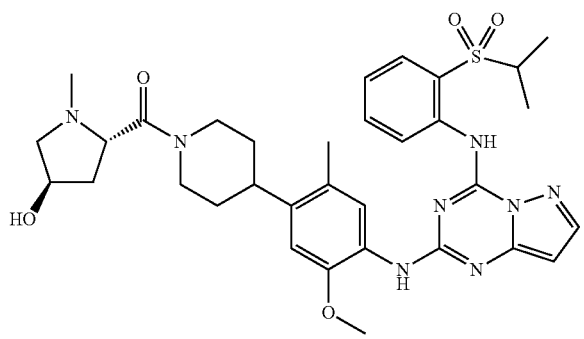

((2S,4R)-4-hydroxy-1-methylpyrrolidin-2-yl)(4-(4-(4-(2-(isopropylsulfonyl)-phenylamino)pyrazolo[1,5-a][1,3,5]triazin-2-ylamino)-5-methoxy-2-methylphenyl)piperidin-1-yl)methanone

51

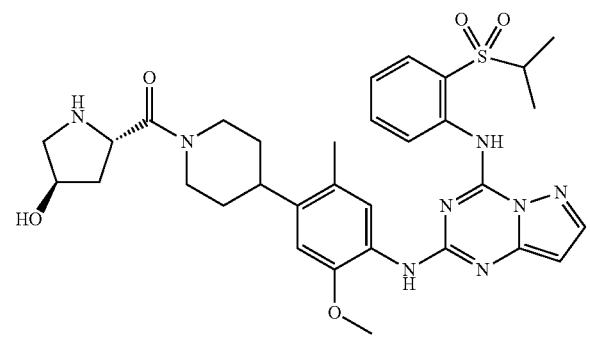

((2S,4R)-4-hydroxypyrrolidin-2-yl)(4-(4-(4-(2-(isopropylsulfonyl)-phenylamino)pyrazolo[1,5-a][1,3,5]triazin-2-ylamino)-5-methoxy-2-methylphenyl)piperidin-1-yl)methanone

52

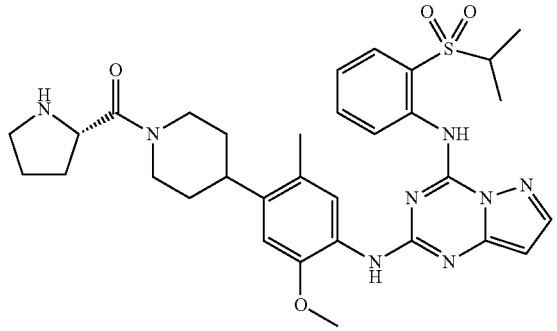

(S)-(4-(4-(4-(2-(isopropylsulfonyl)-phenylamino)pyrazolo[1,5-a][1,3,5]triazin-2-ylamino)-5-methoxy-2-methylphenyl)piperidin-1-yl)(pyrrolidin-2-yl)methanone

53

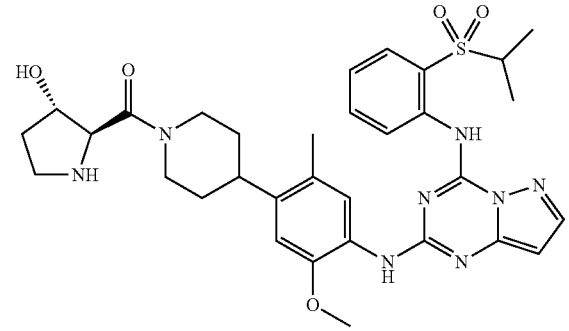

((2S,3S)-3-hydroxypyrrolidin-2-yl)(4-(4-(4-(2-(isopropylsulfonyl)-phenylamino)pyrazolo[1,5-a][1,3,5]triazin-2-ylamino)-5-methoxy-2-methylphenyl)piperidin-1-yl)methanone

54

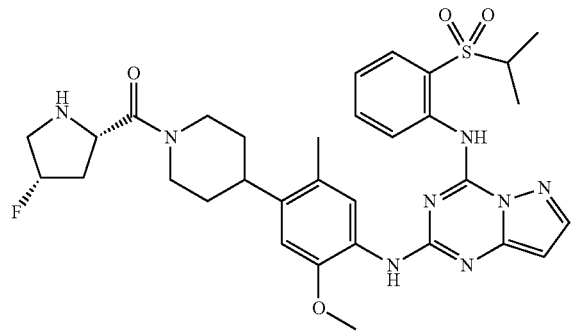

((2S,4S))-4-fluoropyrrolidin-2-yl)(4-(4-(4-(2-
(isopropylsulfonyl)phenylamino)pyrazolo[1,5-a]-
[1,3,5]triazin-2-ylamino)-5-methoxy-2-
methylphenyl)piperidin-1-yl)methanone

55

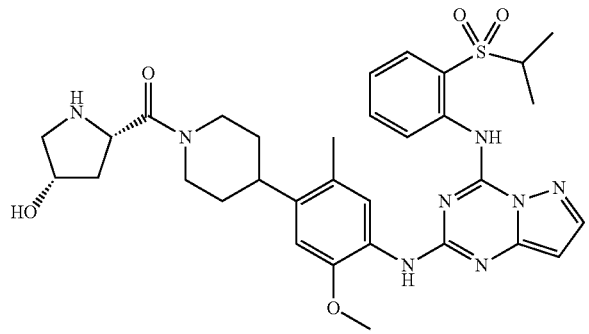

((2S,4S))-4-hydroxypyrrolidin-2-yl)(4-(4-(4-(2-
(isopropylsulfonyl)phenylamino)pyrazolo[1,5-a]-
[1,3,5]triazin-2-ylamino)-5-methoxy-2-
methylphenyl)piperidin-1-yl)methanone

56

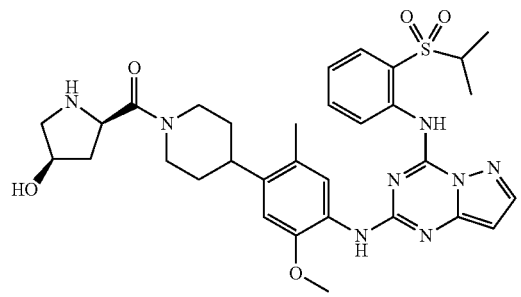

((2R,4R))-4-hydroxypyrrolidin-2-yl)(4-(4-(4-(2-
(isopropylsulfonyl)phenylamino)pyrazolo[1,5-a]-
[1,3,5]triazin-2-ylamino)-5-methoxy-2-
methylphenyl)piperidin-1-yl)methanone

57

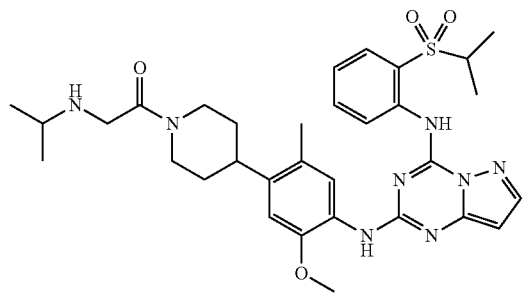

((2R,4R))-4-hydroxypyrrolidin-2-yl)(4-(4-(4-(2-
(isopropylsulfonyl)phenylamino)pyrazolo[1,5-a]-
[1,3,5]triazin-2-ylamino)-5-methoxy-2-
methylphenyl)piperidin-1-yl)methanone

58

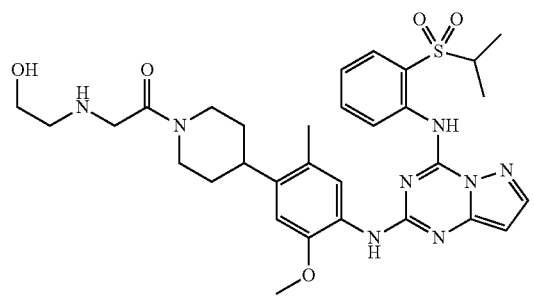

2-(2-hydroxyethylamino)-1-(4-(4-(4-(2-
(isopropylsulfonyl)phenylamino)pyrazolo-
[1,5-a][1,3,5]triazin-2-ylamino)-5-methoxy-
2-methylphenyl)piperidin-1-yl)ethanone

59

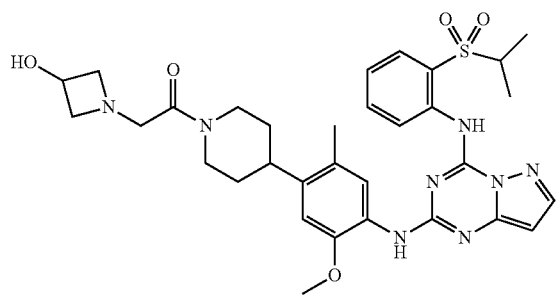

2-(3-hydroxyazetidin-1-yl)-1-(4-(4-(4-(2-
(isopropylsulfonyl)phenylamino)pyrazolo-
[1,5-a][1,3,5]triazin-2-ylamino)-5-methoxy-
2-methylphenyl)piperidin-1-yl)ethanone

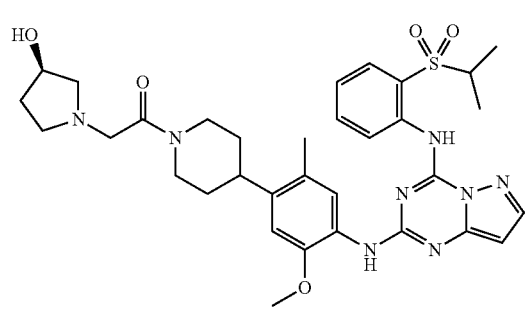

(R)-2-(3-hydroxypyrrolidin-1-yl)-1-(4-(4-(4-(2-(isopropylsulfonyl)phenylamino)pyrazolo-[1,5-a][1,3,5]triazin-2-ylamino)-5-methoxy-2-methylphenyl)piperidin-1-yl)ethanone

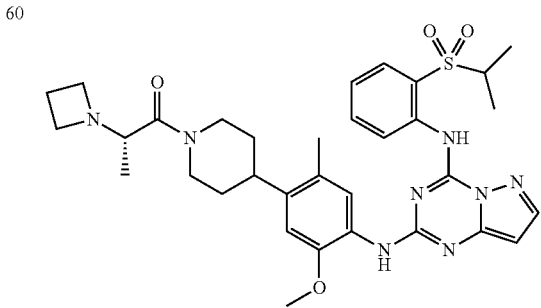

(S)-2-(azetidin-1-yl)-1-(4-(4-(4-(2-(isopropylsulfonyl)phenylamino)pyrazolo-[1,5-a][1,3,5]triazin-2-ylamino)-5-methoxy-2-methylphenyl)piperidin-1-yl)propan-1-one

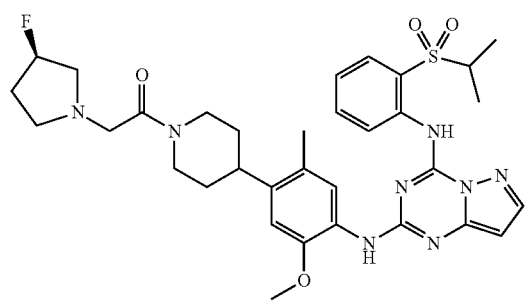

(R)-2-(3-fluoropyrrolidin-1-yl)-1-(4-(4-(4-(2-(isopropylsulfonyl)phenylamino)pyrazolo-[1,5-a][1,3,5]triazin-2-ylamino)-5-methoxy-2-methylphenyl)piperidin-1-yl)propan-1-one

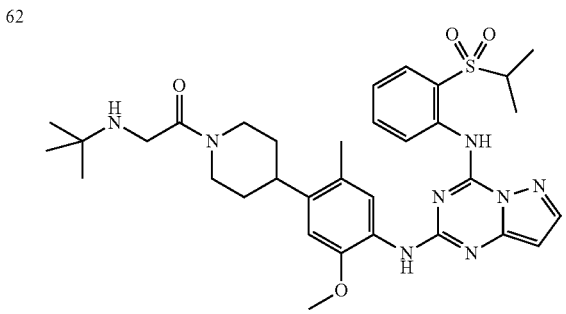

(R)-2-(3-fluoropyrrolidin-1-yl)-1-(4-(4-(4-(2-(isopropylsulfonyl)phenylamino)pyrazolo-[1,5-a][1,3,5]triazin-2-ylamino)-5-methoxy-2-methylphenyl)piperidin-1-yl)propan-1-one

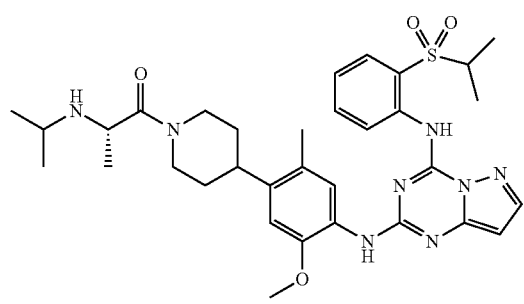

(S)-2-(isopropylamino)-1-(4-(4-(4-(2-(isopropylsulfonyl)phenylamino)pyrazolo-[1,5-a][1,3,5]triazin-2-ylamino)-5-methoxy-2-methylphenyl)piperidin-1-yl)propan-1-one

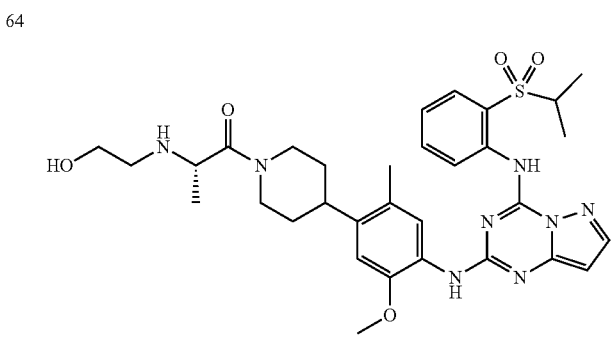

(S)-2-(isopropylamino)-1-(4-(4-(4-(2-(isopropylsulfonyl)phenylamino)pyrazolo-[1,5-a][1,3,5]triazin-2-ylamino)-5-methoxy-2-methylphenyl)piperidin-1-yl)propan-1-one

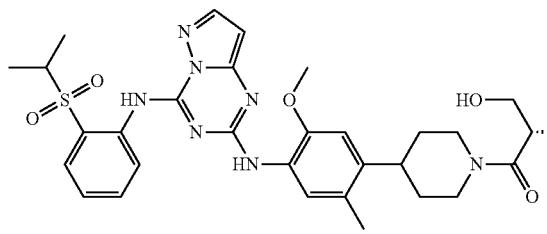

66

(S)-2-amino-3-hydroxy-1-(4-(4-(4-(2-(isopropylsulfonyl)phenylamino)pyrazolo-[1,5-a][1,3,5]triazin-2-ylamino)-5-methoxy-2-methylphenyl)piperidin-1-yl)propan-1-one

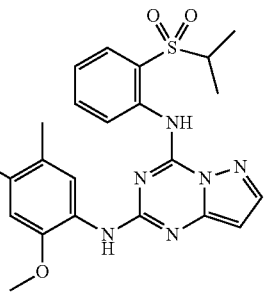

67

(R)-(4-(4-(4-(2-(isopropylsulfonyl)-phenylamino)pyrazolo[1,5-a][1,3,5]-triazin-2-ylamino)-5-methoxy-2-methylphenyl)piperidin-1-yl)(morpholin-3-yl)methanone

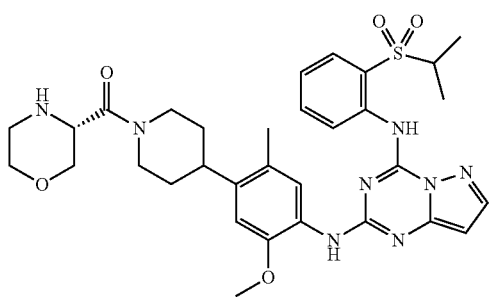

68

(S)-(4-(4-(4-(2-(isopropylsulfonyl)phenylamino)pyrazolo[1,5-a][1,3,5]-triazin-2-ylamino)-5-methoxy-2-methylphenyl)piperidin-1-yl)(morpholin-3-yl)methanone

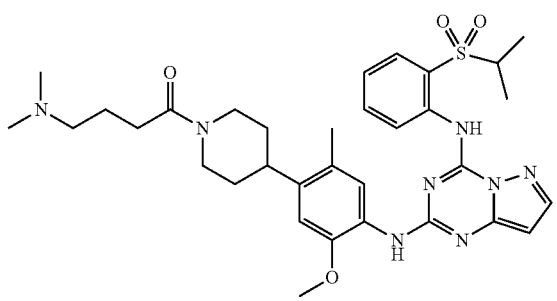

69

4-(dimethylamino)-1-(4-(4-(4-(2-(isopropylsulfonyl)phenylamino)pyrazolo[1,5-a][1,3,5]-triazin-2-ylamino)-5-methoxy-2-methylphenyl)piperidin-1-yl)butan-1-one

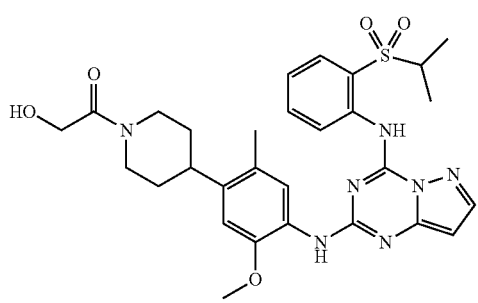

70

2-hydroxy-1-(4-(4-(4-(2-(isopropylsulfonyl)phenylamino)pyrazolo[1,5-a][1,3,5]-triazin-2-ylamino)-5-methoxy-2-methylphenyl)piperidin-1-yl)ethanone

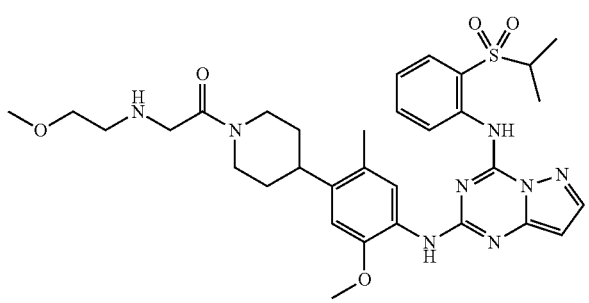

71

2-hydroxy-1-(4-(4-(4-(2-(isopropylsulfonyl)phenylamino)pyrazolo[1,5-a][1,3,5]-triazin-2-ylamino)-5-methoxy-2-methylphenyl)piperidin-1-yl)ethanone

72

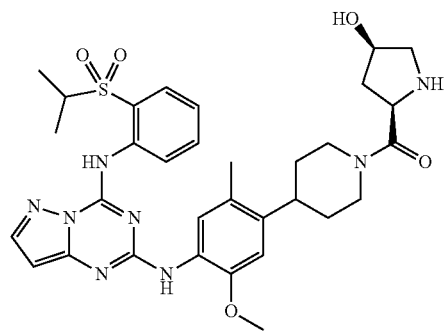

((2R,4R)-4-hydroxypyrrolidin-2-yl)(4-
(4-(4-(2-(isopropylsulfonyl)-
phenylamino)pyrazolo[1,5-a][1,3,5]-
triazin-2-ylamino)-5-methoxy-2-
methylphenyl)piperidin-1-yl)methanone

73

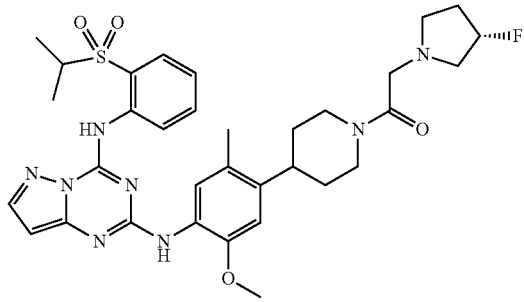

(S)-2-(3-fluoropyrrolidin-1-yl)-1-(4-
(4-(4-(2-(isopropylsulfonyl)-
phenylamino)pyrazolo[1,5-a][1,3,5]-
triazin-2-ylamino)-5-methoxy-2-
methylphenyl)piperidin-1-yl)ethanone

74

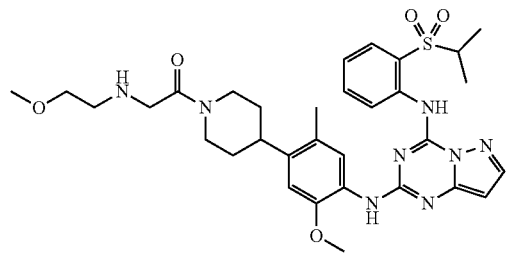

1-(4-(4-(4-(2-(isopropylsulfonyl)-
phenylamino)pyrazolo[1,5-a][1,3,5]-
triazin-2-ylamino)-5-methoxy-2-
methylphenyl)piperidin-1-yl)-2-(2-
methoxyethylamino)ethanone

75

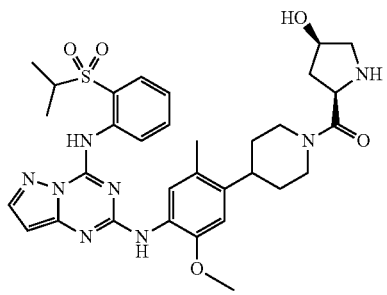

((2R,4R)-4-hydroxypyrrolidin-2-yl)-
(4-(4-(4-(2-(isopropylsulfonyl)-
phenylamino)pyrazolo[1,5-a][1,3,5]-
triazin-2-ylamino)-5-methoxy-2-
methylphenyl)piperidin-1-yl)-2-(2-
methoxyethylamino)ethanone

76

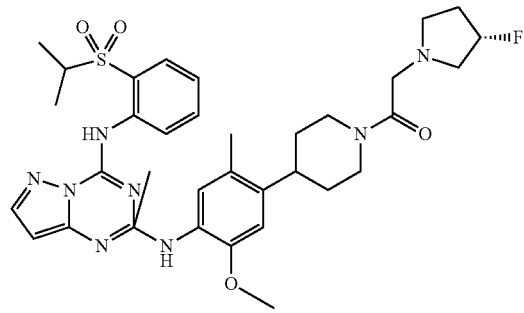

(S)-2-(3-fluoropyrrolidin-1-yl)-1-
(4-(4-(4-(2-(isopropylsulfonyl)-
phenylamino)pyrazolo[1,5-a][1,3,5]-
triazin-2-ylamino)-5-methoxy-2-
methylphenyl)piperidin-1-yl)ethanone

77

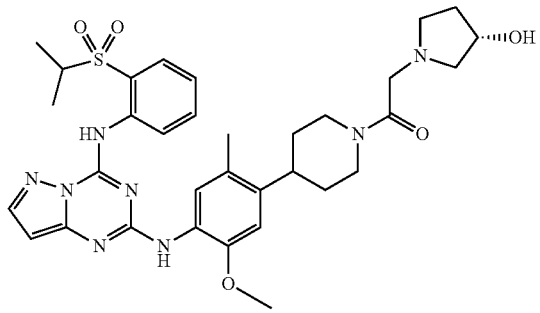

(S)-2-(3-hydroxypyrrolidin-1-yl)-1-
(4-(4-(4-(2-(isopropylsulfonyl)-
phenylamino)pyrazolo[1,5-a][1,3,5]-
triazin-2-ylamino)-5-methoxy-2-
methylphenyl)piperidin-1-yl)ethanone

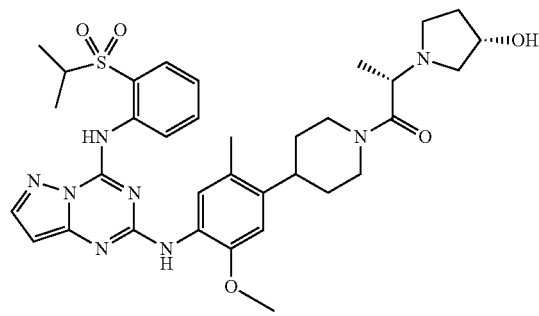

78

(S)-2-((S)-3-hydroxypyrrolidin-1-yl)-1-
(4-(4-(4-(2-(isopropylsulfonyl)-
phenylamino)pyrazolo[1,5-a][1,3,5]-
triazin-2-ylamino)-5-methoxy-2-
methylphenyl)piperidin-1-yl)propan-1-one

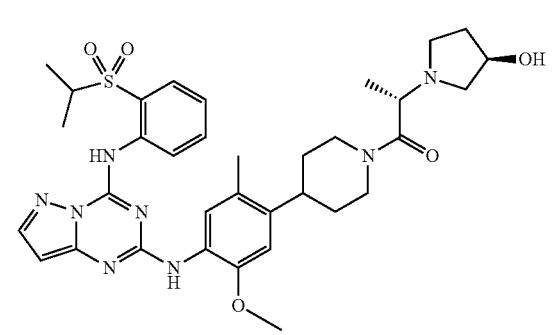

79

(S)-2-((R)-3-hydroxypyrrolidin-1-yl)-1-
(4-(4-(4-(2-(isopropylsulfonyl)-
phenylamino)pyrazolo[1,5-a][1,3,5]-
triazin-2-ylamino)-5-methoxy-2-
methylphenyl)piperidin-1-yl)propan-1-one

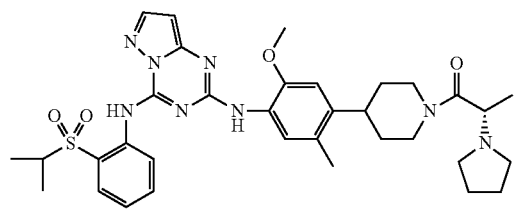

80

(S)-1-(4-(4-(4-(2-(isopropylsulfonyl)-
phenylamino)pyrazolo[1,5-a][1,3,5]-
triazin-2-ylamino)-5-methoxy-2-methylphenyl)-
piperidin-1-yl)-2-(pyrrolidin-1-yl)propan-1-one

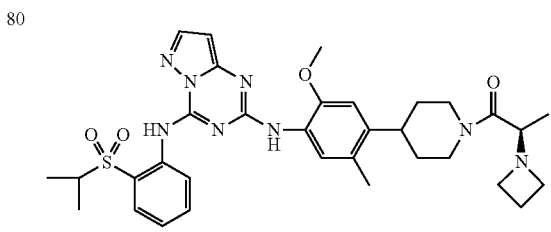

81

(R)-2-(azetidin-1-yl)(4-(4-(4-(2-
(isopropylsulfonyl)-phenylamino)-
pyrazolo[1,5-a][1,3,5]-triazin-2-ylamino)
-5-methoxy-2-methylphenyl)-
piperidin-1-yl)-2-(pyrrolidin-1-yl)propan-1-one

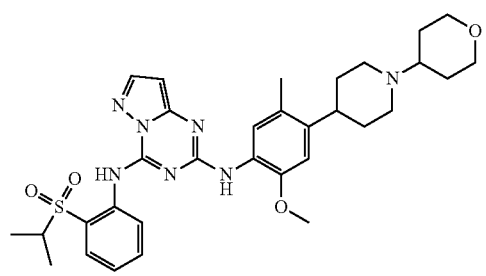

83

N4-(2-(isopropylsulfonyl)phenyl)-
N2-(2-methoxy-5-methyl-4-(1-
(tetrahydro-2H-pyran-4-yl)piperidin-
4-yl)phenyl)pyrazolo[1,5-a][1,3,5]triazine-
2,4-diamine

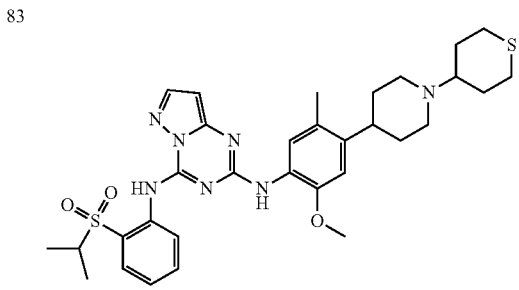

84

N4-(2-(isopropylsulfonyl)phenyl)-
N2-(2-methoxy-5-methyl-4-(1-
(tetrahydro-2H-thiopyran-4-yl)piperidin-
4-yl)phenyl)pyrazolo[1,5-a][1,3,5]triazine-
2,4-diamine

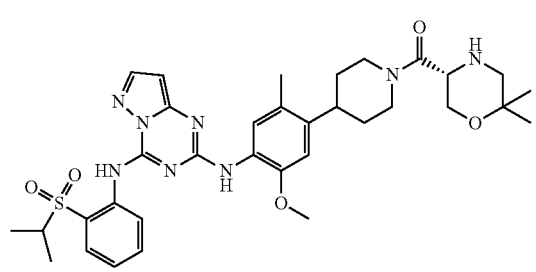

85

(R)-(6,6-dimethylmorpholin-3-yl)(4-(4-(4-(2-(isopropylsulfonyl)phenylamino)pyrazolo[1,5-a]-[1,3,5]triazin-2-ylamino)-5-methoxy-2-methylphenyl)piperidin-1-yl)methanone

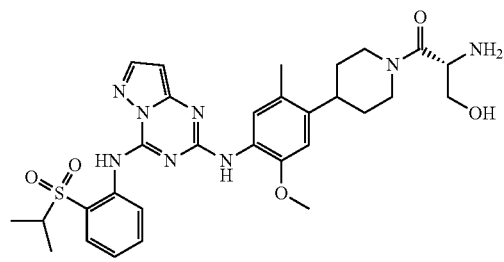

86

(R)-2-amino-3-hydroxy-1-(4-(4-(4-(2-(isopropylsulfonyl)phenylamino)pyrazolo[1,5-a]-[1,3,5]triazin-2-ylamino)-5-methoxy-2-methylphenyl)piperidin-1-yl)propan-1-one

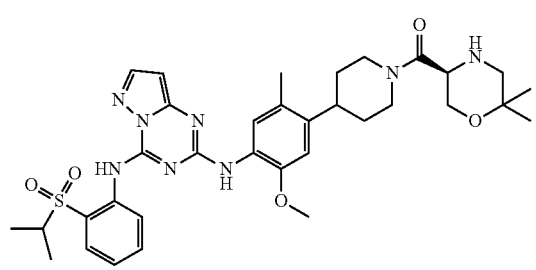

87

(S)-(6,6-dimethylmorpholin-3-yl)(4-(4-(4-(2-(isopropylsulfonyl)phenylamino)pyrazolo[1,5-a]-[1,3,5]triazin-2-ylamino)-5-methoxy-2-methylphenyl)piperidin-1-yl)methanone

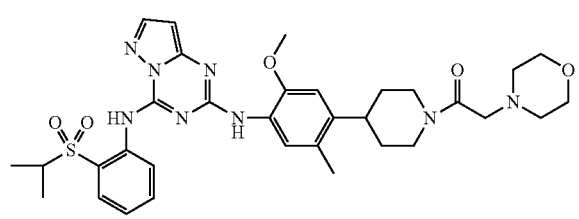

88

1-(4-(4-(4-(2-(isopropylsulfonyl)phenylamino)pyrazolo[1,5-a]-[1,3,5]triazin-2-ylamino)-5-methoxy-2-methylphenyl)piperidin-1-yl)-2-morpholinoethanone

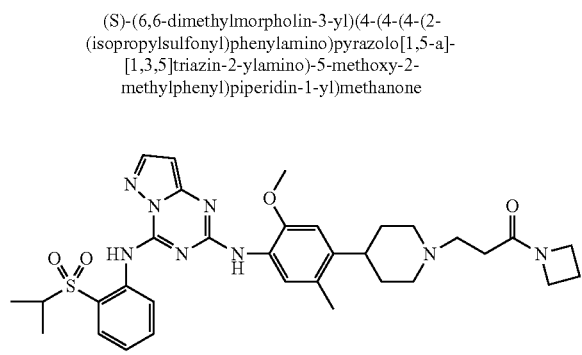

89

1-(aetidin-1-yl)-3-(4-(4-(4-(2-(isopropylsulfonyl)phenylamino)pyrazolo[1,5-a]-[1,3,5]triazin-2-ylamino)-5-methoxy-2-methylphenyl)piperidin-1-yl)propan-1-one

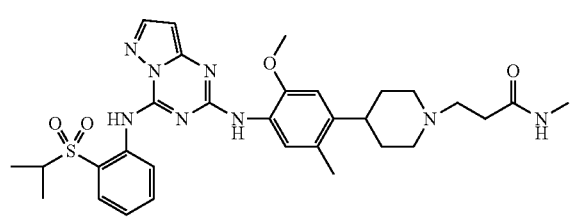

90

3-(4-(4-(4-(2-(isopropylsulfonyl)phenylamino)pyrazolo[1,5-a]-[1,3,5]triazin-2-ylamino)-5-methoxy-2-methylphenyl)piperidin-1-yl)-N-methylpropanamide

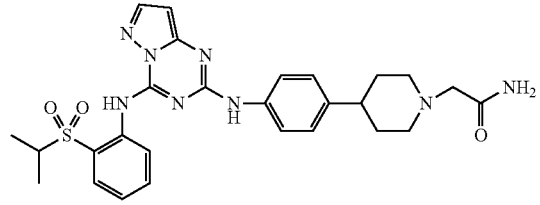

91

2-(4-(4-(4-(2-(isopropylsulfonyl)-phenylamino)pyrazolo[1,5-a][1,3,5]triazin-2-ylamino)phenyl)piperidin-1-yl)acetamide

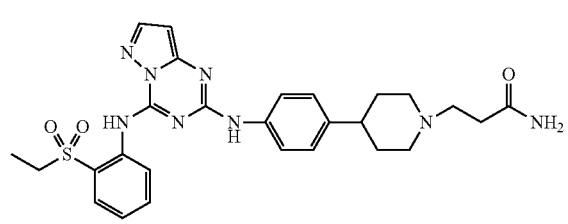

92

3-(4-(4-(4-(2-(isopropylsulfonyl)-phenylamino)pyrazolo[1,5-a][1,3,5]triazin-2-ylamino)phenyl)piperidin-1-yl)propanamide

93

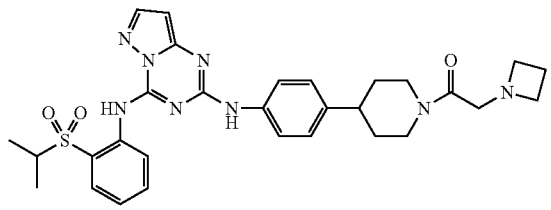

2-(azetidin-1-yl)-1-(4-(4-(4-(2-(isopropylsulfonyl)-
phenylamino)pyrazolo[1,5-a][1,3,5]triazin-2-ylamino)-
phenyl)piperidin-1-yl)ethanone

94

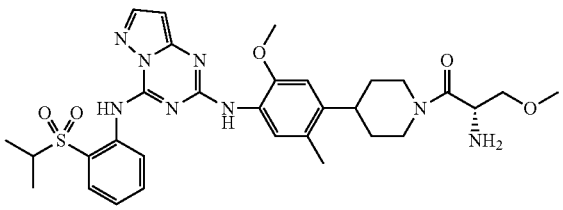

(S)-2-amino-1-(4-(4-(4-(2-(isopropylsulfonyl)-
phenylamino)pyrazolo[1,5-a][1,3,5]triazin-
2-ylamino)-5-methoxy-2-methylphenyl)piperidin-
1-yl)-3-methoxypropan-1-one

95

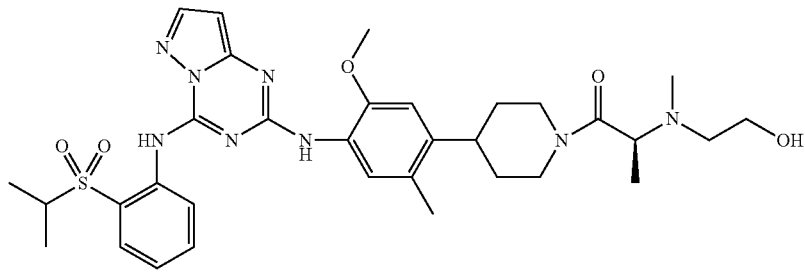

(S)-2-((2-hydroxyethyl)(methyl)amino)-1-
(4-(4-(4-(2-(isopropylsulfonyl)-
phenylamino)pyrazolo[1,5-a][1,3,5]triazin-
2-ylamino)-5-methoxy-2-methylphenyl)piperidin-
1-yl)-3-methoxypropan-1-one

96

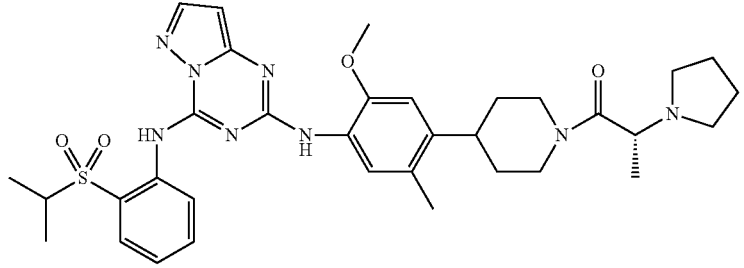

(R)-1-(4-(4-(4-(2-(isopropylsulfonyl)-
phenylamino)pyrazolo[1,5-a][1,3,5]triazin-
2-ylamino)-5-methoxy-2-methylphenyl)piperidin-
1-yl)-2-(pyrrolidin-1-yl)propan-1-one

97

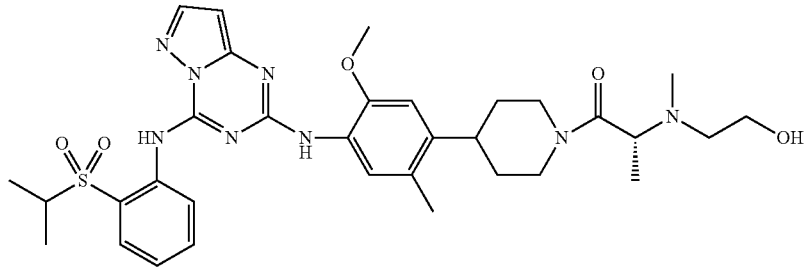

(R)-2-((2-hydroxyethyl)(methyl)amino)-1-
(4-(4-(4-(2-(isopropylsulfonyl)-
phenylamino)pyrazolo[1,5-a][1,3,5]triazin-
2-ylamino)-5-methoxy-2-methylphenyl)piperidin-
1-yl)-propan-1-one

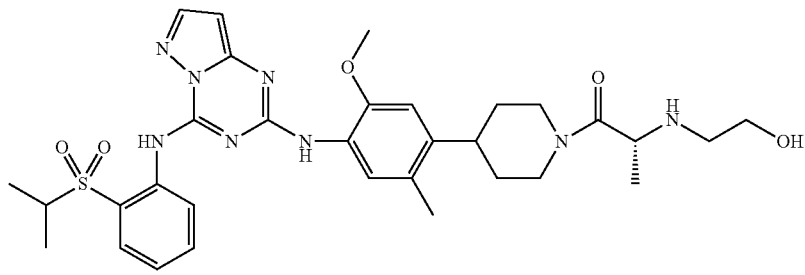

(R)-2-(2-hydroxyethylamino)-1-
(4-(4-(4-(2-(isopropylsulfonyl)-
phenylamino)pyrazolo[1,5-a][1,3,5]triazin-
2-ylamino)-5-methoxy-2-methylphenyl)piperidin-
1-yl)-propan-1-one

98

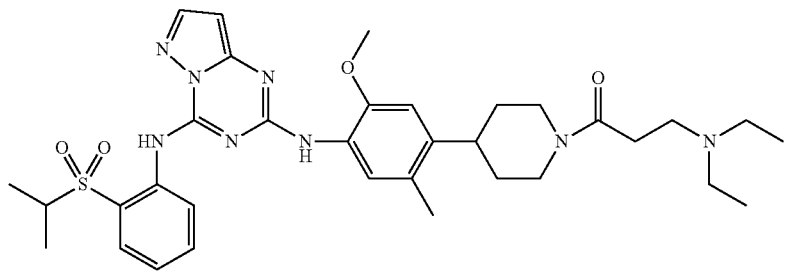

3-(diethylamino)-1-(4-(4-(4-(2-(isopropylslfonyl)-
phenylamino)pyrazolo[1,5-a][1,3,5]triazin-2-
ylamino)-5-methoxy-2-methylphenyl)-
piperidin-1-yl)propan-1-one

99

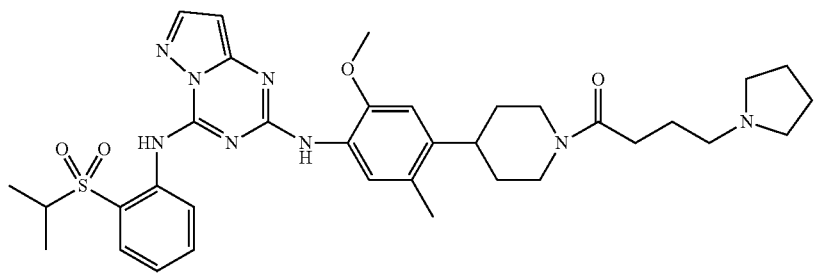

1-(4-(4-(4-(2-(isopropylslfonyl)-
phenylamino)pyrazolo[1,5-a][1,3,5]triazin-2-
ylamino)-5-methoxy-2-methylphenyl)-
piperidin-1-yl)-4-(pyrrolidin-1-yl)butan-1-one

100

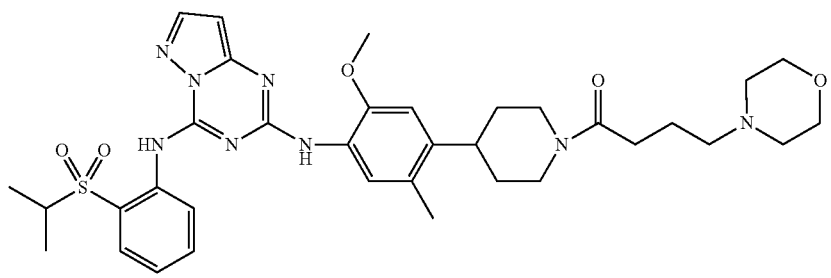

1-(4-(4-(4-(2-(isopropylslfonyl)-
phenylamino)pyrazolo[1,5-a][1,3,5]triazin-2-
ylamino)-5-methoxy-2-methylphenyl)-
piperidin-1-yl)-4-(pyrrolidin-1-yl)butan-1-one

101

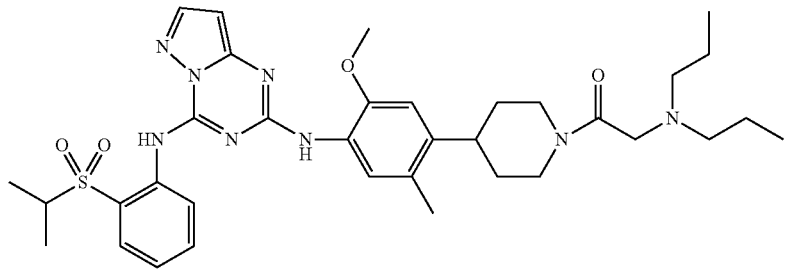

1-(4-(4-(4-(2-(isopropylslfonyl)-
phenylamino)pyrazolo[1,5-a][1,3,5]triazin-2-
ylamino)-5-methoxy-2-methylphenyl)-
piperidin-1-yl)-4-(pyrrolidin-1-yl)butan-1-one

102

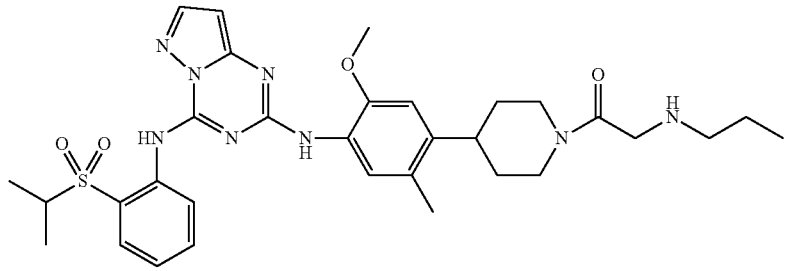

1-(4-(4-(4-(2-(isopropylslfonyl)-
phenylamino)pyrazolo[1,5-a][1,3,5]triazin-2-
ylamino)-5-methoxy-2-methylphenyl)-
piperidin-1-yl)-2-(propylamino)ethanone

103

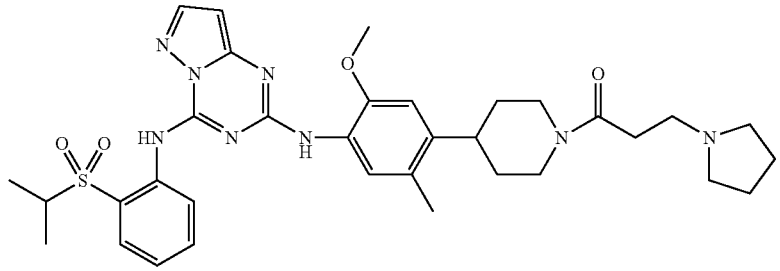

1-(4-(4-(4-(2-(isopropylslfonyl)-
phenylamino)pyrazolo[1,5-a][1,3,5]triazin-2-
ylamino)-5-methoxy-2-methylphenyl)-
piperidin-1-yl)-3-(pyrrolidin-1-yl)propan-
1-one

104

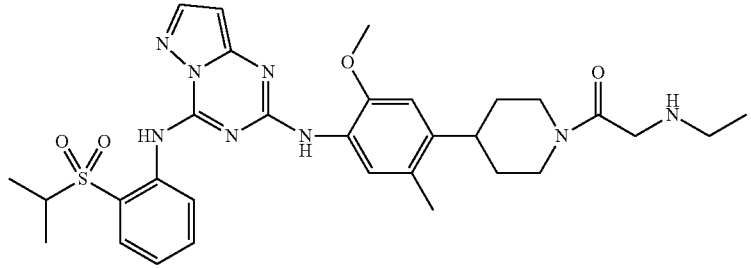

2-(ethylamino)-1-(4-(4-(4-(2-(isopropylslfonyl)-
phenylamino)pyrazolo[1,5-a][1,3,5]triazin-2-
ylamino)-5-methoxy-2-methylphenyl)-
piperidin-1-yl)-3-(pyrrolidin-1-yl)ethanone

105

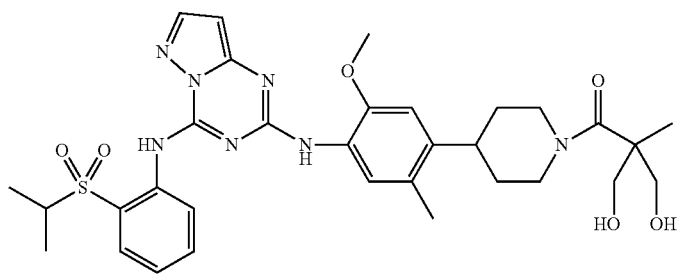

3-hydroxy-2-(hydroxymethyl)-1-(4-(4-(4-(2-(isopropylslfonyl)-
phenylamino)pyrazolo[1,5-a][1,3,5]triazin-2-
ylamino)-5-methoxy-2-methylphenyl)-
piperidin-1-yl)-2-methylpropan-1-one

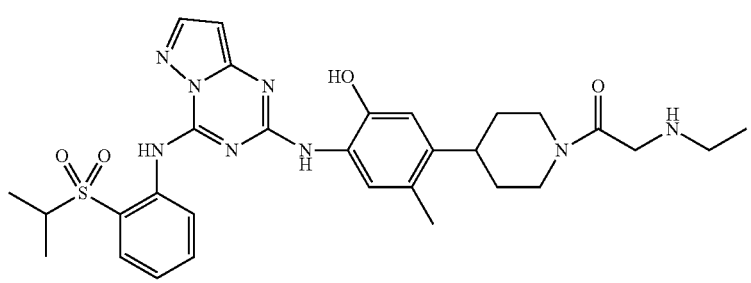

2-(ethylamino)-1-(4-(5-hydroxy-4-(4-(2-
(isopropylslfonyl)-phenylamino)pyrazolo[1,5-a]-
[1,3,5]triazin-2-ylamino)-5-methoxy-2-
methylphenyl)-piperidin-1-yl)-3-(pyrrolidin-1-
yl)ethanone

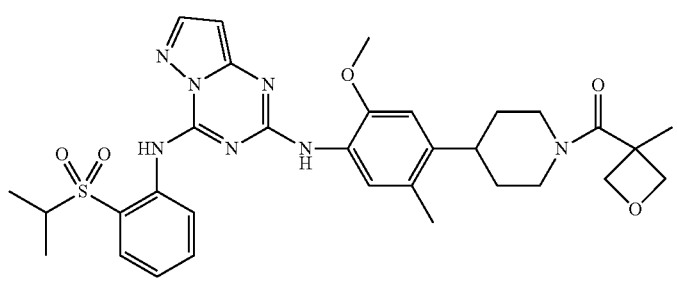

(4-(4-(4-(2-(isopropylslfonyl)-phenylamino)-
pyrazolo[1,5-a]-[1,3,5]triazin-2-ylamino)-5-
methoxy-2-methylphenyl)-piperidin-1-yl)(3-
methyloxetan-3-yl)methanone

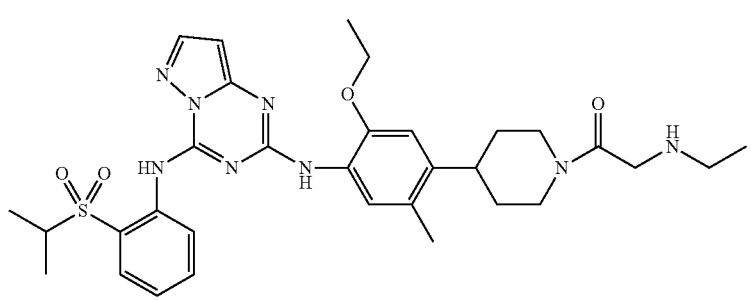

1-(4-(5-ethoxy-4-(4-(2-(isopropylslfonyl)-
phenylamino)pyrazolo[1,5-a][1,3,5]triazin-2-
ylamino)-5-methoxy-2-methylphenyl)-
piperidin-1-yl)-2-(ethylamino)ethanone; and

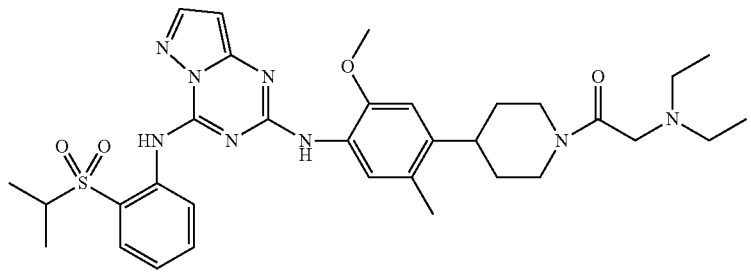

2-(diethylamino)-1-(4-(4-(4-(2-(isopropylslfonyl)-phenylamino)pyrazolo[1,5-a][1,3,5]triazin-2-ylamino)-5-methoxy-2-methylphenyl)-piperidin-1-yl)ethanone;

or pharmaceutically acceptable salts thereof.

13. A pharmaceutical composition comprising a therapeutically effective amount of a compound of claim 1 and a physiologically acceptable carrier, and optionally in combination with a second therapeutic agent.

14. The pharmaceutical composition of claim 13, wherein said second therapeutic agent is an anti-hyperproliferative agent.

15. A method for inhibiting a kinase in a cell, comprising contacting the cell with an effective amount of a compound of claim 1 or a physiologically acceptable salt thereof, and optionally in combination with a second therapeutic agent, wherein said kinase is anaplastic lymphoma kinase, thereby inhibiting said kinase.

16. A method for treating an ALK-mediated condition, comprising administering to a subject in need thereof with an effective amount of a compound of claim 1 or a pharmaceutically acceptable salt thereof, and optionally in combination with a second therapeutic agent, wherein said condition is a solid tumor of prostate, anaplastic large cell lymphoma, ALK+ non-Hodgkin's lymphoma, inflammatory myofibroblastic tumor or neuroblastoma.

17. The method of claim 16, wherein said second therapeutic agent is a chemotherapeutic agent.

18. A compound of Formula (2A), (2B) or (2C):

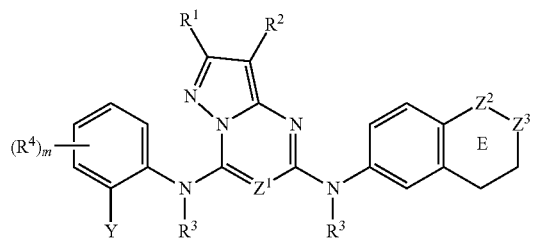

(2A)

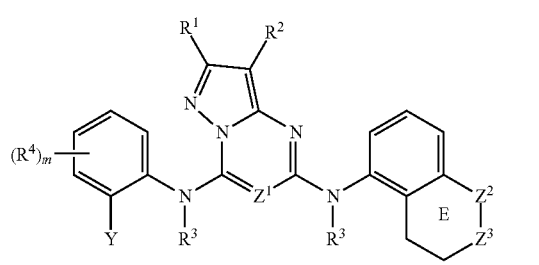

(2B)

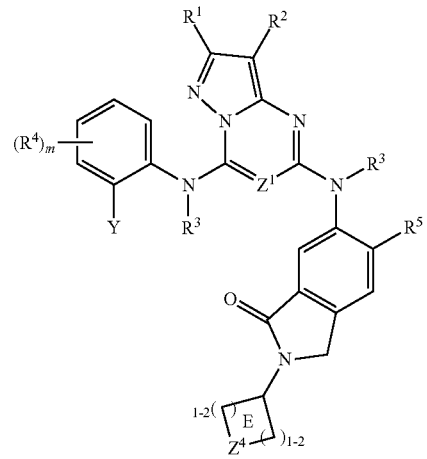

(2C)

or a physiologically acceptable salt thereof;

Y is $S(O)_{0-2}R^8$, $SO_2NRR^7$ or $CONRR^7$;

wherein one of $Z^2$ and $Z^3$ is $NR^6$, O or S, and the other is $CH_2$;

$Z^1$ is N;

$Z^4$ is $NR^6$, O or S;

ring E may optionally contain a double bond;

$R^1$ and $R^2$ are independently H, halo, $C_{1-6}$ alkyl, $C_{2-6}$ alkenyl or $C_{2-6}$ alkynyl; or $R^1$ and $R^2$ together with the ring atoms to which they are attached form a fused 5-, 6- or 7-membered cycloalkyl, aryl, heteroaryl or heterocyclic ring;

each $R^3$ is the same or different and is independently H or $C_{1-6}$ alkyl;

$R^4$ and $R^5$ are independently $C_{1-6}$ alkyl, $C_{1-6}$ alkoxy, $C_{2-6}$ alkenyl or $C_{2-6}$ alkynyl, each of which may be optionally substituted with halo, amino or hydroxyl; halo, nitro, cyano, $C(R)(OR^7)(R^7)$, $OR^7$, $NR(R^7)$, $C(R)(NRR^7)(R^7)$, $(CR_2)_q$—W, $C(O)O_{0-1}R^7$, $C(O)NR(R^7)$, $C(O)CRR^7$—$NR(R^7)$, $C(O)NR(CR_2)_pNR(R^7)$, $C(O)NR(CR_2)_pOR^7$, $C(O)NR(CR_2)_pSR^7$, $C(O)NR(CR_2)_qS(O)_{1-2}R^8$, $S(O)_{0-2}R^8$, $(CR_2)_{1-6}NR(CR_2)_pOR^7$, $(CR_2)_{1-6}NR(CR_2)_qC(O)R^8$, $S(O)_2NRR^7$, $S(O)_2NR(CR_2)_pNR(R^7)$, or $S(O)_2NR(CR_2)_pOR^7$;

$R^6$ is H, —$(CR_2)_{1-4}$—$C(O)$—$(CR_2)_q$—$OR^7$, —$C(O)OR^8$ or -L-$S(O)_2R^8$;

L is $(CR_2)_{1-4}$ or a bond;

$R^7$ and $R^8$ are independently $(CR_2)_q$—W, or $C_{1-6}$ alkyl, $C_{2-6}$ alkenyl or $C_{2-6}$ alkynyl, each of which may be optionally substituted with halo, amino, hydroxyl, or alkoxy; or $R^7$ is H;

W is a $C_{3-12}$ carbocyclic ring, $C_{6-10}$ aryl, or a 5-10 membered heteroaryl or 4-10 membered heterocyclic ring, each of which is optionally substituted with 1-3 $R^{5'}$ groups wherein $R^{5'}$ is selected from $R^5$;

each R is H or $C_{1-6}$ alkyl;

m and n are independently 0-2;

p is 2-4; and q is 0-4.

19. The compound of claim 18, wherein said compound is selected from

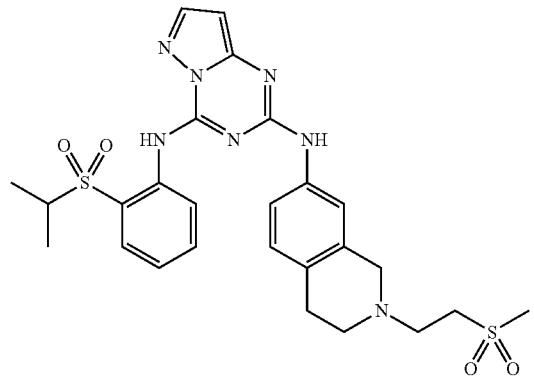

N4-(2-(isopropylsulfonyl)phenyl)-N2-(2-(2-(methylsulfonyl)ethyl)-1,2,3,4-tetrahydroisoquinolin-7-yl)-pyrazolo-[1,5-a][1,3,5]triazin-2,4-diamine

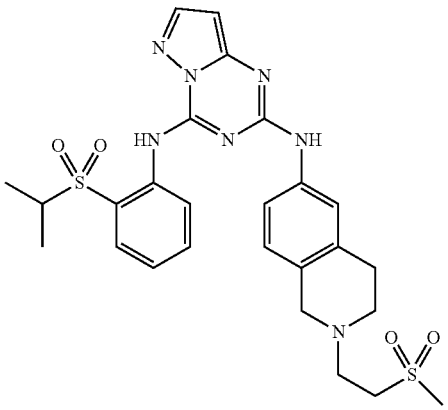

N4-(2-(isopropylsulfonyl)phenyl)-N2-(2-(2-(methylsulfonyl)-ethyl)-1,2,3,4-tetrahydroisoquinolin-6-yl)-pyrazolo-[1,5-a][1,3,5]triazin-2,4-diamine

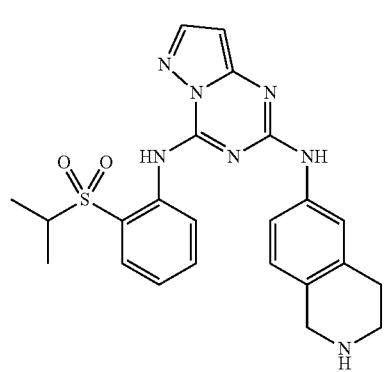

N4-(2-isopropylsulfonyl)phenyl)-N2-(1,2,3,4-tetrahydroisoquinolin-6-yl)-pyrazolo-[1,5-a][1,3,5]triazin-2,4-diamine; and

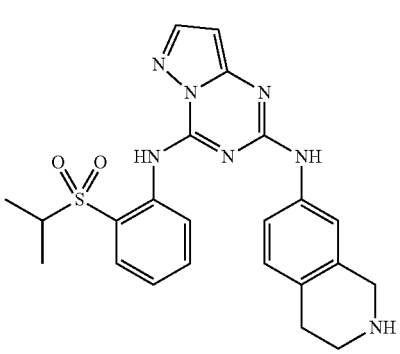

N4-(2-isopropylsulfonyl)phenyl)-N2-(1,2,3,4-tetrahydroisoquinolin-7-yl)-pyrazolo-[1,5-a][1,3,5]triazin-2,4-diamine;

or a pharmaceutically acceptable salt thereof.

* * * * *

UNITED STATES PATENT AND TRADEMARK OFFICE
CERTIFICATE OF CORRECTION

| | |
|---|---|
| PATENT NO. | : 8,518,931 B2 |
| APPLICATION NO. | : 12/936193 |
| DATED | : August 27, 2013 |
| INVENTOR(S) | : Jiang et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 285 days.

Signed and Sealed this
Eighteenth Day of November, 2014

Michelle K. Lee
*Deputy Director of the United States Patent and Trademark Office*